US012715908B2

(12) United States Patent
Livesey et al.

(10) Patent No.: US 12,715,908 B2
(45) Date of Patent: Aug. 25, 2026

(54) TAU EPITOPE AND BINDING MOLECULES

(71) Applicant: Gen2 Neuroscience Limited, Manchester (GB)

(72) Inventors: Frederick John Livesey, Manchester (GB); Clare Jones, Cambridge (GB)

(73) Assignee: Gen2 Neuroscience Limited, Manchester (GB)

( * ) Notice: Subject to any disclaimer, the term of this patent is extended or adjusted under 35 U.S.C. 154(b) by 1243 days.

(21) Appl. No.: 17/623,577

(22) PCT Filed: Jun. 29, 2020

(86) PCT No.: PCT/EP2020/068314
§ 371 (c)(1),
(2) Date: Dec. 28, 2021

(87) PCT Pub. No.: WO2020/260722
PCT Pub. Date: Dec. 30, 2020

(65) Prior Publication Data

US 2023/0192826 A1 Jun. 22, 2023

(30) Foreign Application Priority Data

Jun. 28, 2019 (GB) ..................................... 1909393

(51) Int. Cl.
*C07K 16/18* (2006.01)
*C07K 14/47* (2006.01)
*G01N 33/68* (2006.01)

(52) U.S. Cl.
CPC .......... *C07K 16/18* (2013.01); *C07K 14/4711* (2013.01); *G01N 33/6896* (2013.01); *C07K 2317/24* (2013.01); *C07K 2317/34* (2013.01); *G01N 2333/4709* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 8,697,076 | B2 | 4/2014 | Binder et al. |
| 9,139,643 | B2 | 9/2015 | Sigurdsson et al. |
| 9,777,056 | B2 | 10/2017 | Sigurdsson et al. |
| 2004/0110250 | A1 | 6/2004 | Wischik et al. |
| 2008/0050383 | A1 | 2/2008 | Sigurdsson et al. |
| 2010/0144711 | A1 | 6/2010 | Oba et al. |
| 2010/0316564 | A1 | 12/2010 | Sigurdsson |
| 2012/0087861 | A1 | 4/2012 | Nitsch et al. |
| 2012/0244174 | A1 | 9/2012 | Chain |
| 2014/0294831 | A1 | 10/2014 | Griswold-Prenner et al. |
| 2017/0260263 | A1 | 9/2017 | Novák et al. |

FOREIGN PATENT DOCUMENTS

| | | | | |
|---|---|---|---|---|
| WO | 9620218 A1 | | 7/1996 | |
| WO | 02062851 A1 | | 8/2002 | |
| WO | 2010115843 A2 | | 10/2010 | |
| WO | 2010142423 A2 | | 12/2010 | |
| WO | WO 2011/032155 | * | 3/2011 | ............. G01N 33/53 |
| WO | 2012049570 A1 | | 4/2012 | |
| WO | 2013151762 A1 | | 10/2013 | |
| WO | 2013180238 A1 | | 12/2013 | |
| WO | 2014031697 A2 | | 2/2014 | |
| WO | 2014134685 A1 | | 9/2014 | |
| WO | 2014165271 A2 | | 10/2014 | |
| WO | WO 2018/178077 | * | 10/2018 | ............. C07K 16/18 |

OTHER PUBLICATIONS

Townsend et al., Frontiers in Immunology, 2016; 7, 388 (Year: 2016).*
Janeway et al., Chapter 4—The generation of diversity in immunoglobulins in Immunobiology: The Immune system in health and disease, 5th edition, New York, Garland Science, 2001 (Year: 2001).*
Rabia et al., Biochem. Engin. J. 137, 365-374, 2018 (Year: 2018).*
Piche-Nicholas et al., MAbs. 2018; 10: 81-94. doi: 10.1080/19420862.2017.1389355 (Year: 2018).*
Liu et al., Eur J Neurosci. Author manuscript; available in PMC Mar. 3, 2008; 15 pages total (Year: 2008).*
Altschul et al. (1990) J. Mol. Biol. 215: 405-410).
Altschul et al. Nucl. Acids Res. "Gapped BLAST and PSI-BLAST: a new generation ofprotein database search programs" (1997) 25 3389-3402.
Edgar "MUSCLE: a multiple sequence alignment method with reduced time and space complexity" (2004b) BMC Bioinformatics 5:113.
Edgar "MUSCLE: multiple sequence alignment with highaccuracy and high throughput" (2004a) Nucleic Acids Res 32:1792-7;5.
FASTA (which uses the method of Pearson and Lipman (1988) PNAS USA 85:2444-2448).
Hu et al. "Minibody: A novel engineered anti-carcinoembryonic antigen antibody fragment (single-chain Fv-CH3) which exhibits rapid, high-level targeting of xenografts" (1996) Cancer Res 1056(13): 3055-61.
Kabat et al., 1991, J Immunol 147(5): 1709-19.
Kontermann "Dual targeting strategies with bispecific antibodies" (2012) Mabs 4(2): 182-97.
Lefranc et al., 2005, Dev Comp Immunol 29(3): 185-203.
Morris et al "Tau post-translational modifications in wild-type and human amyloid precursor protein transgenic mice" (2015) Nature Neuroscience 18:1183-1189.
Pedersen et al. "Tau immunotherapy for Alzheimer'sdisease" (2015) Trends Mol Med 21(6): 394-402.

(Continued)

*Primary Examiner* — Christina M Borgeest
(74) *Attorney, Agent, or Firm* — Koren Anderson

(57) ABSTRACT

The invention relates to isolated recombinant peptides comprising an epitope from human tau 2N4R. The invention also relates to use of such peptides to generate binding molecules, such as antibodies, specific for the tau epitope and to such peptides and antibodies for use in investigation, diagnosis and treatment of tauopathies, such as Alzheimer's disease.

20 Claims, 21 Drawing Sheets

Figure 1:
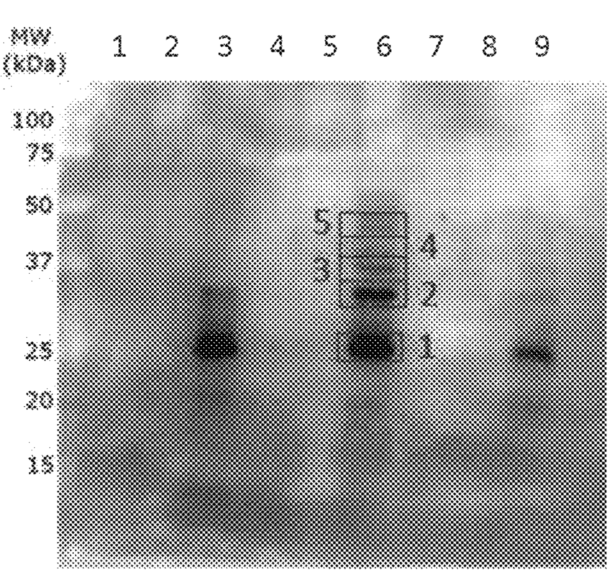

Specification includes a Sequence Listing.

(56) References Cited

OTHER PUBLICATIONS

Roberts et al.,"Pre-clinical characterisation of E2814, ahigh-affinity antibody targeting themicrotubule-binding repeat domain of taufor passive immunotherapy in Alzheimer'sdisease" 2020, Acta Neuropathologica Comms 8:13.
Sandusky-Beltran et al., "Tau immunotherapies: Lessons learned, current status and future considerations" 2020, Neuropharmacol. 175:108104.
Smith-Waterman algorithm, Smith and Waterman (1981) J. Mol Biol. 147: 195-197.
Spiess et al. "Alternative molecular formats and therapeutic applications forbispecific antibodies" (2015) Mol Immunol 67: 95-106.

* cited by examiner

A

B

A

B

A

B

A

B

C

```
SEQUENCE LISTING

<160> NUMBER OF SEQ ID NOS: 150

<210> SEQ ID NO 1
<211> LENGTH: 13
<212> TYPE: PRT
```

-continued

<213> ORGANISM: Artificial Sequence
<220> FEATURE:
<223> OTHER INFORMATION: Peptide sequence corresponding to amino acids
369-381 of 2N4R tau 1-441

<400> SEQUENCE: 1

Lys Lys Ile Glu Thr His Lys Leu Thr Phe Arg Glu Asn
1 5 10

<210> SEQ ID NO 2
<211> LENGTH: 441
<212> TYPE: PRT
<213> ORGANISM: Artificial Sequence
<220> FEATURE:
<223> OTHER INFORMATION: Full length 2N4R recombinant tau 1-441

<400> SEQUENCE: 2

Met Ala Glu Pro Arg Gln Glu Phe Glu Val Met Glu Asp His Ala Gly
1 5 10 15

Thr Tyr Gly Leu Gly Asp Arg Lys Asp Gln Gly Gly Tyr Thr Met His
20 25 30

Gln Asp Gln Glu Gly Asp Thr Asp Ala Gly Leu Lys Glu Ser Pro Leu
35 40 45

Gln Thr Pro Thr Glu Asp Gly Ser Glu Glu Pro Gly Ser Glu Thr Ser
50 55 60

Asp Ala Lys Ser Thr Pro Thr Ala Glu Asp Val Thr Ala Pro Leu Val
65 70 75 80

Asp Glu Gly Ala Pro Gly Lys Gln Ala Ala Ala Gln Pro His Thr Glu
85 90 95

Ile Pro Glu Gly Thr Thr Ala Glu Glu Ala Gly Ile Gly Asp Thr Pro
100 105 110

Ser Leu Glu Asp Glu Ala Ala Gly His Val Thr Gln Ala Arg Met Val
115 120 125

Ser Lys Ser Lys Asp Gly Thr Gly Ser Asp Asp Lys Lys Ala Lys Gly
130 135 140

Ala Asp Gly Lys Thr Lys Ile Ala Thr Pro Arg Gly Ala Ala Pro Pro
145 150 155 160

Gly Gln Lys Gly Gln Ala Asn Ala Thr Arg Ile Pro Ala Lys Thr Pro
165 170 175

Pro Ala Pro Lys Thr Pro Pro Ser Ser Gly Glu Pro Pro Lys Ser Gly
180 185 190

Asp Arg Ser Gly Tyr Ser Ser Pro Gly Ser Pro Gly Thr Pro Gly Ser
195 200 205

Arg Ser Arg Thr Pro Ser Leu Pro Thr Pro Pro Thr Arg Glu Pro Lys
210 215 220

Lys Val Ala Val Val Arg Thr Pro Pro Lys Ser Pro Ser Ser Ala Lys
225 230 235 240

Ser Arg Leu Gln Thr Ala Pro Val Pro Met Pro Asp Leu Lys Asn Val
245 250 255

Lys Ser Lys Ile Gly Ser Thr Glu Asn Leu Lys His Gln Pro Gly Gly
260 265 270

Gly Lys Val Gln Ile Ile Asn Lys Lys Leu Asp Leu Ser Asn Val Gln
275 280 285

Ser Lys Cys Gly Ser Lys Asp Asn Ile Lys His Val Pro Gly Gly Gly
290 295 300

Ser Val Gln Ile Val Tyr Lys Pro Val Asp Leu Ser Lys Val Thr Ser
305 310 315 320

```
Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440


<210> SEQ ID NO 3
<211> LENGTH: 18
<212> TYPE: PRT
<213> ORGANISM: Homo sapiens

<400> SEQUENCE: 3

Gln Glu Phe Glu Val Met Glu Asp His Ala Gly Thr Tyr Gly Leu Gly
1               5                   10                  15

Asp Arg


<210> SEQ ID NO 4
<211> LENGTH: 10
<212> TYPE: PRT
<213> ORGANISM: Homo sapiens

<400> SEQUENCE: 4

Thr Pro Pro Ser Ser Gly Glu Pro Pro Lys
1               5                   10


<210> SEQ ID NO 5
<211> LENGTH: 15
<212> TYPE: PRT
<213> ORGANISM: Homo sapiens

<400> SEQUENCE: 5

Ser Gly Tyr Ser Ser Pro Gly Ser Pro Gly Thr Pro Gly Ser Arg
1               5                   10                  15


<210> SEQ ID NO 6
<211> LENGTH: 15
<212> TYPE: PRT
<213> ORGANISM: Homo sapiens

<400> SEQUENCE: 6

Ser Arg Thr Pro Ser Leu Pro Thr Pro Pro Thr Arg Glu Pro Lys
1               5                   10                  15


<210> SEQ ID NO 7
<211> LENGTH: 13
<212> TYPE: PRT
<213> ORGANISM: Homo sapiens

<400> SEQUENCE: 7
```

```
Thr Pro Ser Leu Pro Thr Pro Pro Thr Arg Glu Pro Lys
1               5                   10


<210> SEQ ID NO 8
<211> LENGTH: 12
<212> TYPE: PRT
<213> ORGANISM: Homo sapiens

<400> SEQUENCE: 8

Leu Gln Thr Ala Pro Val Pro Met Pro Asp Leu Lys
1               5                   10


<210> SEQ ID NO 9
<211> LENGTH: 8
<212> TYPE: PRT
<213> ORGANISM: Homo sapiens

<400> SEQUENCE: 9

Ile Gly Ser Thr Glu Asn Leu Lys
1               5


<210> SEQ ID NO 10
<211> LENGTH: 12
<212> TYPE: PRT
<213> ORGANISM: Homo sapiens

<400> SEQUENCE: 10

Val Gln Ile Val Tyr Lys Pro Val Asp Leu Ser Lys
1               5                   10


<210> SEQ ID NO 11
<211> LENGTH: 16
<212> TYPE: PRT
<213> ORGANISM: Homo sapiens

<400> SEQUENCE: 11

Ile Gly Ser Leu Asp Asn Ile Thr His Val Pro Gly Gly Gly Asn Lys
1               5                   10                  15


<210> SEQ ID NO 12
<211> LENGTH: 11
<212> TYPE: PRT
<213> ORGANISM: Homo sapiens

<400> SEQUENCE: 12

Ser Pro Val Val Ser Gly Asp Thr Ser Pro Arg
1               5                   10


<210> SEQ ID NO 13
<211> LENGTH: 14
<212> TYPE: PRT
<213> ORGANISM: Artificial Sequence
<220> FEATURE:
<223> OTHER INFORMATION: Peptide sequence corresponding to amino acids
      369-381 of 2N4R tau 1-441 with N-terminal cysteine

<400> SEQUENCE: 13

Cys Lys Lys Ile Glu Thr His Lys Leu Thr Phe Arg Glu Asn
1               5                   10


<210> SEQ ID NO 14
<211> LENGTH: 5
<212> TYPE: PRT
<213> ORGANISM: Artificial Sequence
<220> FEATURE:
<223> OTHER INFORMATION: Clone 1 HCDR1
```

<400> SEQUENCE: 14

Ser Asn Ala Met Ile
1               5

<210> SEQ ID NO 15
<211> LENGTH: 16
<212> TYPE: PRT
<213> ORGANISM: Artificial Sequence
<220> FEATURE:
<223> OTHER INFORMATION: Clone 1 HCDR2

<400> SEQUENCE: 15

Asn Ile Gly Thr His Gly Thr Thr Tyr Tyr Ala Ser Trp Ala Lys Gly
1               5                   10                  15

<210> SEQ ID NO 16
<211> LENGTH: 3
<212> TYPE: PRT
<213> ORGANISM: Artificial Sequence
<220> FEATURE:
<223> OTHER INFORMATION: Clone 1 HCDR3

<400> SEQUENCE: 16

Gly Asp Ile
1

<210> SEQ ID NO 17
<211> LENGTH: 13
<212> TYPE: PRT
<213> ORGANISM: Artificial Sequence
<220> FEATURE:
<223> OTHER INFORMATION: Clone 1 LCDR1

<400> SEQUENCE: 17

Gln Ala Ser Gln Ser Val Asp Asp Asn Asn Asn Leu Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Clone 1 LCDR2

<400> SEQUENCE: 18

Glu Ala Ser Thr Leu Ala Ser
1               5

<210> SEQ ID NO 19
<211> LENGTH: 13
<212> TYPE: PRT
<213> ORGANISM: Artificial Sequence
<220> FEATURE:
<223> OTHER INFORMATION: Clone 1 LCDR3

<400> SEQUENCE: 19

Leu Gly Glu Phe Ser Cys Ser Ser Ala Asp Cys Val Val
1               5                   10

<210> SEQ ID NO 20
<211> LENGTH: 5
<212> TYPE: PRT
<213> ORGANISM: Artificial Sequence
<220> FEATURE:
<223> OTHER INFORMATION: Clone 2 HCDR1

<400> SEQUENCE: 20

```
Ser Tyr Ala Met Ala
1               5
```

<210> SEQ ID NO 21
<211> LENGTH: 16
<212> TYPE: PRT
<213> ORGANISM: Artificial Sequence
<220> FEATURE:
<223> OTHER INFORMATION: Clone 2 HCDR2

<400> SEQUENCE: 21

```
Cys Ile Asp Arg Arg Gly Gly Thr Phe Tyr Ala Ser Trp Val Lys Gly
1               5                   10                  15
```

<210> SEQ ID NO 22
<211> LENGTH: 7
<212> TYPE: PRT
<213> ORGANISM: Artificial Sequence
<220> FEATURE:
<223> OTHER INFORMATION: Clone 2 HCDR3

<400> SEQUENCE: 22

```
Asp Ser Gly Ala Phe Asp Pro
1               5
```

<210> SEQ ID NO 23
<211> LENGTH: 12
<212> TYPE: PRT
<213> ORGANISM: Artificial Sequence
<220> FEATURE:
<223> OTHER INFORMATION: Clone 2 LCDR1

<400> SEQUENCE: 23

```
Gln Ala Ser Gln Ser Val Tyr Asp Asn Tyr Leu Ala
1               5                   10
```

<210> SEQ ID NO 24
<211> LENGTH: 7
<212> TYPE: PRT
<213> ORGANISM: Artificial Sequence
<220> FEATURE:
<223> OTHER INFORMATION: Clone 2 LCDR2

<400> SEQUENCE: 24

```
Ala Ala Ser Asn Leu Ala Ser
1               5
```

<210> SEQ ID NO 25
<211> LENGTH: 13
<212> TYPE: PRT
<213> ORGANISM: Artificial Sequence
<220> FEATURE:
<223> OTHER INFORMATION: Clone 2 LCDR3

<400> SEQUENCE: 25

```
Leu Gly Glu Phe Ser Cys Thr Thr Thr Asp Cys Asn Val
1               5                   10
```

<210> SEQ ID NO 26
<211> LENGTH: 5
<212> TYPE: PRT
<213> ORGANISM: Artificial Sequence
<220> FEATURE:
<223> OTHER INFORMATION: Clone 3 HCDR1

<400> SEQUENCE: 26

Ser Tyr Ala Val Gly
1 5

<210> SEQ ID NO 27
<211> LENGTH: 16
<212> TYPE: PRT
<213> ORGANISM: Artificial Sequence
<220> FEATURE:
<223> OTHER INFORMATION: Clone 3 HCDR2

<400> SEQUENCE: 27

Cys Ile Asp Ser Arg Asp Ser Lys Phe Tyr Ala Ser Trp Ala Lys Gly
1 5 10 15

<210> SEQ ID NO 28
<211> LENGTH: 7
<212> TYPE: PRT
<213> ORGANISM: Artificial Sequence
<220> FEATURE:
<223> OTHER INFORMATION: Clone 3 HCDR3

<400> SEQUENCE: 28

Asp Ser Gly Ala Phe Asn Pro
1 5

<210> SEQ ID NO 29
<211> LENGTH: 12
<212> TYPE: PRT
<213> ORGANISM: Artificial Sequence
<220> FEATURE:
<223> OTHER INFORMATION: Clone 3 LCDR1

<400> SEQUENCE: 29

Gln Ala Ser Gln Ser Val Tyr Asp Asn Tyr Leu Ala
1 5 10

<210> SEQ ID NO 30
<211> LENGTH: 7
<212> TYPE: PRT
<213> ORGANISM: Artificial Sequence
<220> FEATURE:
<223> OTHER INFORMATION: Clone 3 LCDR2

<400> SEQUENCE: 30

Ala Val Ser Asn Leu Ala Ser
1 5

<210> SEQ ID NO 31
<211> LENGTH: 13
<212> TYPE: PRT
<213> ORGANISM: Artificial Sequence
<220> FEATURE:
<223> OTHER INFORMATION: Clone 3 LCDR3

<400> SEQUENCE: 31

Leu Gly Glu Phe Tyr Cys Ser Ser Ile Asp Cys Asn Ala
1 5 10

<210> SEQ ID NO 32
<211> LENGTH: 5
<212> TYPE: PRT
<213> ORGANISM: Artificial Sequence
<220> FEATURE:
<223> OTHER INFORMATION: Clone 4 HCDR1

<400> SEQUENCE: 32

```
Ser Tyr Ala Val Gly
1               5


<210> SEQ ID NO 33
<211> LENGTH: 16
<212> TYPE: PRT
<213> ORGANISM: Artificial Sequence
<220> FEATURE:
<223> OTHER INFORMATION: Clone 4 HCDR2

<400> SEQUENCE: 33

Cys Ile Asp Gly Arg Asp Ser Ala Phe Tyr Ala Ser Trp Ala Lys Gly
1               5                   10                  15


<210> SEQ ID NO 34
<211> LENGTH: 7
<212> TYPE: PRT
<213> ORGANISM: Artificial Sequence
<220> FEATURE:
<223> OTHER INFORMATION: Clone 4 HCDR3

<400> SEQUENCE: 34

Asp Ser Gly Ala Phe Asn Pro
1               5


<210> SEQ ID NO 35
<211> LENGTH: 12
<212> TYPE: PRT
<213> ORGANISM: Artificial Sequence
<220> FEATURE:
<223> OTHER INFORMATION: Clone 4 LCDR1

<400> SEQUENCE: 35

Gln Ala Ser Gln Ser Val Tyr Asp Asn Tyr Leu Ser
1               5                   10


<210> SEQ ID NO 36
<211> LENGTH: 7
<212> TYPE: PRT
<213> ORGANISM: Artificial Sequence
<220> FEATURE:
<223> OTHER INFORMATION: Clone 4 LCDR2

<400> SEQUENCE: 36

Ala Val Ser Asn Leu Ala Ser
1               5


<210> SEQ ID NO 37
<211> LENGTH: 13
<212> TYPE: PRT
<213> ORGANISM: Artificial Sequence
<220> FEATURE:
<223> OTHER INFORMATION: Clone 4 LCDR3

<400> SEQUENCE: 37

Leu Gly Glu Phe Tyr Cys Ser Ser Ile Asp Cys Asn Ala
1               5                   10


<210> SEQ ID NO 38
<211> LENGTH: 5
<212> TYPE: PRT
<213> ORGANISM: Artificial Sequence
<220> FEATURE:
<223> OTHER INFORMATION: Clone 5 HCDR1

<400> SEQUENCE: 38

Thr Tyr Ala Met Ala
```

1 5

<210> SEQ ID NO 39
<211> LENGTH: 16
<212> TYPE: PRT
<213> ORGANISM: Artificial Sequence
<220> FEATURE:
<223> OTHER INFORMATION: Clone 5 HCDR2

<400> SEQUENCE: 39

Cys Ile Asp Arg Arg Gly Gly Thr Phe Tyr Ala Ser Trp Ala Lys Gly
1 5 10 15

<210> SEQ ID NO 40
<211> LENGTH: 7
<212> TYPE: PRT
<213> ORGANISM: Artificial Sequence
<220> FEATURE:
<223> OTHER INFORMATION: Clone 5 HCDR3

<400> SEQUENCE: 40

Asp Ser Gly Ala Phe Asp Pro
1 5

<210> SEQ ID NO 41
<211> LENGTH: 12
<212> TYPE: PRT
<213> ORGANISM: Artificial Sequence
<220> FEATURE:
<223> OTHER INFORMATION: Clone 5 LCDR1

<400> SEQUENCE: 41

Gln Ala Ser Gln Ser Val Tyr Asp Asn Tyr Leu Ala
1 5 10

<210> SEQ ID NO 42
<211> LENGTH: 7
<212> TYPE: PRT
<213> ORGANISM: Artificial Sequence
<220> FEATURE:
<223> OTHER INFORMATION: Clone 5 LCDR2

<400> SEQUENCE: 42

Ala Ala Ser Asn Leu Ala Ser
1 5

<210> SEQ ID NO 43
<211> LENGTH: 13
<212> TYPE: PRT
<213> ORGANISM: Artificial Sequence
<220> FEATURE:
<223> OTHER INFORMATION: Clone 5 LCDR3

<400> SEQUENCE: 43

Leu Gly Glu Phe Ser Cys Thr Thr Thr Asp Cys Asn Val
1 5 10

<210> SEQ ID NO 44
<211> LENGTH: 5
<212> TYPE: PRT
<213> ORGANISM: Artificial Sequence
<220> FEATURE:
<223> OTHER INFORMATION: Clone 6 HCDR1

<400> SEQUENCE: 44

Lys Asn Ala Met Ile
1 5

<210> SEQ ID NO 45
<211> LENGTH: 16
<212> TYPE: PRT
<213> ORGANISM: Artificial Sequence
<220> FEATURE:
<223> OTHER INFORMATION: Clone 6 HCDR2

<400> SEQUENCE: 45

Asn Ile Gly Thr Arg Gly Thr Thr Tyr Tyr Ala Ser Trp Thr Lys Gly
1               5                   10                  15

<210> SEQ ID NO 46
<211> LENGTH: 3
<212> TYPE: PRT
<213> ORGANISM: Artificial Sequence
<220> FEATURE:
<223> OTHER INFORMATION: Clone 6 HCDR3

<400> SEQUENCE: 46

Gly Asp Ile
1

<210> SEQ ID NO 47
<211> LENGTH: 12
<212> TYPE: PRT
<213> ORGANISM: Artificial Sequence
<220> FEATURE:
<223> OTHER INFORMATION: Clone 6 LCDR1

<400> SEQUENCE: 47

Gln Ser Ser Gln Ser Val Asn Asn Asn Asp Leu Ala
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Clone 6 LCDR2

<400> SEQUENCE: 48

Glu Ala Ser Thr Leu Ala Ser
1               5

<210> SEQ ID NO 49
<211> LENGTH: 13
<212> TYPE: PRT
<213> ORGANISM: Artificial Sequence
<220> FEATURE:
<223> OTHER INFORMATION: Clone 6 LCDR3

<400> SEQUENCE: 49

Leu Gly Glu Phe Ser Cys Ser Ser Ala Asp Cys Val Ala
1               5                   10

<210> SEQ ID NO 50
<211> LENGTH: 5
<212> TYPE: PRT
<213> ORGANISM: Artificial Sequence
<220> FEATURE:
<223> OTHER INFORMATION: Clone 7 HCDR1

<400> SEQUENCE: 50

Ser Tyr Ala Met Ser
1               5

<210> SEQ ID NO 51
<211> LENGTH: 16
<212> TYPE: PRT
<213> ORGANISM: Artificial Sequence
<220> FEATURE:
<223> OTHER INFORMATION: Clone 7 HCDR2

<400> SEQUENCE: 51

Cys Ile Asp Ser Arg Gly Ser Val Tyr Tyr Ala Ser Trp Ala Lys Gly
1 5 10 15

<210> SEQ ID NO 52
<211> LENGTH: 7
<212> TYPE: PRT
<213> ORGANISM: Artificial Sequence
<220> FEATURE:
<223> OTHER INFORMATION: Clone 7 HCDR3

<400> SEQUENCE: 52

Asp Ser Gly Ala Phe Asp Pro
1 5

<210> SEQ ID NO 53
<211> LENGTH: 12
<212> TYPE: PRT
<213> ORGANISM: Artificial Sequence
<220> FEATURE:
<223> OTHER INFORMATION: Clone 7 LCDR1

<400> SEQUENCE: 53

Gln Ala Ser Gln Ser Val Tyr Asp Asn Tyr Leu Ser
1 5 10

<210> SEQ ID NO 54
<211> LENGTH: 7
<212> TYPE: PRT
<213> ORGANISM: Artificial Sequence
<220> FEATURE:
<223> OTHER INFORMATION: Clone 7 LCDR2

<400> SEQUENCE: 54

Ala Ala Ser Asn Leu Ala Ser
1 5

<210> SEQ ID NO 55
<211> LENGTH: 13
<212> TYPE: PRT
<213> ORGANISM: Artificial Sequence
<220> FEATURE:
<223> OTHER INFORMATION: Clone 7 LCDR3

<400> SEQUENCE: 55

Leu Gly Glu Phe Tyr Cys Ser Ser Met Asp Cys Asn Ala
1 5 10

<210> SEQ ID NO 56
<211> LENGTH: 5
<212> TYPE: PRT
<213> ORGANISM: Artificial Sequence
<220> FEATURE:
<223> OTHER INFORMATION: Clone 8 HCDR1

<400> SEQUENCE: 56

Ser Asn Ala Met Ile
1 5

```
<210> SEQ ID NO 57
<211> LENGTH: 16
<212> TYPE: PRT
<213> ORGANISM: Artificial Sequence
<220> FEATURE:
<223> OTHER INFORMATION: Clone 8 HCDR2

<400> SEQUENCE: 57

Asn Ile Gly Thr His Gly Thr Thr Tyr Tyr Ala Ser Trp Ala Lys Gly
1               5                   10                  15


<210> SEQ ID NO 58
<211> LENGTH: 3
<212> TYPE: PRT
<213> ORGANISM: Artificial Sequence
<220> FEATURE:
<223> OTHER INFORMATION: Clone 8 HCDR3

<400> SEQUENCE: 58

Gly Asp Ile
1


<210> SEQ ID NO 59
<211> LENGTH: 13
<212> TYPE: PRT
<213> ORGANISM: Artificial Sequence
<220> FEATURE:
<223> OTHER INFORMATION: Clone 8 LCDR1

<400> SEQUENCE: 59

Gln Ala Ser Gln Ser Val Asp Asn Asn Asn Asn Leu Ala
1               5                   10


<210> SEQ ID NO 60
<211> LENGTH: 7
<212> TYPE: PRT
<213> ORGANISM: Artificial Sequence
<220> FEATURE:
<223> OTHER INFORMATION: Clone 8 LCDR2

<400> SEQUENCE: 60

Glu Ala Ser Thr Leu Ala Ser
1               5


<210> SEQ ID NO 61
<211> LENGTH: 13
<212> TYPE: PRT
<213> ORGANISM: Artificial Sequence
<220> FEATURE:
<223> OTHER INFORMATION: Clone 8 LCDR3

<400> SEQUENCE: 61

Leu Gly Glu Phe Ser Cys Ser Ser Ala Asp Cys Val Ala
1               5                   10


<210> SEQ ID NO 62
<211> LENGTH: 5
<212> TYPE: PRT
<213> ORGANISM: Artificial Sequence
<220> FEATURE:
<223> OTHER INFORMATION: Clone 9 HCDR1

<400> SEQUENCE: 62

Ser Tyr Ala Val Gly
1               5


<210> SEQ ID NO 63
```

<211> LENGTH: 16
<212> TYPE: PRT
<213> ORGANISM: Artificial Sequence
<220> FEATURE:
<223> OTHER INFORMATION: Clone 9 HCDR2

<400> SEQUENCE: 63

Cys Ile Asp Ser His Asp Asn Thr Phe Tyr Ala Ser Trp Ala Lys Gly
1 5 10 15

<210> SEQ ID NO 64
<211> LENGTH: 7
<212> TYPE: PRT
<213> ORGANISM: Artificial Sequence
<220> FEATURE:
<223> OTHER INFORMATION: Clone 9 HCDR3

<400> SEQUENCE: 64

Asp Ser Gly Ala Phe Asn Pro
1 5

<210> SEQ ID NO 65
<211> LENGTH: 12
<212> TYPE: PRT
<213> ORGANISM: Artificial Sequence
<220> FEATURE:
<223> OTHER INFORMATION: Clone 9 LCDR1

<400> SEQUENCE: 65

Gln Ala Ser Gln Ser Val Tyr Asp Asn Tyr Leu Ser
1 5 10

<210> SEQ ID NO 66
<211> LENGTH: 7
<212> TYPE: PRT
<213> ORGANISM: Artificial Sequence
<220> FEATURE:
<223> OTHER INFORMATION: Clone 9 LCDR2

<400> SEQUENCE: 66

Ala Val Ser Asn Leu Ala Ser
1 5

<210> SEQ ID NO 67
<211> LENGTH: 13
<212> TYPE: PRT
<213> ORGANISM: Artificial Sequence
<220> FEATURE:
<223> OTHER INFORMATION: Clone 9 LCDR3

<400> SEQUENCE: 67

Leu Gly Glu Phe Tyr Cys Ser Ser Ile Asp Cys Asn Ala
1 5 10

<210> SEQ ID NO 68
<211> LENGTH: 5
<212> TYPE: PRT
<213> ORGANISM: Artificial Sequence
<220> FEATURE:
<223> OTHER INFORMATION: Clone 10 HCDR1

<400> SEQUENCE: 68

Ser Asn Ala Met Ile
1 5

<210> SEQ ID NO 69
<211> LENGTH: 16

<212> TYPE: PRT
<213> ORGANISM: Artificial Sequence
<220> FEATURE:
<223> OTHER INFORMATION: Clone 10 HCDR2

<400> SEQUENCE: 69

Asn Ile Gly Thr His Gly Thr Thr Tyr Tyr Ala Ser Trp Ser Lys Gly
1 5 10 15

<210> SEQ ID NO 70
<211> LENGTH: 3
<212> TYPE: PRT
<213> ORGANISM: Artificial Sequence
<220> FEATURE:
<223> OTHER INFORMATION: Clone 10 HCDR3

<400> SEQUENCE: 70

Gly Asp Ile
1

<210> SEQ ID NO 71
<211> LENGTH: 13
<212> TYPE: PRT
<213> ORGANISM: Artificial Sequence
<220> FEATURE:
<223> OTHER INFORMATION: Clone 10 LCDR1

<400> SEQUENCE: 71

Gln Ala Ser Gln Ser Val Asp Asn Asn Asn Asn Leu Ala
1 5 10

<210> SEQ ID NO 72
<211> LENGTH: 7
<212> TYPE: PRT
<213> ORGANISM: Artificial Sequence
<220> FEATURE:
<223> OTHER INFORMATION: Clone 10 LCDR2

<400> SEQUENCE: 72

Glu Ala Ser Thr Leu Ala Ser
1 5

<210> SEQ ID NO 73
<211> LENGTH: 13
<212> TYPE: PRT
<213> ORGANISM: Artificial Sequence
<220> FEATURE:
<223> OTHER INFORMATION: Clone 10 LCDR3

<400> SEQUENCE: 73

Leu Gly Glu Phe Ser Cys Ser Ser Ala Asp Cys Val Ala
1 5 10

<210> SEQ ID NO 74
<211> LENGTH: 5
<212> TYPE: PRT
<213> ORGANISM: Artificial Sequence
<220> FEATURE:
<223> OTHER INFORMATION: Clone 11 HCDR1

<400> SEQUENCE: 74

Asn Tyr Ala Met Ala
1 5

<210> SEQ ID NO 75
<211> LENGTH: 16
<212> TYPE: PRT

<213> ORGANISM: Artificial Sequence
<220> FEATURE:
<223> OTHER INFORMATION: Clone 11 HCDR2

<400> SEQUENCE: 75

Cys Ile Asp Arg Arg Gly Gly Thr Phe Tyr Ala Ser Trp Ala Lys Gly
1 5 10 15

<210> SEQ ID NO 76
<211> LENGTH: 7
<212> TYPE: PRT
<213> ORGANISM: Artificial Sequence
<220> FEATURE:
<223> OTHER INFORMATION: Clone 11 HCDR3

<400> SEQUENCE: 76

Asp Ser Gly Ala Phe Asp Pro
1 5

<210> SEQ ID NO 77
<211> LENGTH: 12
<212> TYPE: PRT
<213> ORGANISM: Artificial Sequence
<220> FEATURE:
<223> OTHER INFORMATION: Clone 11 LCDR1

<400> SEQUENCE: 77

Gln Ala Ser Gln Ser Val Tyr Asp Asn Tyr Leu Ala
1 5 10

<210> SEQ ID NO 78
<211> LENGTH: 7
<212> TYPE: PRT
<213> ORGANISM: Artificial Sequence
<220> FEATURE:
<223> OTHER INFORMATION: Clone 11 LCDR2

<400> SEQUENCE: 78

Ala Ala Ser Asn Leu Ala Ser
1 5

<210> SEQ ID NO 79
<211> LENGTH: 13
<212> TYPE: PRT
<213> ORGANISM: Artificial Sequence
<220> FEATURE:
<223> OTHER INFORMATION: Clone 11 LCDR3

<400> SEQUENCE: 79

Leu Gly Glu Phe Ser Cys Thr Thr Thr Asp Cys Asn Val
1 5 10

<210> SEQ ID NO 80
<211> LENGTH: 5
<212> TYPE: PRT
<213> ORGANISM: Artificial Sequence
<220> FEATURE:
<223> OTHER INFORMATION: Clone 12 HCDR1

<400> SEQUENCE: 80

Ser Tyr Ala Val Gly
1 5

<210> SEQ ID NO 81
<211> LENGTH: 16
<212> TYPE: PRT
<213> ORGANISM: Artificial Sequence
<220> FEATURE:
<223> OTHER INFORMATION: Clone 12 HCDR2

<400> SEQUENCE: 81

Cys Ile Asp Ser His Asp Asn Thr Phe Tyr Ala Ser Trp Ala Lys Ser
1 5 10 15

<210> SEQ ID NO 82
<211> LENGTH: 7
<212> TYPE: PRT
<213> ORGANISM: Artificial Sequence
<220> FEATURE:
<223> OTHER INFORMATION: Clone 12 HCDR3

<400> SEQUENCE: 82

Asp Ser Gly Ala Phe Asn Pro
1 5

<210> SEQ ID NO 83
<211> LENGTH: 12
<212> TYPE: PRT
<213> ORGANISM: Artificial Sequence
<220> FEATURE:
<223> OTHER INFORMATION: Clone 12 LCDR1

<400> SEQUENCE: 83

Gln Ala Ser Gln Ser Val Tyr Asp Asn Tyr Leu Ser
1 5 10

<210> SEQ ID NO 84
<211> LENGTH: 7
<212> TYPE: PRT
<213> ORGANISM: Artificial Sequence
<220> FEATURE:
<223> OTHER INFORMATION: Clone 12 LCDR2

<400> SEQUENCE: 84

Ala Val Ser Asn Leu Ala Ser
1 5

<210> SEQ ID NO 85
<211> LENGTH: 13
<212> TYPE: PRT
<213> ORGANISM: Artificial Sequence
<220> FEATURE:
<223> OTHER INFORMATION: Clone 12 LCDR3

<400> SEQUENCE: 85

Leu Gly Glu Phe Tyr Cys Ser Ser Ile Asp Cys Asn Ala
1 5 10

<210> SEQ ID NO 86
<211> LENGTH: 5
<212> TYPE: PRT
<213> ORGANISM: Artificial Sequence
<220> FEATURE:
<223> OTHER INFORMATION: Clone 13 HCDR1

<400> SEQUENCE: 86

Ser Tyr Ala Met Gly
1 5

<210> SEQ ID NO 87
<211> LENGTH: 16
<212> TYPE: PRT
<213> ORGANISM: Artificial Sequence
<220> FEATURE:

<223> OTHER INFORMATION: Clone 13 HCDR2

<400> SEQUENCE: 87

Cys Ile Asp Arg Arg Gly Ala Thr Phe Tyr Ala Ser Trp Ala Lys Gly
1 5 10 15

<210> SEQ ID NO 88
<211> LENGTH: 7
<212> TYPE: PRT
<213> ORGANISM: Artificial Sequence
<220> FEATURE:
<223> OTHER INFORMATION: Clone 13 HCDR3

<400> SEQUENCE: 88

Asp Ser Gly Ala Phe Asp Pro
1 5

<210> SEQ ID NO 89
<211> LENGTH: 12
<212> TYPE: PRT
<213> ORGANISM: Artificial Sequence
<220> FEATURE:
<223> OTHER INFORMATION: Clone 13 LCDR1

<400> SEQUENCE: 89

Gln Ala Ser Gln Ser Val Tyr Asp Asn Tyr Leu Ser
1 5 10

<210> SEQ ID NO 90
<211> LENGTH: 7
<212> TYPE: PRT
<213> ORGANISM: Artificial Sequence
<220> FEATURE:
<223> OTHER INFORMATION: Clone 13 LCDR2

<400> SEQUENCE: 90

Ala Ala Ser Asn Leu Ala Ser
1 5

<210> SEQ ID NO 91
<211> LENGTH: 13
<212> TYPE: PRT
<213> ORGANISM: Artificial Sequence
<220> FEATURE:
<223> OTHER INFORMATION: Clone 13 LCDR3

<400> SEQUENCE: 91

Leu Gly Glu Phe Ser Cys Thr Thr Thr Asp Cys Asn Val
1 5 10

<210> SEQ ID NO 92
<211> LENGTH: 5
<212> TYPE: PRT
<213> ORGANISM: Artificial Sequence
<220> FEATURE:
<223> OTHER INFORMATION: Clone 14 HCDR1

<400> SEQUENCE: 92

Ser Tyr Ala Met Gly
1 5

<210> SEQ ID NO 93
<211> LENGTH: 16
<212> TYPE: PRT
<213> ORGANISM: Artificial Sequence
<220> FEATURE:
<223> OTHER INFORMATION: Clone 14 HCDR2

<400> SEQUENCE: 93

Cys Ile Asp Arg Arg Gly Gly Thr Phe Tyr Ala Ser Trp Ala Lys Gly
1 5 10 15

<210> SEQ ID NO 94
<211> LENGTH: 7
<212> TYPE: PRT
<213> ORGANISM: Artificial Sequence
<220> FEATURE:
<223> OTHER INFORMATION: Clone 14 HCDR3

<400> SEQUENCE: 94

Asp Ser Gly Ala Phe Asp Pro
1 5

<210> SEQ ID NO 95
<211> LENGTH: 12
<212> TYPE: PRT
<213> ORGANISM: Artificial Sequence
<220> FEATURE:
<223> OTHER INFORMATION: Clone 14 LCDR1

<400> SEQUENCE: 95

Gln Ala Ser Gln Ser Val Tyr Asp Asn Tyr Leu Ala
1 5 10

<210> SEQ ID NO 96
<211> LENGTH: 7
<212> TYPE: PRT
<213> ORGANISM: Artificial Sequence
<220> FEATURE:
<223> OTHER INFORMATION: Clone 14 LCDR2

<400> SEQUENCE: 96

Ala Ala Ser Asn Leu Ala Ser
1 5

<210> SEQ ID NO 97
<211> LENGTH: 13
<212> TYPE: PRT
<213> ORGANISM: Artificial Sequence
<220> FEATURE:
<223> OTHER INFORMATION: Clone 14 LCDR3

<400> SEQUENCE: 97

Leu Gly Glu Phe Ser Cys Thr Thr Thr Asp Cys Asn Val
1 5 10

<210> SEQ ID NO 98
<211> LENGTH: 5
<212> TYPE: PRT
<213> ORGANISM: Artificial Sequence
<220> FEATURE:
<223> OTHER INFORMATION: Clone 15 HCDR1

<400> SEQUENCE: 98

Ser Tyr Ala Met Thr
1 5

<210> SEQ ID NO 99
<211> LENGTH: 16
<212> TYPE: PRT
<213> ORGANISM: Artificial Sequence
<220> FEATURE:
<223> OTHER INFORMATION: Clone 15 HCDR2

<400> SEQUENCE: 99

Cys Ile Asp Thr Gly Gly Ser Ala Tyr Tyr Ala Ser Trp Ala Lys Gly
1 5 10 15

<210> SEQ ID NO 100
<211> LENGTH: 7
<212> TYPE: PRT
<213> ORGANISM: Artificial Sequence
<220> FEATURE:
<223> OTHER INFORMATION: Clone 15 HCDR3

<400> SEQUENCE: 100

Asp Thr Gly Ala Phe Asp Pro
1 5

<210> SEQ ID NO 101
<211> LENGTH: 12
<212> TYPE: PRT
<213> ORGANISM: Artificial Sequence
<220> FEATURE:
<223> OTHER INFORMATION: Clone 15 LCDR1

<400> SEQUENCE: 101

Gln Ala Ser Gln Ser Val Tyr Asp Asn Asn Leu Ala
1 5 10

<210> SEQ ID NO 102
<211> LENGTH: 7
<212> TYPE: PRT
<213> ORGANISM: Artificial Sequence
<220> FEATURE:
<223> OTHER INFORMATION: Clone 15 LCDR2

<400> SEQUENCE: 102

Ala Ala Ser Asn Leu Pro Ser
1 5

<210> SEQ ID NO 103
<211> LENGTH: 13
<212> TYPE: PRT
<213> ORGANISM: Artificial Sequence
<220> FEATURE:
<223> OTHER INFORMATION: Clone 15 LCDR3

<400> SEQUENCE: 103

Leu Gly Glu Phe Ser Cys Ser Ser Thr Asp Cys Asn Ala
1 5 10

<210> SEQ ID NO 104
<211> LENGTH: 5
<212> TYPE: PRT
<213> ORGANISM: Artificial Sequence
<220> FEATURE:
<223> OTHER INFORMATION: Clone 16 HCDR1

<400> SEQUENCE: 104

Ser Tyr Ala Val Gly
1 5

<210> SEQ ID NO 105
<211> LENGTH: 16
<212> TYPE: PRT
<213> ORGANISM: Artificial Sequence
<220> FEATURE:
<223> OTHER INFORMATION: Clone 16 HCDR2

<400> SEQUENCE: 105

```
Cys Ile Asp Ser Arg Asp Ser Ala Phe Tyr Ala Ser Trp Ala Lys Gly
1               5                   10                  15


<210> SEQ ID NO 106
<211> LENGTH: 7
<212> TYPE: PRT
<213> ORGANISM: Artificial Sequence
<220> FEATURE:
<223> OTHER INFORMATION: Clone 16 HCDR3

<400> SEQUENCE: 106

Asp Ser Gly Ala Phe Asn Pro
1               5


<210> SEQ ID NO 107
<211> LENGTH: 12
<212> TYPE: PRT
<213> ORGANISM: Artificial Sequence
<220> FEATURE:
<223> OTHER INFORMATION: Clone 16 LCDR1

<400> SEQUENCE: 107

Gln Ala Ser Gln Ser Val Tyr Asp Asn Tyr Leu Ser
1               5                   10


<210> SEQ ID NO 108
<211> LENGTH: 7
<212> TYPE: PRT
<213> ORGANISM: Artificial Sequence
<220> FEATURE:
<223> OTHER INFORMATION: Clone 16 LCDR2

<400> SEQUENCE: 108

Ala Val Ser Asn Leu Ala Ser
1               5


<210> SEQ ID NO 109
<211> LENGTH: 13
<212> TYPE: PRT
<213> ORGANISM: Artificial Sequence
<220> FEATURE:
<223> OTHER INFORMATION: Clone 16 LCDR3

<400> SEQUENCE: 109

Leu Gly Glu Phe Tyr Cys Ser Ser Ile Asp Cys Asn Ala
1               5                   10


<210> SEQ ID NO 110
<211> LENGTH: 5
<212> TYPE: PRT
<213> ORGANISM: Artificial Sequence
<220> FEATURE:
<223> OTHER INFORMATION: Clone 17 HCDR1

<400> SEQUENCE: 110

Ile Tyr Ala Met Gly
1               5


<210> SEQ ID NO 111
<211> LENGTH: 16
<212> TYPE: PRT
<213> ORGANISM: Artificial Sequence
<220> FEATURE:
<223> OTHER INFORMATION: Clone 17 HCDR2

<400> SEQUENCE: 111
```

```
Cys Ile Asp Arg Arg Gly Ala Thr Phe Tyr Ala Thr Trp Ala Lys Gly
1               5                   10                  15


<210> SEQ ID NO 112
<211> LENGTH: 7
<212> TYPE: PRT
<213> ORGANISM: Artificial Sequence
<220> FEATURE:
<223> OTHER INFORMATION: Clone 17 HCDR3

<400> SEQUENCE: 112

Asp Ser Gly Ala Phe Asp Pro
1               5


<210> SEQ ID NO 113
<211> LENGTH: 12
<212> TYPE: PRT
<213> ORGANISM: Artificial Sequence
<220> FEATURE:
<223> OTHER INFORMATION: Clone 17 LCDR1

<400> SEQUENCE: 113

Gln Ala Ser Gln Ser Val Tyr Asp Asn Asn Leu Ala
1               5                   10


<210> SEQ ID NO 114
<211> LENGTH: 7
<212> TYPE: PRT
<213> ORGANISM: Artificial Sequence
<220> FEATURE:
<223> OTHER INFORMATION: Clone 17 LCDR2

<400> SEQUENCE: 114

Ala Ala Ser Asn Leu Ala Ser
1               5


<210> SEQ ID NO 115
<211> LENGTH: 13
<212> TYPE: PRT
<213> ORGANISM: Artificial Sequence
<220> FEATURE:
<223> OTHER INFORMATION: Clone 17 LCDR3

<400> SEQUENCE: 115

Leu Gly Glu Phe Ser Cys Thr Thr Thr Asp Cys Asn Val
1               5                   10


<210> SEQ ID NO 116
<211> LENGTH: 131
<212> TYPE: PRT
<213> ORGANISM: Artificial Sequence
<220> FEATURE:
<223> OTHER INFORMATION: Clone 1 VH sequence

<400> SEQUENCE: 116

Leu Lys Gly Val Gln Cys Gln Ser Val Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Asn Ala Met Ile Trp Val Arg Gln Ala Pro Gly Lys
        35                  40                  45

Gly Leu Glu Tyr Ile Gly Asn Ile Gly Thr His Gly Thr Thr Tyr Tyr
    50                  55                  60

Ala Ser Trp Ala Lys Gly Arg Phe Thr Ile Ser Lys Thr Ser Thr Thr
65                  70                  75                  80
```

```
Val Asp Leu Lys Met Thr Ser Pro Thr Thr Glu Asp Thr Ala Thr Tyr
                85                  90                  95

Phe Cys Ser Arg Gly Asp Ile Trp Gly Pro Gly Thr Leu Val Thr Val
            100                 105                 110

Ser Leu Gly Gln Pro Lys Ala Pro Ser Val Phe Pro Leu Ala Pro Cys
        115                 120                 125

Cys Gly Asp
    130


<210> SEQ ID NO 117
<211> LENGTH: 126
<212> TYPE: PRT
<213> ORGANISM: Artificial Sequence
<220> FEATURE:
<223> OTHER INFORMATION: Clone 1 VL sequence

<400> SEQUENCE: 117

Trp Leu Pro Gly Ala Thr Phe Ala Gln Val Leu Thr Gln Thr Glu Ser
1               5                   10                  15

Pro Val Ser Ala Pro Leu Arg Gly Thr Val Thr Ile Asn Cys Gln Ala
            20                  25                  30

Ser Gln Ser Val Asp Asp Asn Asn Asn Leu Ala Trp Tyr Gln Gln Lys
        35                  40                  45

Pro Gly Gln Pro Pro Lys Leu Leu Ile Tyr Glu Ala Ser Thr Leu Ala
    50                  55                  60

Ser Gly Val Ser Ser Arg Phe Lys Gly Ser Gly Ser Gly Thr Gln Phe
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Ser Ser Ala Asp Cys Val Val Phe Gly
            100                 105                 110

Gly Gly Thr Glu Val Val Val Lys Gly Asp Pro Val Ala Pro
        115                 120                 125


<210> SEQ ID NO 118
<211> LENGTH: 135
<212> TYPE: PRT
<213> ORGANISM: Artificial Sequence
<220> FEATURE:
<223> OTHER INFORMATION: Clone 2 VH sequence

<400> SEQUENCE: 118

Leu Lys Gly Val Gln Cys Gln Ser Val Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Tyr Ala Met Ala Trp Val Arg Gln Ala Pro Gly Lys
        35                  40                  45

Gly Leu Glu Trp Ile Gly Cys Ile Asp Arg Arg Gly Gly Thr Phe Tyr
    50                  55                  60

Ala Ser Trp Val Lys Gly Arg Phe Thr Ile Ser Lys Thr Ser Thr Thr
65                  70                  75                  80

Val Asp Leu Lys Met Thr Ser Leu Thr Thr Glu Asp Thr Ala Thr Tyr
                85                  90                  95

Phe Cys Ala Arg Asp Ser Gly Ala Phe Asp Pro Trp Gly Pro Gly Thr
            100                 105                 110

Leu Val Thr Val Ser Ser Gly Gln Pro Lys Ala Pro Ser Val Phe Pro
```

```
        115                 120                 125

Leu Ala Pro Cys Cys Gly Asp
    130                 135


<210> SEQ ID NO 119
<211> LENGTH: 126
<212> TYPE: PRT
<213> ORGANISM: Artificial Sequence
<220> FEATURE:
<223> OTHER INFORMATION: Clone 2 VL sequence

<400> SEQUENCE: 119

Trp Leu Pro Gly Ala Thr Phe Ala Gln Ile Val Met Thr Gln Thr Pro
1               5                   10                  15

Ser Ser Val Ser Ala Ala Val Gly Gly Thr Val Thr Ile Lys Cys Gln
            20                  25                  30

Ala Ser Gln Ser Val Tyr Asp Asn Tyr Leu Ala Trp Tyr Gln Gln Lys
        35                  40                  45

Pro Gly Gln Pro Pro Lys Leu Leu Ile His Ala Ala Ser Asn Leu Ala
    50                  55                  60

Ser Arg Val Pro Ser Arg Phe Lys Gly Ser Gly Ser Gly Thr Gln Phe
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Thr Thr Thr Asp Cys Asn Val Phe Gly
            100                 105                 110

Gly Gly Thr Glu Val Val Val Lys Gly Asp Pro Val Ala Pro
        115                 120                 125


<210> SEQ ID NO 120
<211> LENGTH: 135
<212> TYPE: PRT
<213> ORGANISM: Artificial Sequence
<220> FEATURE:
<223> OTHER INFORMATION: Clone 3 VH sequence

<400> SEQUENCE: 120

Leu Lys Gly Val Gln Cys Gln Ser Leu Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Tyr Ala Val Gly Trp Val Arg Gln Ala Pro Gly Lys
        35                  40                  45

Gly Leu Glu Trp Ile Gly Cys Ile Asp Ser His Asp Asn Thr Phe Tyr
    50                  55                  60

Ala Ser Trp Ala Lys Ser Arg Phe Thr Ile Ser Lys Thr Ser Thr Thr
65                  70                  75                  80

Val Asp Leu Lys Ile Thr Ser Pro Thr Thr Glu Asp Thr Ala Thr Tyr
                85                  90                  95

Phe Cys Ala Arg Asp Ser Gly Ala Phe Asn Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 121
<211> LENGTH: 125
```

<212> TYPE: PRT
<213> ORGANISM: Artificial Sequence
<220> FEATURE:
<223> OTHER INFORMATION: Clone 3 VL sequence

<400> SEQUENCE: 121

```
Trp Leu Pro Gly Ala Thr Phe Ala Arg Val Leu Thr Gln Thr Pro Ser
1               5                   10                  15

Pro Val Ser Ala Ala Val Gly Gly Thr Val Thr Ile Asn Cys Gln Ala
            20                  25                  30

Ser Gln Ser Val Tyr Asp Asn Tyr Leu Ser Trp Tyr Gln Gln Lys Pro
        35                  40                  45

Gly Gln Pro Pro Lys Leu Leu Ile His Ala Val Ser Asn Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Gln Cys Asp Asp Ala Ala Thr Tyr Tyr Cys
                85                  90                  95

Leu Gly Glu Phe Tyr Cys Ser Ser Ile Asp Cys Asn Ala Phe Gly Gly
            100                 105                 110

Gly Thr Glu Val Val Val Lys Gly Asp Pro Val Ala Pro
        115                 120                 125
```

<210> SEQ ID NO 122
<211> LENGTH: 135
<212> TYPE: PRT
<213> ORGANISM: Artificial Sequence
<220> FEATURE:
<223> OTHER INFORMATION: Clone 4 VH sequence

<400> SEQUENCE: 122

```
Leu Lys Gly Val Gln Cys Gln Ser Leu Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Tyr Ala Val Gly Trp Val Arg Gln Ala Pro Gly Lys
        35                  40                  45

Gly Leu Glu Trp Ile Gly Cys Ile Asp Gly Arg Asp Ser Ala Phe Tyr
    50                  55                  60

Ala Ser Trp Ala Lys Gly Arg Phe Thr Ile Ser Lys Thr Ser Thr Thr
65                  70                  75                  80

Val Asp Leu Lys Ile Thr Ser Pro Thr Thr Glu Asp Thr Ala Thr Tyr
                85                  90                  95

Phe Cys Ala Arg Asp Ser Gly Ala Phe Asn Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135
```

<210> SEQ ID NO 123
<211> LENGTH: 125
<212> TYPE: PRT
<213> ORGANISM: Artificial Sequence
<220> FEATURE:
<223> OTHER INFORMATION: Clone 4 VL sequence

<400> SEQUENCE: 123

```
Trp Leu Pro Gly Ala Thr Phe Ala Arg Val Leu Thr Gln Thr Pro Ser
```

```
1               5                   10                  15

Pro Val Ser Ala Ala Val Gly Gly Thr Val Thr Ile Asn Cys Gln Ala
            20                  25                  30

Ser Gln Ser Val Tyr Asp Asn Tyr Leu Ser Trp Tyr Gln Gln Lys Pro
        35                  40                  45

Gly Gln Pro Pro Lys Leu Leu Ile His Ala Val Ser Asn Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Gln Cys Asp Asp Ala Ala Thr Tyr Ser Cys
                85                  90                  95

Leu Gly Glu Phe Tyr Cys Ser Ser Ile Asp Cys Asn Ala Phe Gly Gly
            100                 105                 110

Gly Thr Glu Val Val Val Lys Gly Asp Pro Val Ala Pro
        115                 120                 125


<210> SEQ ID NO 124
<211> LENGTH: 135
<212> TYPE: PRT
<213> ORGANISM: Artificial Sequence
<220> FEATURE:
<223> OTHER INFORMATION: Clone 5 VH sequence

<400> SEQUENCE: 124

Leu Lys Gly Val Gln Cys Gln Ser Val Glu Glu Ser Gly Gly Arg Leu
1               5                   10                  15

Val Thr Pro Gly Thr Pro Leu Thr Leu Thr Cys Thr Ala Ser Gly Ile
            20                  25                  30

Asp Leu Ser Thr Tyr Ala Met Ala Trp Val Arg Gln Ala Pro Gly Lys
        35                  40                  45

Gly Leu Glu Trp Ile Gly Cys Ile Asp Arg Arg Gly Gly Thr Phe Tyr
    50                  55                  60

Ala Ser Trp Ala Lys Gly Arg Phe Thr Ile Ser Lys Thr Ser Thr Thr
65                  70                  75                  80

Val Asp Leu Lys Met Thr Ser Leu Thr Thr Glu Asp Thr Ala Thr Tyr
                85                  90                  95

Phe Cys Ala Arg Asp Ser Gly Ala Phe Asp Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 125
<211> LENGTH: 126
<212> TYPE: PRT
<213> ORGANISM: Artificial Sequence
<220> FEATURE:
<223> OTHER INFORMATION: Clone 5 VL sequence

<400> SEQUENCE: 125

Trp Leu Pro Gly Ala Thr Phe Ala Gln Ile Val Met Thr Gln Thr Pro
1               5                   10                  15

Ser Pro Val Ser Val Ala Val Gly Gly Thr Val Thr Ile Lys Cys Gln
            20                  25                  30

Ala Ser Gln Ser Val Tyr Asp Asn Tyr Leu Ala Trp Tyr Gln Gln Lys
        35                  40                  45
```

```
Pro Gly Gln Pro Pro Lys Leu Leu Ile His Ala Ala Ser Asn Leu Ala
    50                  55                  60

Ser Gly Val Pro Ser Arg Phe Lys Gly Ser Gly Ser Gly Thr Glu Phe
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Thr Thr Thr Asp Cys Asn Val Phe Gly
            100                 105                 110

Gly Gly Thr Glu Val Val Val Lys Gly Asp Pro Val Ala Pro
        115                 120                 125


<210> SEQ ID NO 126
<211> LENGTH: 131
<212> TYPE: PRT
<213> ORGANISM: Artificial Sequence
<220> FEATURE:
<223> OTHER INFORMATION: Clone 6 VH sequence

<400> SEQUENCE: 126

Leu Lys Gly Val Gln Cys Gln Ser Val Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Asn Lys Asn Ala Met Ile Trp Val Arg Gln Ala Pro Gly Lys
        35                  40                  45

Gly Leu Glu Tyr Ile Gly Asn Ile Gly Thr Arg Gly Thr Thr Tyr Tyr
    50                  55                  60

Ala Ser Trp Thr Lys Gly Arg Phe Thr Ile Ser Arg Thr Ser Thr Thr
65                  70                  75                  80

Val Asp Leu Lys Met Thr Ser Pro Thr Thr Glu Asp Thr Ala Thr Tyr
                85                  90                  95

Phe Cys Thr Arg Gly Asp Ile Trp Gly Pro Gly Thr Leu Val Thr Val
            100                 105                 110

Ser Leu Gly Gln Pro Lys Ala Pro Ser Val Phe Pro Leu Ala Pro Cys
        115                 120                 125

Cys Gly Asp
    130


<210> SEQ ID NO 127
<211> LENGTH: 125
<212> TYPE: PRT
<213> ORGANISM: Artificial Sequence
<220> FEATURE:
<223> OTHER INFORMATION: Clone 6 VL sequence

<400> SEQUENCE: 127

Trp Leu Pro Gly Ala Thr Phe Ala Gln Val Leu Thr Gln Thr Pro Ser
1               5                   10                  15

Pro Val Ser Ala Pro Leu Gly Gly Thr Val Thr Ile Asn Cys Gln Ser
            20                  25                  30

Ser Gln Ser Val Asn Asn Asn Asp Leu Ala Trp Tyr Gln Gln Lys Pro
        35                  40                  45

Gly Gln Arg Pro Lys Val Leu Ile Tyr Glu Ala Ser Thr Leu Ala Ser
    50                  55                  60

Gly Val Ser Ser Arg Phe Lys Gly Ser Gly Ser Gly Thr Gln Phe Thr
65                  70                  75                  80

Leu Thr Ile Ser Asp Val Gln Cys Asp Asp Ala Ala Thr Tyr Tyr Cys
                85                  90                  95
```

```
Leu Gly Glu Phe Ser Cys Ser Ser Ala Asp Cys Val Ala Phe Gly Gly
            100                 105                 110

Gly Thr Glu Leu Val Val Lys Gly Asp Pro Val Ala Pro
        115                 120                 125


<210> SEQ ID NO 128
<211> LENGTH: 135
<212> TYPE: PRT
<213> ORGANISM: Artificial Sequence
<220> FEATURE:
<223> OTHER INFORMATION: Clone 7 VH sequence

<400> SEQUENCE: 128

Leu Lys Gly Val Gln Cys Gln Ser Val Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Tyr Ala Met Ser Trp Val Arg Gln Ala Pro Gly Lys
        35                  40                  45

Gly Leu Glu Trp Ile Gly Cys Ile Asp Ser Arg Gly Ser Val Tyr Tyr
    50                  55                  60

Ala Ser Trp Ala Lys Gly Arg Phe Thr Ile Ser Lys Thr Ser Thr Thr
65                  70                  75                  80

Val Asp Leu Lys Val Thr Ser Pro Thr Thr Glu Asp Thr Ala Thr Tyr
                85                  90                  95

Phe Cys Ala Arg Asp Ser Gly Ala Phe Asp Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 129
<211> LENGTH: 125
<212> TYPE: PRT
<213> ORGANISM: Artificial Sequence
<220> FEATURE:
<223> OTHER INFORMATION: Clone 7 VL sequence

<400> SEQUENCE: 129

Ala Pro Ser Ala Thr Phe Ala Gln Ile Val Met Thr Gln Thr Pro Ala
1               5                   10                  15

Ser Val Ser Ala Ala Val Gly Gly Thr Val Thr Ile Ser Cys Gln Ala
            20                  25                  30

Ser Gln Ser Val Tyr Asp Asn Tyr Leu Ser Trp Tyr Gln Gln Lys Pro
        35                  40                  45

Gly Gln Pro Pro Lys Leu Leu Ile Val Ala Ala Ser Asn Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Gln Cys Asp Asp Ala Ala Thr Tyr Tyr Cys
                85                  90                  95

Leu Gly Glu Phe Tyr Cys Ser Ser Met Asp Cys Asn Ala Phe Gly Gly
            100                 105                 110

Gly Thr Glu Val Val Val Lys Gly Asp Pro Val Ala Pro
        115                 120                 125
```

```
<210> SEQ ID NO 130
<211> LENGTH: 135
<212> TYPE: PRT
<213> ORGANISM: Artificial Sequence
<220> FEATURE:
<223> OTHER INFORMATION: Clone 8 VH sequence

<400> SEQUENCE: 130

Ala Val Leu Lys Gly Val Gln Cys Gln Ser Met Glu Glu Ser Gly Gly
1               5                   10                  15

Arg Leu Val Thr Pro Gly Thr Pro Leu Thr Leu Thr Cys Thr Val Ser
            20                  25                  30

Gly Ile Asp Leu Ser Ser Asn Ala Met Ile Trp Val Arg Gln Ala Pro
        35                  40                  45

Gly Lys Gly Leu Glu Tyr Ile Gly Asn Ile Gly Thr His Gly Thr Thr
    50                  55                  60

Tyr Tyr Ala Ser Trp Ala Lys Gly Arg Phe Thr Ile Ser Lys Thr Ser
65                  70                  75                  80

Thr Thr Val Asp Leu Lys Met Thr Ser Pro Thr Thr Glu Asp Thr Ala
                85                  90                  95

Thr Tyr Phe Cys Ser Arg Gly Asp Ile Trp Gly Pro Gly Thr Leu Val
            100                 105                 110

Thr Val Ser Leu Gly Gln Pro Lys Ala Pro Ser Val Phe Pro Leu Ala
        115                 120                 125

Pro Cys Cys Gly Asp Thr Pro
    130                 135


<210> SEQ ID NO 131
<211> LENGTH: 126
<212> TYPE: PRT
<213> ORGANISM: Artificial Sequence
<220> FEATURE:
<223> OTHER INFORMATION: Clone 8 VL sequence

<400> SEQUENCE: 131

Trp Leu Pro Gly Ala Thr Phe Ala Gln Val Leu Thr Gln Thr Pro Ser
1               5                   10                  15

Pro Val Ser Val Ala Val Gly Gly Thr Val Thr Ile Asn Cys Gln Ala
            20                  25                  30

Ser Gln Ser Val Asp Asn Asn Asn Asn Leu Ala Trp Tyr His Gln Lys
        35                  40                  45

Pro Gly Gln Pro Pro Lys Leu Leu Ile Tyr Glu Ala Ser Thr Leu Ala
    50                  55                  60

Ser Gly Val Ser Ser Arg Phe Lys Gly Ser Gly Ser Gly Thr Gln Phe
65                  70                  75                  80

Thr Leu Thr Ile Ser Gly Val Gln Cys Asp Asp Ala Ala Thr Tyr Tyr
                85                  90                  95

Cys Leu Gly Glu Phe Ser Cys Ser Ser Ala Asp Cys Val Ala Phe Gly
            100                 105                 110

Gly Gly Thr Glu Val Val Val Lys Gly Asp Pro Val Ala Pro
        115                 120                 125


<210> SEQ ID NO 132
<211> LENGTH: 135
<212> TYPE: PRT
<213> ORGANISM: Artificial Sequence
<220> FEATURE:
<223> OTHER INFORMATION: Clone 9 VH sequence

<400> SEQUENCE: 132
```

```
Leu Lys Gly Val Gln Cys Gln Ser Leu Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Tyr Ala Val Gly Trp Val Arg Gln Ala Pro Gly Lys
        35                  40                  45

Gly Leu Glu Trp Ile Gly Cys Ile Asp Ser His Asp Asn Thr Phe Tyr
    50                  55                  60

Ala Ser Trp Ala Lys Gly Arg Phe Thr Ile Ser Lys Thr Ser Thr Thr
65                  70                  75                  80

Val Asp Leu Lys Ile Thr Ser Pro Thr Thr Glu Asp Thr Ala Thr Tyr
                85                  90                  95

Phe Cys Ala Arg Asp Ser Gly Ala Phe Asn Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 133
<211> LENGTH: 125
<212> TYPE: PRT
<213> ORGANISM: Artificial Sequence
<220> FEATURE:
<223> OTHER INFORMATION: Clone 9 VL sequence

<400> SEQUENCE: 133

Trp Leu Pro Gly Ala Thr Phe Ala Arg Val Leu Thr Gln Thr Pro Ser
1               5                   10                  15

Pro Val Ser Ala Ala Val Gly Gly Thr Val Thr Ile Asn Cys Gln Ala
            20                  25                  30

Ser Gln Ser Val Tyr Asp Asn Tyr Leu Ser Trp Tyr Gln Gln Lys Pro
        35                  40                  45

Gly Gln Pro Pro Lys Leu Leu Ile His Ala Val Ser Asn Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Gln Cys Asp Asp Ala Ala Thr Tyr Tyr Cys
                85                  90                  95

Leu Gly Glu Phe Tyr Cys Ser Ser Ile Asp Cys Asn Ala Phe Gly Gly
            100                 105                 110

Gly Thr Glu Val Val Val Lys Gly Asp Pro Val Ala Pro
        115                 120                 125


<210> SEQ ID NO 134
<211> LENGTH: 131
<212> TYPE: PRT
<213> ORGANISM: Artificial Sequence
<220> FEATURE:
<223> OTHER INFORMATION: Clone 10 VH sequence

<400> SEQUENCE: 134

Leu Lys Gly Val Gln Cys Gln Ser Val Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Asn Ala Met Ile Trp Val Arg Gln Ala Pro Gly Lys
```

```
        35                  40                  45

Gly Leu Glu Tyr Ile Gly Asn Ile Gly Thr His Gly Thr Thr Tyr Tyr
    50                  55                  60

Ala Ser Trp Ser Lys Gly Arg Phe Thr Ile Ser Lys Thr Ser Thr Thr
65                  70                  75                  80

Val Asp Leu Lys Met Thr Ser Pro Thr Thr Glu Asp Thr Ala Thr Tyr
                85                  90                  95

Phe Cys Ser Arg Gly Asp Ile Trp Gly Pro Gly Thr Leu Val Thr Val
            100                 105                 110

Ser Leu Gly Gln Pro Lys Ala Pro Ser Val Phe Pro Leu Ala Pro Cys
        115                 120                 125

Cys Gly Asp
    130


<210> SEQ ID NO 135
<211> LENGTH: 126
<212> TYPE: PRT
<213> ORGANISM: Artificial Sequence
<220> FEATURE:
<223> OTHER INFORMATION: Clone 10 VL sequence

<400> SEQUENCE: 135

Trp Leu Pro Gly Ala Thr Phe Ala Gln Val Leu Thr Gln Thr Ala Ser
1               5                   10                  15

Pro Val Ser Ala Ala Val Gly Gly Thr Val Thr Ile Tyr Cys Gln Ala
            20                  25                  30

Ser Gln Ser Val Asp Asn Asn Asn Asn Leu Ala Trp Tyr Gln Gln Lys
        35                  40                  45

Pro Gly Gln Pro Pro Lys Leu Leu Ile Tyr Glu Ala Ser Thr Leu Ala
    50                  55                  60

Ser Gly Val Ser Ser Arg Phe Lys Gly Ser Gly Ser Gly Thr Gln Phe
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Ser Ser Ala Asp Cys Val Ala Phe Gly
            100                 105                 110

Gly Gly Thr Glu Met Val Val Lys Gly Asp Pro Val Ala Pro
        115                 120                 125


<210> SEQ ID NO 136
<211> LENGTH: 135
<212> TYPE: PRT
<213> ORGANISM: Artificial Sequence
<220> FEATURE:
<223> OTHER INFORMATION: Clone 11 VH sequence

<400> SEQUENCE: 136

Leu Lys Gly Val Gln Cys Gln Ser Val Glu Glu Ser Gly Gly Arg Leu
1               5                   10                  15

Val Pro Pro Gly Thr Pro Leu Thr Leu Thr Cys Thr Val Ser Gly Ile
            20                  25                  30

Asp Leu Asn Asn Tyr Ala Met Ala Trp Val Arg Gln Ala Pro Gly Lys
        35                  40                  45

Gly Leu Glu Trp Ile Gly Cys Ile Asp Arg Arg Gly Gly Thr Phe Tyr
    50                  55                  60

Ala Ser Trp Ala Lys Gly Arg Phe Thr Ile Ser Lys Thr Ser Thr Thr
65                  70                  75                  80
```

```
Val Asp Leu Lys Met Thr Ser Leu Thr Thr Glu Asp Thr Ala Thr Tyr
                85                  90                  95

Phe Cys Ala Arg Asp Ser Gly Ala Phe Asp Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 137
<211> LENGTH: 126
<212> TYPE: PRT
<213> ORGANISM: Artificial Sequence
<220> FEATURE:
<223> OTHER INFORMATION: Clone 11 VL sequence

<400> SEQUENCE: 137

Trp Leu Pro Gly Ala Thr Phe Ala Gln Ile Val Met Thr Gln Thr Pro
1               5                   10                  15

Ser Pro Val Ser Val Ala Val Gly Gly Thr Val Thr Ile Lys Cys Gln
            20                  25                  30

Ala Ser Gln Ser Val Tyr Asp Asn Tyr Leu Ala Trp Tyr Gln Gln Lys
        35                  40                  45

Pro Gly Gln Pro Pro Lys Leu Leu Ile His Ala Ala Ser Asn Leu Ala
    50                  55                  60

Ser Arg Val Pro Ser Arg Phe Lys Gly Ser Gly Ser Gly Thr Gln Phe
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Thr Thr Thr Asp Cys Asn Val Phe Gly
            100                 105                 110

Gly Gly Thr Glu Val Val Val Lys Gly Asp Pro Val Ala Pro
        115                 120                 125


<210> SEQ ID NO 138
<211> LENGTH: 135
<212> TYPE: PRT
<213> ORGANISM: Artificial Sequence
<220> FEATURE:
<223> OTHER INFORMATION: Clone 12 VH sequence

<400> SEQUENCE: 138

Leu Lys Gly Val Gln Cys Gln Ser Leu Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Tyr Ala Val Gly Trp Val Arg Gln Ala Pro Gly Lys
        35                  40                  45

Gly Leu Glu Trp Ile Gly Cys Ile Asp Ser His Asp Asn Thr Phe Tyr
    50                  55                  60

Ala Ser Trp Ala Lys Ser Arg Phe Thr Ile Ser Lys Thr Ser Thr Thr
65                  70                  75                  80

Val Asp Leu Lys Ile Thr Ser Pro Thr Thr Glu Asp Thr Ala Thr Tyr
                85                  90                  95

Phe Cys Ala Arg Asp Ser Gly Ala Phe Asn Pro Trp Gly Pro Gly Thr
            100                 105                 110

Leu Val Thr Val Ser Ser Gly Gln Pro Lys Ala Pro Ser Val Phe Pro
        115                 120                 125
```

```
Leu Ala Pro Cys Cys Gly Asp
    130                 135


<210> SEQ ID NO 139
<211> LENGTH: 125
<212> TYPE: PRT
<213> ORGANISM: Artificial Sequence
<220> FEATURE:
<223> OTHER INFORMATION: Clone 12 VL sequence

<400> SEQUENCE: 139

Trp Leu Pro Gly Ala Thr Phe Ala Arg Val Leu Thr Gln Thr Pro Ser
1               5                   10                  15

Pro Val Ser Ala Ala Val Gly Gly Thr Val Thr Ile Asn Cys Gln Ala
            20                  25                  30

Ser Gln Ser Val Tyr Asp Asn Tyr Leu Ser Trp Tyr Gln Gln Lys Pro
        35                  40                  45

Gly Gln Pro Pro Lys Leu Leu Ile His Ala Val Ser Asn Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Gln Cys Asp Asp Ala Ala Thr Tyr Tyr Cys
                85                  90                  95

Leu Gly Glu Phe Tyr Cys Ser Ser Ile Asp Cys Asn Ala Phe Gly Gly
            100                 105                 110

Gly Thr Glu Val Val Val Lys Gly Asp Pro Val Ala Pro
        115                 120                 125


<210> SEQ ID NO 140
<211> LENGTH: 135
<212> TYPE: PRT
<213> ORGANISM: Artificial Sequence
<220> FEATURE:
<223> OTHER INFORMATION: Clone 13 VH sequence

<400> SEQUENCE: 140

Leu Lys Gly Val Gln Cys Gln Ser Leu Glu Glu Ser Gly Gly Arg Leu
1               5                   10                  15

Val Thr Pro Gly Gly Ser Leu Thr Leu Thr Cys Thr Val Ser Gly Ile
            20                  25                  30

Asp Leu Ser Ser Tyr Ala Met Gly Trp Val Arg Gln Ala Pro Gly Lys
        35                  40                  45

Gly Leu Glu Trp Ile Gly Cys Ile Asp Arg Arg Gly Ala Thr Phe Tyr
    50                  55                  60

Ala Ser Trp Ala Lys Gly Arg Phe Thr Ile Ser Lys Thr Ser Thr Thr
65                  70                  75                  80

Val Asp Leu Lys Met Thr Ser Leu Thr Thr Glu Asp Thr Ala Thr Tyr
                85                  90                  95

Phe Cys Ala Arg Asp Ser Gly Ala Phe Asp Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 141
<211> LENGTH: 126
<212> TYPE: PRT
```

```
<213> ORGANISM: Artificial Sequence
<220> FEATURE:
<223> OTHER INFORMATION: Clone 13 VL sequence

<400> SEQUENCE: 141

Trp Leu Pro Gly Ala Thr Phe Ala Gln Ile Val Met Thr Gln Thr Pro
1               5                   10                  15

Ser Pro Val Ser Ala Ala Val Gly Gly Thr Val Thr Ile Lys Cys Gln
            20                  25                  30

Ala Ser Gln Ser Val Tyr Asp Asn Tyr Leu Ser Trp Tyr His Gln Lys
        35                  40                  45

Pro Gly Gln Pro Pro Lys Leu Leu Ile His Ala Ala Ser Asn Leu Ala
    50                  55                  60

Ser Arg Val Pro Ser Arg Phe Lys Gly Ser Gly Ser Gly Thr Gln Phe
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Thr Thr Thr Asp Cys Asn Val Phe Gly
            100                 105                 110

Gly Gly Thr Glu Val Val Val Lys Gly Asp Pro Val Ala Pro
        115                 120                 125


<210> SEQ ID NO 142
<211> LENGTH: 135
<212> TYPE: PRT
<213> ORGANISM: Artificial Sequence
<220> FEATURE:
<223> OTHER INFORMATION: Clone 14 VH sequence

<400> SEQUENCE: 142

Leu Lys Gly Val Gln Cys Gln Ser Val Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Asn Ser Tyr Ala Met Gly Trp Val Arg Gln Ala Pro Gly Lys
        35                  40                  45

Gly Leu Glu Trp Ile Gly Cys Ile Asp Arg Arg Gly Gly Thr Phe Tyr
    50                  55                  60

Ala Ser Trp Ala Lys Gly Arg Phe Thr Ile Ser Lys Thr Ser Thr Thr
65                  70                  75                  80

Val Asp Leu Lys Met Thr Ser Leu Thr Thr Glu Asp Thr Ala Thr Tyr
                85                  90                  95

Phe Cys Ala Arg Asp Ser Gly Ala Phe Asp Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 143
<211> LENGTH: 126
<212> TYPE: PRT
<213> ORGANISM: Artificial Sequence
<220> FEATURE:
<223> OTHER INFORMATION: Clone 14 VL sequence

<400> SEQUENCE: 143

Trp Leu Pro Gly Ala Thr Phe Ala Gln Ile Val Met Thr Gln Thr Pro
1               5                   10                  15
```

```
Ser Pro Val Ser Val Ala Val Gly Gly Thr Val Thr Ile Lys Cys Gln
            20                  25                  30

Ala Ser Gln Ser Val Tyr Asp Asn Tyr Leu Ala Trp Tyr Gln Gln Lys
        35                  40                  45

Pro Gly Gln Pro Pro Lys Leu Leu Ile His Ala Ala Ser Asn Leu Ala
    50                  55                  60

Ser Arg Val Pro Ser Arg Phe Lys Gly Ser Gly Ser Gly Thr Gln Phe
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Thr Thr Thr Asp Cys Asn Val Phe Gly
            100                 105                 110

Gly Gly Thr Glu Val Val Val Lys Gly Asp Pro Val Ala Pro
        115                 120                 125
```

<210> SEQ ID NO 144
<211> LENGTH: 119
<212> TYPE: PRT
<213> ORGANISM: Artificial Sequence
<220> FEATURE:
<223> OTHER INFORMATION: Clone 15 VH sequence

<400> SEQUENCE: 144

```
Gln Ser Val Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser Tyr Ala
            20                  25                  30

Met Thr Trp Val Arg Gln Ala Pro Gly Lys Gly Leu Glu Trp Ile Gly
        35                  40                  45

Cys Ile Asp Thr Gly Gly Ser Ala Tyr Tyr Ala Ser Trp Ala Lys Gly
    50                  55                  60

Arg Phe Thr Ile Ser Lys Thr Ser Thr Thr Val Ala Leu Lys Ile Thr
65                  70                  75                  80

Ser Pro Thr Thr Glu Asp Thr Ala Thr Tyr Phe Cys Ala Arg Asp Thr
                85                  90                  95

Gly Ala Phe Asp Pro Trp Gly Pro Gly Thr Leu Val Thr Val Ser Ser
            100                 105                 110

Gly Gln Pro Lys Ala Pro Ser
        115
```

<210> SEQ ID NO 145
<211> LENGTH: 126
<212> TYPE: PRT
<213> ORGANISM: Artificial Sequence
<220> FEATURE:
<223> OTHER INFORMATION: Clone 15 VL sequence

<400> SEQUENCE: 145

```
Trp Leu Pro Gly Ala Thr Phe Ala Gln Ile Val Met Thr Gln Thr Pro
1               5                   10                  15

Ala Ser Val Ser Val Ala Val Gly Gly Thr Val Thr Ile Asn Cys Gln
            20                  25                  30

Ala Ser Gln Ser Val Tyr Asp Asn Asn Leu Ala Trp Tyr Gln Gln Lys
        35                  40                  45

Pro Gly Gln Pro Pro Lys Leu Leu Ile Val Ala Ala Ser Asn Leu Pro
    50                  55                  60

Ser Gly Val Pro Ser Arg Phe Lys Gly Ser Gly Ser Gly Thr Gln Phe
```

```
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Ser Ser Thr Asp Cys Asn Ala Phe Gly
            100                 105                 110

Gly Gly Thr Glu Val Val Gly Lys Gly Asp Pro Val Ala Pro
        115                 120                 125


<210> SEQ ID NO 146
<211> LENGTH: 135
<212> TYPE: PRT
<213> ORGANISM: Artificial Sequence
<220> FEATURE:
<223> OTHER INFORMATION: Clone 16 VH sequence

<400> SEQUENCE: 146

Leu Lys Gly Val Gln Cys Gln Ser Leu Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ser Tyr Ala Val Gly Trp Val Arg Gln Ala Pro Gly Lys
        35                  40                  45

Gly Leu Glu Trp Ile Gly Cys Ile Asp Ser Arg Asp Ser Ala Phe Tyr
    50                  55                  60

Ala Ser Trp Ala Lys Gly Arg Phe Thr Ile Ser Lys Thr Ser Thr Thr
65                  70                  75                  80

Val Asp Leu Lys Ile Thr Ser Pro Thr Thr Glu Asp Thr Ala Thr Tyr
                85                  90                  95

Phe Cys Ala Arg Asp Ser Gly Ala Phe Asn Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 147
<211> LENGTH: 125
<212> TYPE: PRT
<213> ORGANISM: Artificial Sequence
<220> FEATURE:
<223> OTHER INFORMATION: Clone 16 VL sequence

<400> SEQUENCE: 147

Trp Leu Pro Gly Ala Thr Phe Ala Arg Val Leu Thr Gln Thr Pro Ser
1               5                   10                  15

Pro Val Ser Ala Val Val Gly Gly Thr Val Thr Ile Asn Cys Gln Ala
            20                  25                  30

Ser Gln Ser Val Tyr Asp Asn Tyr Leu Ser Trp Tyr Gln Gln Lys Pro
        35                  40                  45

Gly Gln Pro Pro Lys Leu Leu Ile His Ala Val Ser Asn Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Gln Cys Asp Asp Ala Ala Thr Tyr Tyr Cys
                85                  90                  95

Leu Gly Glu Phe Tyr Cys Ser Ser Ile Asp Cys Asn Ala Phe Gly Gly
            100                 105                 110
```

```
Gly Thr Glu Val Val Val Lys Gly Asp Pro Val Ala Pro
        115                 120                 125


<210> SEQ ID NO 148
<211> LENGTH: 135
<212> TYPE: PRT
<213> ORGANISM: Artificial Sequence
<220> FEATURE:
<223> OTHER INFORMATION: Clone 17 VH sequence

<400> SEQUENCE: 148

Leu Lys Gly Val Gln Cys Gln Ser Val Glu Glu Ser Gly Gly Arg Leu
1               5                   10                  15

Val Thr Pro Gly Thr Pro Leu Thr Leu Thr Cys Thr Val Ser Gly Ile
            20                  25                  30

Asp Leu Ser Ile Tyr Ala Met Gly Trp Val Arg Gln Ala Pro Gly Lys
        35                  40                  45

Gly Leu Glu Trp Ile Gly Cys Ile Asp Arg Arg Gly Ala Thr Phe Tyr
    50                  55                  60

Ala Thr Trp Ala Lys Gly Arg Phe Thr Ile Ser Lys Thr Ser Thr Thr
65                  70                  75                  80

Val Asp Leu Lys Leu Thr Ser Leu Thr Thr Glu Asp Thr Ala Thr Tyr
                85                  90                  95

Phe Cys Ala Arg Asp Ser Gly Ala Phe Asp Pro Trp Gly Pro Gly Thr
            100                 105                 110

Leu Val Thr Val Ser Ser Gly Gln Pro Lys Ala Pro Ser Val Phe Pro
        115                 120                 125

Leu Ala Pro Cys Cys Gly Asp
    130                 135


<210> SEQ ID NO 149
<211> LENGTH: 126
<212> TYPE: PRT
<213> ORGANISM: Artificial Sequence
<220> FEATURE:
<223> OTHER INFORMATION: Clone 17 VL sequence

<400> SEQUENCE: 149

Trp Leu Pro Gly Ala Thr Phe Ala Gln Ile Val Met Thr Gln Thr Pro
1               5                   10                  15

Ser Pro Val Ser Ala Ala Val Gly Gly Thr Val Thr Ile Lys Cys Gln
            20                  25                  30

Ala Ser Gln Ser Val Tyr Asp Asn Asn Leu Ala Trp Tyr Gln Gln Lys
        35                  40                  45

Pro Gly Gln Pro Pro Lys Leu Leu Ile His Ala Ala Ser Asn Leu Ala
    50                  55                  60

Ser Arg Val Pro Ser Arg Phe Ser Gly Ser Gly Ser Gly Thr Gln Phe
65                  70                  75                  80

Thr Leu Thr Ile Ser Asp Val Gln Cys Asp Asp Ala Ala Thr Tyr Tyr
                85                  90                  95

Cys Leu Gly Glu Phe Ser Cys Thr Thr Thr Asp Cys Asn Val Phe Gly
            100                 105                 110

Gly Gly Thr Glu Val Val Val Lys Gly Asp Pro Val Ala Pro
        115                 120                 125


<210> SEQ ID NO 150
<211> LENGTH: 7
<212> TYPE: PRT
<213> ORGANISM: Artificial Sequence
```

-continued

```
<220> FEATURE:
<223> OTHER INFORMATION: Residues 373 to 379 of human 2N4R (amino acids
      1-441) tau (SEQ ID NO: 2)

<400> SEQUENCE: 150

Thr His Lys Leu Thr Phe Arg
1               5
```

TAU EPITOPE AND BINDING MOLECULES

SEQUENCE LISTING

The instant application contains a Sequence Listing which has been submitted electronically in ASCII format via EFS-Web and hereby incorporated by reference in its entirety. Said ASCII copy, created on 5 Jul. 2022, is named 251128_GEN2BR001 US1_CorrSeqList_ST25.TXT and is 67,000 bytes in size.

FIELD OF THE INVENTION

The invention relates to novel tau epitopes and to binding molecules, such as antibodies, 10 capable of binding specifically to such epitopes. The invention relates to anti-tau binding molecules, such as antibodies, and compositions thereof, for use in the treatment or diagnosis of a tauopathy. The invention further relates to methods of treating a tauopathy, involving administering an anti-tau binding molecule, e.g., antibody.

BACKGROUND TO THE INVENTION

The microtubule-associated protein (MAP) tau plays a critical role in the pathogenesis of Alzheimer's disease (AD) and related tauopathies. Development of tau pathology is associated with progressive neuronal loss and cognitive decline. In patients with dementias that involve tau, including Alzheimer's disease (AD), tau pathology spreads through the brain in a predictable spatial order, which correlates with disease burden. Recent evidence suggests the involvement of extracellular tau species in the propagation between neurons of neurofibrillary lesions and the spread of tau toxicity throughout different brain regions. The mechanism underlying tau propagation is not fully characterised, but suggests a role for extracellular tau in both cognitive decline and in the spreading of tau pathology, through synaptic and non-synaptic mechanisms.

Tau proteins are produced by alternative splicing from a single gene, MAPT (microtubule-associated protein tau); in humans the MAPT gene is located on chromosome 17q21. Tau proteins are abundant in neurons of the central nervous system and are also expressed at very low levels in CNS astrocytes and oligodendrocytes. Within neurons, tau is found predominantly in axons as a highly soluble phosphoprotein. Tau is post-translationally modified, with both physiological and pathophysiological consequences. Acetylation, ubiquitination, O-linked N-acetylglucosamine modification, methylation and phosphorylation of tau have all been described to regulate the function of tau (Morris et al (2015) Nature Neuroscience 18:1183-1189). In addition, tau may be cleaved to form peptides with enhanced ability to form aggregates and/or with neurotoxic properties.

The microtubule-associated protein tau and its hype rphosphorylated version form the main constituent of intracellular neurofibrillary tangles, a hallmark of several dementias, including AD and frontotemporal dementia. This evidence forms the basis of a hypothesis for AD, wherein the intracellular accumulation of tau leads to microtubule disassembly, dendritic spinal collapse, and degeneration of axons; malfunction in communication between neurons and cell death. Accordingly, tau, particularly in phosphorylated form, has been the target for development of passive and active immunotherapies for AD and other tauopathies.

Immunotherapies in clinical development that target various epitopes of tau were summarized by Pedersen et al. (2015) Trends Mol Med 21(6): 394-402:

TABLE 1

Immunotherapies in clinical development

| Antibody program | Antibody | Species | Epitope | IP |
|---|---|---|---|---|
| ACImmune, Janssen, KU Leuven, and Fred van Leuven | ACI-35 | Active vaccine | pS396/pS404 peptide liposome formulation | WO2010115843 |
| ACImmune, Genentech, KU Leuven, and Fred van Leuven | hACI-36-2B6-Ab1 and hACI-36-3A8-Ab1 | Humanized mouse monoclonal | pS409 | WO2013151762 |
| Axon Neuroscience and Michal Novak | AADvac1 | Active vaccine | 294-305 peptide 294KDNIKHVPGGGS305 | WO02062851 |
| Axon Neuroscience and Michal Novak | DC8E8 | Humanized antibody | Generated from immunizations with 294-305 peptide | WO02062851 |
| Biogen Idec, Panima Pharmaceuticals AG, and Roger Nitsch | NI-105.4E4, 24B2, and 4A3 | Human autoantibodies | V339, E342, D387, E391, K395 | WO2012049570 US2012087861 |
| C2N Diagnostics, David Holtzman, and Marc Diamond | HJ9.3, HJ9.4, and HJ8.5 | Mouse monoclonal | 306-320, 7-13, and 25-30 | |

TABLE 1-continued

| Immunotherapies in clinical development | | | | |
|---|---|---|---|---|
| Antibody program | Antibody | Species | Epitope | IP |
| Eli Lilly and Peter Davies | PHF1, MC1 | Mouse monoclonal | pS396/pS404, conformational | WO9620218 |
| Hoffman-La Roche | 2.10.2, 2.20.4, and 5.6.11 MAb86 | Rabbit monoclonal | pS422 | WO2010142423 |
| iPierian/BMS | IPN001, IPN002, IPN007 | Humanized mouse monoclonal | 9-18 | US2014294831 |
| Intellect Neurosciences Inc. and Lester Binder | TOC-1 and TauC3 | Mouse monoclonal | Tau-dimers and caspase- cleaved Tau421 | US8697076 US2012244174 |
| Lundbeck, NYU, and Einar Sigurdsson | 4E6, 6B2, and scFv235 | Mouse monoclonal | pS396/pS404, total tau, other hyperphosphorylation, conformational, and truncation sites | US2008050383 US2010316564 |
| Pfizer | | Chicken monoclonal | pT212/pS214, pT231/pS235, and pS396/pS404 | WO2014016737 |
| Prothena Corporation, Lars Ittner, and Jurgen Gotz | pS404-Ab1/Ab2 pan-tau | Mouse monoclonal | pS404 and total tau | WO2014134685 |
| Prothena Corporation | h16B5 | Humanized mouse monoclonal | 23-46 peptide | WO2014165271 |
| Teijin Pharma Ltd and Hitoshi Mori | Ta1505 | Mouse monoclonal | pSer413 | WO2013180238 |

In addition to therapies listed in Table 1, Janssen are progressing antibodies specifically targeting pT217 (JNJ63733657) and UCB are in the clinic with antibodies targeting a mid-region tau sequence (amino acids 235-246 of 2N4R tau; UCB0107) (reviewed in Sandusky-Beltran et al., 2020, Neuropharmacol.175:108104). Eisai are also preparing for clinical trials with an antibody targeting sequences in the microtubule binding region (amino acids 299-303 and 362-366; E2814; Roberts et al., 2020, Acta Neuropathologica Comms 8:13).

U.S. Pat. No. 9,139,643B2 describes an antibody, specific for misfolded and/or aggregated tau protein that does not bind to normal tau protein and which binds an epitope within amino acid residues 379-408 of full length human 2N4R (amino acids 1-441) tau (SEQ ID NO:2), it is preferred that the tau protein is fully phosphorylated.

U.S. Pat. No. 9,777,056B2 describes an antibody, capable of binding specifically to a misfolded and/or aggregate form of tau protein, raised against a tau epitope within amino acid residues 379-408 that possesses phosphoserine residues at tau position 396 and at tau position 404.

WO2010144711 describes recombinantly-produced antibodies capable of preferentially binding to pathological tau protein, relative to normal tau protein, elicited by immunization with various isolated tau peptides including tau 379-408, SEQ ID NO: 57 of that specification, and tau 379-391, SEQ ID NO: 102 of that specification.

US 2017/0260263 A1 describes tau peptides comprising the "therapeutic epitope" Tau 361-THVPGGG-367 (SEQ ID NO: 101 of that specification).

US2004/0110250 A1 describes tau aggregation and regions important for the assembly of PHF tau. It does not mention tau uptake, or therapeutic antibodies. Tau 186-391 constructs are expressed intracellularly, proteolytically processed intracellularly and the resulting truncated peptides detected intracellularly. There is no discussion of extracellular forms of tau.

Recent studies suggest a toxic role for disease-specific tau species located in the brain extracellular space.

There is a need to identify novel therapeutic approaches intended to interfere early in the process of tau-mediated synaptic dysfunction and the propagation of tau pathology; accordingly, there is a need to identify epitopes of tau that occur specifically on extracellular pathological species of the tau protein and to generate therapeutic antibodies that seek to halt disease progression by binding specifically to extracellular pathological species of the tau protein. Such epitopes and molecules that bind thereto may also be useful for diagnosis of tauopathies.

STATEMENTS OF INVENTION

The invention provides:

1. An isolated synthetic or recombinant peptide comprising an epitope, the peptide consisting of residues 369-381 (SEQ ID NO: 1) of human 2N4R (amino acids 1-441) tau (SEQ ID NO: 2), wherein the epitope is comprised within residues 369-381 (SEQ ID NO: 1).
2. An isolated synthetic or recombinant peptide according to clause 1, further comprising an N-terminal cysteine residue (SEQ ID NO: 13) or C-terminal cysteine residue.
3. An isolated synthetic or recombinant peptide according to clause 1 or clause 2 comprising a carrier protein, preferably the carrier protein is selected from Keyhole limpet hemocyanin (KLH), Concholepas hemocyanin ("Blue Carrier"), Bovine serum albumin (BSA), Cationized BSA (cBSA) and Ovalbumin (OVA).

4. An isolated synthetic or recombinant peptide according to any one of clauses 1 to 3, comprising an epitope, wherein the epitope is formed by residues of the amino acid sequence 373 to 379 (THKLTFR, SEQ ID NO: 150) of human 2N4R (amino acids 1-441) tau (SEQ ID NO: 2).

5. An isolated synthetic or recombinant peptide according to any one of clauses 1 to 4, comprising an epitope formed by residues of the amino acid sequence 373 to 379 (THKLTFR, SEQ ID NO: 150) of human 2N4R (amino acids 1-441) tau (SEQ ID NO: 2), wherein the epitope comprises residues:

(a) L376 and F378, preferably comprising residues H374, K375, L376, F378, R379 or (b) K375, T377 and R379, preferably comprising residues T373, K375, T377 and R379.

6. A binding molecule capable of binding specifically to an isolated synthetic or recombinant peptide of any one of clauses 1 to 5 and/or capable of binding specifically to an epitope of any one of clauses 1 to 5.

7. A binding molecule of clause 6, wherein the binding molecule is an antigen-binding protein, such as an antibody or an antigen-binding fragment thereof, a domain antibody, a protein scaffold, an affimer, a bicyclic peptide or a peptide aptamer, or an oligonucleotide aptamer.

8. An antigen-binding protein, such as an antibody or antigen-binding fragment thereof, according to clause 6 or 7 comprising an antigen-binding site comprising the CDRs (HCDR1, HCRD2, HCDR3, LCDR1, LCDR2 and LCDR3, respectively) of antibody:

(a) Clone 1 of SEQ ID NO: 14, SEQ ID NO: 15, SEQ ID NO: 16, SEQ ID NO: 17, SEQ ID NO: 18 and SEQ ID NO: 19;

(b) Clone 2 of SEQ ID NO: 20, SEQ ID NO: 21, SEQ ID NO: 22, SEQ ID NO: 23, SEQ ID NO: 24 and SEQ ID NO: 25;

(c) Clone 3 of SEQ ID NO: 26, SEQ ID NO: 27, SEQ ID NO: 28, SEQ ID NO: 29, SEQ ID NO: 30 and SEQ ID NO: 31;

(d) Clone 4 of SEQ ID NO: 32, SEQ ID NO: 33, SEQ ID NO: 34, SEQ ID NO: 35, SEQ ID NO: 36 and SEQ ID NO: 37;

(e) Clone 5 of SEQ ID NO: 38, SEQ ID NO: 39, SEQ ID NO: 40, SEQ ID NO: 41, SEQ ID NO: 42 and SEQ ID NO: 43;

(f) Clone 6 of SEQ ID NO: 44, SEQ ID NO: 45, SEQ ID NO: 46, SEQ ID NO: 47, SEQ ID NO: 48 and SEQ ID NO: 49;

(g) Clone 7 of SEQ ID NO: 50, SEQ ID NO: 51, SEQ ID NO: 52, SEQ ID NO: 53, SEQ ID NO: 54 and SEQ ID NO: 55;

(h) Clone 8 of SEQ ID NO: 56, SEQ ID NO: 57, SEQ ID NO: 58, SEQ ID NO: 59, SEQ ID NO: 60 and SEQ ID NO: 61;

(i) Clone 9 of SEQ ID NO: 62, SEQ ID NO: 63, SEQ ID NO: 64, SEQ ID NO: 65, SEQ ID NO: 66 and SEQ ID NO: 67;

-continued (j) Clone 10 of SEQ ID NO: 68, SEQ ID NO: 69, SEQ ID NO: 70, SEQ ID NO: 71, SEQ ID NO: 72 and SEQ ID NO: 73;

(k) Clone 11 of SEQ ID NO: 74, SEQ ID NO: 75, SEQ ID NO: 76, SEQ ID NO: 77, SEQ ID NO: 78 and SEQ ID NO: 79;

(l) Clone 12 of SEQ ID NO: 80, SEQ ID NO: 81, SEQ ID NO: 82, SEQ ID NO: 83, SEQ ID NO: 84 and SEQ ID NO: 85;

(m) Clone 13 of SEQ ID NO: 86, SEQ ID NO: 87, SEQ ID NO: 88, SEQ ID NO: 89, SEQ ID NO: 90 and SEQ ID NO: 91;

(n) Clone 14 of SEQ ID NO: 92, SEQ ID NO: 93, SEQ ID NO: 94, SEQ ID NO: 95, SEQ ID NO: 96 and SEQ ID NO: 97;

(o) Clone 15 of SEQ ID NO: 98, SEQ ID NO: 99, SEQ ID NO: 100, SEQ ID NO: 101, SEQ ID NO: 102 and SEQ ID NO: 103;

(p) Clone 16 of SEQ ID NO: 104, SEQ ID NO: 105, SEQ ID NO: 106, SEQ ID NO: 107, SEQ ID NO: 108 and SEQ ID NO: 109; or (q) Clone 17 of SEQ ID NO: 110, SEQ ID NO: 111, SEQ ID NO: 112, SEQ ID NO: 113, SEQ ID NO: 114 and SEQ ID NO: 115;

wherein the sequences are defined according to Kabat nomenclature.

9. An antigen-binding protein, such as an antibody or antigen-binding fragment thereof, according to clause 7 or 8, wherein the antigen-binding site comprises the VH and/or VL domain sequence of, or a VH and/or VL domain sequence with at least 70, 75, 80, 81, 82, 83, 84, 85, 86, 87, 88, 89, 90, 91, 92, 93, 94, 95, 96, 97, 98 or 99% identity to, a clone selected from:

(a) Clone 1 of SEQ ID NO: 116 and SEQ ID NO: 117, respectively;

(b) Clone 2 of SEQ ID NO: 118 and SEQ ID NO: 119, respectively;

(c) Clone 3 of SEQ ID NO: 120 and SEQ ID NO: 121, respectively;

(d) Clone 4 of SEQ ID NO: 122 and SEQ ID NO: 123, respectively;

(e) Clone 5 of SEQ ID NO: 124 and SEQ ID NO: 125, respectively;

(f) Clone 6 of SEQ ID NO: 126 and SEQ ID NO: 127, respectively;

(g) Clone 7 of SEQ ID NO: 128 and SEQ ID NO: 129, respectively;

(h) Clone 8 of SEQ ID NO: 130 and SEQ ID NO: 131, respectively;

(i) Clone 9 of SEQ ID NO: 132 and SEQ ID NO: 133, respectively;

(j) Clone 10 of SEQ ID NO: 134 and SEQ ID NO: 135, respectively;

(k) Clone 11 of SEQ ID NO: 136 and SEQ ID NO: 137, respectively;

(l) Clone 12 of SEQ ID NO: 138 and SEQ ID NO: 139, respectively;

-continued

```
(m) Clone 13 of SEQ ID NO: 140 and SEQ ID NO:
141, respectively;

(n) Clone 14 of SEQ ID NO: 142 and SEQ ID NO:
143, respectively;

(o) Clone 15 of SEQ ID NO: 144 and SEQ ID NO:
145, respectively;

(p) Clone 16 of SEQ ID NO: 146 and SEQ ID NO:
147, respectively; or

(q) Clone 17 of SEQ ID NO: 148 and SEQ ID NO:
149, respectively;
```

wherein the sequences are defined according to Kabat nomenclature.

10. An antigen-binding protein, such as an antibody or antigen-binding fragment thereof, according to any one of clauses 7 to 9, wherein the antibody comprises the VH and/or VL domain of Clone 1 (#66) (SEQ ID NO: 116 and SEQ ID NO: 117, respectively) or of Clone 2 (#44) (SEQ ID NO: 118 and SEQ ID NO: 119, respectively).
11. An antigen-binding protein, such as an antibody or antigen-binding fragment thereof, according to any one of clauses 7 to 10, wherein the antibody is a chimeric antibody comprising a human Ig Fc region, preferably a human IgG1 Fc region.
12. An antigen-binding protein, such as an antibody or antigen-binding fragment thereof, according to any one of clauses 7 to 11, wherein the antibody comprises an Ig Fc region with effector function or enhanced effector function.
13. An antigen-binding protein, such as an antibody or antigen-binding fragment thereof capable of competing with an antibody according to any one of clauses 7 to 12 for binding to an isolated recombinant peptide comprising an epitope, said peptide comprising or consisting of residues 369-381 (SEQ ID NO: 1) of human 2N4R (amino acids 1-441) tau (SEQ ID NO: 2), wherein the epitope is comprised within residues 369-381 (SEQ ID NO: 1), when assessed in a competition assay.
14. An isolated recombinant peptide, binding molecule, or antigen-binding protein such as an antibody or fragment thereof, of any preceding clause which is the product of expression of a recombinant DNA or RNA sequence.
15. An isolated recombinant DNA or RNA sequence comprising a sequence encoding an isolated recombinant peptide, binding molecule, antigen-binding protein such as an antibody or fragment thereof, according to any one of clauses 1 to 13.
16. An isolated recombinant DNA sequence of clause 15 which is a vector, preferably an expression vector.
17. An isolated recombinant DNA sequence of clause 15 or 16 encoding an isolated recombinant peptide, binding molecule, antigen-binding protein such as an antibody or fragment thereof, according to any one of clauses 1 to 13 under control of a promoter.
18. A host cell comprising a DNA or RNA sequence according to any one of clauses 15 to 17.
19. A host cell of clause 18 capable of expressing an isolated recombinant peptide, binding molecule, antigen-binding protein or fragment thereof, of any one of clauses 1 to 13.
20. A method of making an isolated recombinant peptide, binding molecule, antigen-binding protein such as an antibody or fragment thereof, of any one of clauses 1 to 13 comprising culturing a host cell according to clause 18 or 19 in conditions suitable for expression of the isolated recombinant peptide, or antigen-binding protein such as an antibody or fragment thereof, and isolating the isolated recombinant peptide, or antigen-binding protein such as an antibody or fragment thereof.
21. A composition comprising an isolated recombinant peptide, binding molecule, antigen-binding protein such as an antibody or fragment thereof, according to any one of clauses 1 to 13 and a diluent, preferably a pharmaceutically acceptable diluent.
22. An immunogenic composition capable of inducing an immunological response in a subject inoculated with said composition, the composition comprising an isolated recombinant peptide according to any one of clauses 1 to 5 together with a pharmaceutically acceptable diluent, adjuvant and/or carrier.
23. An isolated recombinant peptide of one of clauses 1 to 13, or an immunogenic composition of clause 22, for use as a peptide vaccine.
24. An isolated recombinant peptide, binding molecule, antigen-binding protein such as an antibody or fragment thereof of any one of clauses 1 to 13, or a composition of any of clauses 21 to 23 for use as a medicament or for use in diagnosis.
25. An isolated recombinant peptide, binding molecule, antigen-binding protein such as an antibody or fragment thereof of any one of clauses 1 to 13, or a composition of any one of clauses 21 to 23, for use in the prophylactic or therapeutic treatment of a tauopathy, or for the manufacture of a medicament for the prophylactic or therapeutic treatment of a tauopathy, wherein preferably the tauopathy is selected from Alzheimer's disease, amyotrophic lateral sclerosis/parkinsonism-dementia complex, argyrophilic grains disease, beta-propeller protein associated neurodegeneration (BPAN), British type amyloid angiopathy, cerebral amyloid angiopathy, Creutzfeldt-Jakob disease, dementia pugilistica, diffuse neurofibrillary tangles with calcification, Down's syndrome, chronic traumatic encephalopathy (CTE), corticobasal degeneration (CBD), frontotemporal dementia (FTD), frontotemporal dementia and parkinsonism linked to chromosome 17 (FTDP-17), frontotemporal lobar degeneration, Gerstmann-Straussler-Scheinker disease, Hallervorden-Spatz disease, inclusion body myositis, multiple system atrophy, myotonic dystrophy, Niemann-pick disease type C, non-guamanian motor neuron disease with neurofibrillary tangles, Pick's disease, post-encephalitic parkinsonism, primary age-related tauopathy (PART), prion protein cerebral amyloid angiopathy, progressive subcortical gliosis, progressive supranuclear palsy (PSP), subacute sclerosing panencephalitis, tangle-dominant dementia, globular glial tauopathy, parkinsonism dementia complex of Guam, progressive non-fluent aphasia, multi-infarct dementia, ischemic stroke, traumatic brain injury (TBI) and stroke.
26. An isolated recombinant peptide, binding molecule, antigen-binding protein such as an antibody or fragment thereof of any one of clauses 1 to 13, or a composition of any one of clauses 21 to 23, that is capable of reducing uptake of extracellular monomeric and/or aggregated tau species by human neurons and/or promoting uptake of tau species by human astrocytes and/or preventing uptake of tau species by human astrocytes and/or increasing phagocytosis of tau species in human microglia and/or preventing tau-mediated inhibition of long term potentiation in rodent models.

27. An isolated recombinant peptide, binding molecule, antigen-binding protein such as an antibody or fragment thereof of any one of clauses 1 to 13, or composition of any one of clauses 21 to 23, for use to identify human tau proteins comprising an epitope formed by residues 369-381 (SEQ ID NO: 1) of human 2N4R tau (SEQ ID NO: 2).
28. An isolated recombinant peptide, binding molecule, antigen-binding protein such as an antibody or fragment thereof of any one of clauses 1 to 13, or composition of any one of clauses 21 to 22, for use to identify human tau proteins comprising an epitope formed by residues 373-379 (THKLTFR, SEQ ID NO: 150) of human 2N4R (amino acids 1-441) tau (SEQ ID NO: 2).
29. An isolated recombinant peptide, binding molecule, antigen-binding protein such as an antibody or fragment thereof of any one of clauses 1 to 13, or composition of any one of clauses 21 to 22, for use in a diagnostic test for a tauopathy.
30. A diagnostic kit comprising an isolated recombinant peptide, binding molecule, antigen-binding protein such as an antibody or fragment thereof of any one of clauses 1 to 13, or composition of any one of clauses 21 to 23 and a reagent capable of detecting an immunological (antigen-antibody) complex which contains said isolated recombinant peptide binding molecule, antigen-binding protein such as an antibody or fragment thereof, wherein optionally said isolated recombinant peptide and/or binding molecule, antigen-binding protein such as an antibody or fragment thereof is immobilized on a solid support (e.g., microplate well), and/or wherein optionally said immunological complex which contains said isolated recombinant peptide, binding molecule, antigen-binding protein or fragment thereof is detectable by ELISA or an alternative immunoassay method or by lateral flow.
31. A diagnostic kit according to clause 30, further comprising one or more control standards and/or specimen diluent and/or washing buffer.

Surprisingly the inventors have identified a unique immunogenic peptide, comprising epitopes present on extracellular, monomeric, oligomeric and/or aggregated soluble and/or insoluble tau and have raised antibodies capable of binding specifically to the peptide and epitopes of the invention. Without wishing to be bound by theory, it is thought that such antibodies will have a reduced risk of adverse events related to disruption of physiological extracellular tau function, when compared to antibodies targeting the N-terminus of tau. Antibodies of the invention may be useful in detection of tau in tauopathies such as Alzheimer's disease, e.g., in CSF or blood (plasmaor serum), for diagnosis, monitoring disease progression, prognosing disease, etc. Prevention of tau-mediated toxicity can be demonstrated based on evidence from immunodepletion experiments, such as in vivo LTP as a model of tau-mediated synaptotoxicity, and in vitro tests, e.g., reduction in neuronal tau uptake as a model of pathological tau spreading. Amelioration of tau-mediated synaptotoxicity and a reduction in neuronal uptake of tau may be beneficial in reducing cognitive decline and neurodegeneration respectively, in patients with, suspected of having, or predisposed towards developing a tauopathy, such as Alzheimer's disease.

DETAILED DESCRIPTION

The invention relates to an isolated synthetic or recombinant peptide comprising an epitope, said peptide consisting of residues 369-381 (KKIETHKLTFREN, SEQ ID NO: 1) of human tau (tau1-441 SEQ ID NO: 2).

An isolated synthetic or recombinant peptide of the invention may consist of residues 369-381 (KKIETHKLTFREN, SEQ ID NO: 1) of human tau (tau1-441 SEQ ID NO: 2).

An isolated recombinant peptide of the invention may further comprise a N-terminal cysteine (CKKIETHKLTFREN, SEQ ID NO: 13) or a C-terminal cysteine for conjugation of a carrier protein or detectable label.

Carrier proteins that may be conjugated to an isolated recombinant peptide of the invention may be selected from Keyhole limpet hemocyanin (KLH), *Concholepas concholepas* hemocyanin ("Blue Carrier"), Bovine serum albumin (BSA), Cationized BSA (cBSA) and Ovalbumin (OVA).

The invention provides novel epitopes present on extracellular tau species, the epitopes being formed by residues 369-381 (KKIETHKLTFREN, SEQ ID NO: 1) of human tau (taul-441 SEQ ID NO: 2). Preferably an epitope of the invention is formed by residues of the amino acid sequence 373 to 379 (THKLTFR, SEQ ID NO: 150) of human 2N4R (amino acids 1-441) tau (SEQ ID NO: 2). In particularly preferred aspects an epitope of the invention is formed by residues of the amino acid sequence 373 to 379 (THKLTFR, SEQ ID NO: 150) of human 2N4R (amino acids 1-441) tau (SEQ ID NO: 2), wherein the epitope comprises residues:

(a) L376 and F378, more preferably comprising residues H374, K375, L376, F378, R379 (e.g., the epitope bound by Clone 1, #66) or
(b) K375, T377 and R379, preferably comprising residues T373, K375, T377 and R379 (e.g. the epitope bound by Clone 2, #44).

The invention further relates to binding molecules, e.g., antigen-binding proteins, such as antibodies and antigen-binding fragments thereof that comprise a CDR-based antigen-binding site, specific for (i.e. capable of binding specifically to) an epitope comprised within residues 369-381 (KKIETHKLTFREN, SEQ ID NO: 1) of human tau (taul-441 SEQ ID NO: 2).

Binding molecules, e.g., antigen-binding proteins, such as antibodies and antigen-binding fragments thereof of the invention bind to extracellular tau species that include epitopes formed by residues 369-381 (KKIETHKLTFREN, SEQ ID NO: 1) of human tau (taul-441 SEQ ID NO: 2). Preferably binding molecules, e.g., antigen-binding proteins, such as antibodies and antigen-binding fragments thereof of the invention bind to extracellular tau species characterised in that the epitope to which they bind is formed by residues of the amino acid sequence 373 to 379 (THKLTFR, SEQ ID NO: 150) of human 2N4R (amino acids 1-441) tau (SEQ ID NO: 2). In particularly preferred aspects of the invention binding molecules, e.g., antigen-binding proteins, such as antibodies and antigen-binding fragments thereof of the invention bind extracellular tau species characterised in that the epitope is formed by residues of the amino acid sequence 373 to 379 (THKLTFR, SEQ ID NO: 150) of human 2N4R (amino acids 1-441) tau (SEQ ID NO: 2), wherein the epitope comprises residues:

(a) L376 and F378, more preferably comprising residues H374, K375, L376, F378, R379 (e.g., the epitope bound by Clone 1, #66) or
(b) K375, T377 and R379, preferably comprising residues T373, K375, T377 and R379 (e.g., the epitope bound by Clone 2, #44).

The invention provides a binding molecule capable of binding specifically to an isolated synthetic or recombinant peptide of the invention.

The invention provides a binding molecule capable of binding specifically an epitope formed by an isolated synthetic or recombinant peptide of the invention.

The invention provides a binding molecule capable of binding specifically to an isolated synthetic or recombinant peptide or epitope of the invention that is also capable of binding to human tau (tau1-441 SEQ ID NO: 2).

The invention provides a binding molecule capable of binding specifically an epitope formed by an isolated synthetic or recombinant peptide of the invention, preferably said binding molecule is also capable of binding to human tau (tau1-441 SEQ ID NO: 2), preferably said human tau is extracellular tau or a fragment thereof comprising residues 369-381 (SEQ ID NO: 1), more preferably comprising residues 373 to 379 (SEQ ID NO: 150), of human 2N4R (amino acids 1-441) tau (SEQ ID NO: 2), A binding molecule of the invention may be an antigen-binding protein, such as an antibody or an antigen-binding fragment thereof, a domain antibody, a protein scaffold, an affimer, or a bicyclic peptide, or a peptide or oligonucleotide aptamer.

An antibody or antigen-binding fragment thereof of the invention may be produced by recombinant means. A "recombinant antibody" is an antibody which has been produced by a recombinantly engineered host cell. An antibody or antigen-binding fragment thereof in accordance with the invention is optionally isolated or purified.

The term "antibody" or "antibody molecule" describes an immunoglobulin whether natural or partly or wholly synthetically produced. An antigen-binding protein of the invention may be an antibody, preferably a monoclonal antibody, and may be human or non-human, chimeric or humanised.

The antibody molecule is preferably a monoclonal antibody molecule. Examples of antibodies are the immunoglobulin isotypes, such as immunoglobulin G, and their isotypic subclasses, such as IgG1, IgG2, IgG3 and IgG4, as well as fragments thereof. The four human subclasses (IgG1, IgG2, IgG3 and IgG4) each contain a different heavy chain; but they are highly homologous and differ mainly in the hinge region and the extent to which they activate the host immune system. IgG1 and IgG4 contain two inter-chain disulphide bonds in the hinge region, IgG2 has 4 and IgG3 has 11 inter-chain disulphide bonds.

The terms "antibody" and "antibody molecule", as used herein, includes antibody fragments, such as Fab and scFv fragments, provided that said fragments comprise a CDR-based antigen binding site for an epitope defined by residues within 369-381 of human tau, preferably the epitope to which they bind is formed and is defined by residues of the amino acid sequence 373 to 379 (THKLTFR, SEQ ID NO: 150) of human 2N4R (amino acids 1-441) tau (SEQ ID NO: 2). The epitope may be defined by residues: (a) L376 and F378, more preferably residues H374, K375, L376, F378, R379 (e.g., the epitope bound by Clone 1, #66) or (b) K375, T377 and R379, more preferably comprising residues T373, K375, T377 and R379 (e.g., the epitope bound by Clone 2, #44). Examples of antibody fragments include but are not limited to Fv, Fab, Fab', Fab'-SH, F(ab')2; diabodies; linear antibodies; single-chain antibody molecules (e.g., scFv) and domain antibodies (sdAbs). Unless the context requires otherwise, the terms "antigen-binding protein", "antibody" or "antibody molecule", as used herein, is thus equivalent to "antibody or antigen-binding fragment thereof".

Antibodies are immunoglobulins, which have the same basic structure consisting of two heavy and two light chains forming two Fab arms containing identical domains that are attached by a flexible hinge region to the stem of the antibody, the Fc domain, giving the classical 'Y' shape. The Fab domains consist of two variable and two constant domains, with a variable heavy (VH) and constant heavy 1 (CH1) domain on the heavy chain and a variable light (VL) and constant light (CL) domain on the light chain. The two variable domains (VH and VL) form the variable fragment (Fv), which provides the CDR-based antigen specificity of the antibody, with the constant domains (CH1 and VL) acting as a structural framework. Each variable domain contains three hypervariable loops, known as complementarity determining regions (CDRs). On each of the VH and VL the three CDRs (CDR1, CDR2, and CDR3) are flanked by four less-variable framework (FR) regions (FR1, FW2, FW3 and FW4) to give a structure FW1-CDR1-FW2-CDR2-FW3-CDR3-FW4. The CDRs provide a specific antigen recognition site on the surface of the antibody.

Both Kabat and ImMunoGeneTics (IMGT) numbering nomenclature may be used herein. Generally, unless otherwise indicated (explicitly or by context) amino acid residues are numbered herein according to the Kabat numbering scheme (Kabat et al., 1991, J Immunol 147(5): 1709-19). For those instances when the IMGT numbering scheme is used, amino acid residues are numbered herein according to the ImMunoGeneTics (IMGT) numbering scheme described in Lefranc et al., 2005, Dev Comp Immunol 29(3): 185-203.

It is possible to take monoclonal and other antibodies and use techniques of recombinant DNA technology to produce other antibodies or chimeric molecules which generally retain the specificity of the original antibody. Such techniques may involve introducing the CDRs into a different immunoglobulin framework, or grafting variable regions onto a different immunoglobulin constant region. Introduction of the CDRs of one immunoglobulin into another immunoglobulin is described for example in EP-A-184187, GB2188638A or EP-A-239400. Alternatively, a hybridoma or other cell producing an antibody molecule may be subject to genetic mutation or other changes, which may or may not alter the binding specificity of antibodies produced.

As antibodies can be modified in a number of ways, the term "antigen-binding protein" or "antibody" should be construed as covering antibody fragments, derivatives, functional equivalents and homologues of antibodies, including any polypeptide comprising an immunoglobulin binding domain, an aptamer, affimer or bicyclic peptide, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

An example of an antibody fragment comprising both CDR sequences and CH3 domain is a minibody, which comprises a scFv joined to a CH3 domain (Hu et al. (1996) Cancer Res 56(13): 3055-61).

A domain (single-domain) antibody is a peptide, usually about 110 amino acids long, comprising one variable domain (VH) of a heavy-chain antibody, or of an IgG. A single-domain antibody (sdAb), (e.g., nanobody), is an antibody fragment consisting of a single monomeric variable antibody domain. Like a whole antibody (comprising two heavy and two light chains), it is an antigen-binding protein able to bind selectively to a specific antigen. Domain antibodies have a molecular weight of only 12-15 kDa and are thus much smaller than antibodies composed of two heavy protein chains and two light chains (150-160 kDa), and domain antibodies are even smaller than Fab fragments (~50 kDa, one light chain and half a heavy chain) and single-chain variable fragments (~25 kDa, two variable domains, one from a light and one from a heavy chain). Single-domain antibodies have been engineered from heavy-chain antibodies found in camelids; these are termed VHH fragments. Cartilaginous fish also have heavy-chain antibodies (IgNAR, 'immunoglobulin new antigen receptor'), from which single-domain antibodies called VNAR fragments can be obtained. A domain (single-domain) antibody may be a VH or VL. A domain antibody may be a VH or VL of human or murine origin. Although most single-domain antibodies are heavy chain variable domains, light chain single-domain antibodies (VL) have also been shown to bind specifically to target epitopes. Protein scaffolds have relatively defined three-dimensional structures and typically contain one or more regions which are amenable to specific or random amino acid sequence variation, to produce antigen-binding regions within the scaffold that are capable of binding to an antigen.

An aptamer is a short peptide or oligonucleotide (DNA, RNA or XNA) that is capable of binding to a specific target antigen.

An affimer is a small, highly stable protein that binds a target antigen with similar specificity and affinity to that of an antibody. Affimers are engineered non-antibody binding proteins, designed to mimic the molecular recognition characteristics of monoclonal antibodies.

Bicyclic peptides are synthetic, highly constrained peptides, usually between 9 and 15 amino acids in size. Conformational rigidity of bicyclic peptides is achieved by tethering the peptides on molecular scaffolds, providing bicyclic peptides molecules with a high target specificity and an affinity that resembles that of antibodies or small proteins.

An antibody or antigen-binding fragment of the invention binds to an epitope formed by residues of the amino acid sequence 369-381 (SEQ ID NO: 1) of human tau (SEQ ID NO: 2) Preferably binding molecules, e.g., antigen-binding proteins, such as antibodies and antigen-binding fragments thereof of the invention bind to extracellular tau species characterised in that the epitope to which they bind is formed by residues of the amino acid sequence 373 to 379 (THKLTFR, SEQ ID NO: 150) of human 2N4R (amino acids 1-441) tau (SEQ ID NO: 2).

In particularly preferred aspects of the invention binding molecules, e.g., antigen-binding proteins, such as antibodies and antigen-binding fragments thereof of the invention bind extracellular tau species characterised in that the epitope is formed by residues of the amino acid sequence 373 to 379 (THKLTFR, SEQ ID NO: 150) of human 2N4R (amino acids 1-441) tau (SEQ ID NO: 2), wherein the epitope comprises residues:

(a) L376 and F378, more preferably comprising residues H374, K375, L376, F378, R379 (e.g., the epitope bound by Clone 1, #66) or (b) K375, T377 and R379, preferably comprising residues T373, K375, T377 and R379 (e.g., the epitope bound by Clone 2, #44).

Binding in this context may refer to specific binding. The term "specific" may refer to the situation in which the antibody molecule will not show any significant binding to molecules other than its specific binding partner(s), here an epitope within residues 369-381 of human tau, e.g., formed by residues of the amino acid sequence 373 to 379 (THKLTFR, SEQ ID NO: 150) of human 2N4R (amino acids 1-441) tau (SEQ ID NO: 2. The term "specific" is also applicable where the antibody molecule is specific for particular epitopes of the invention, such as an epitope comprised within residues 369-381 of human tau, e.g., formed by residues of the amino acid sequence 373 to 379 of human tau, as described herein, that are carried by a number of antigens in which case the antibody molecule will be able to bind to the various antigens carrying the epitope. The novel epitopes described herein may be present in tau species that are monomeric, oligomeric or aggregates. Tau species may be full length or truncated in regions outside of residues 369-381, or 0.373-379 The epitope may be present in fragments of tau that comprise residues 369-381 (SEQ ID NO: 1), and/or fragments of tau that comprise residues 373-379 (SEQ ID NO: 150), of human tau1-441 (SEQ ID NO: 2) Preferably binding molecules, e.g., antigen-binding proteins, such as antibodies and antigen-binding fragments thereof of the invention bind to extracellular tau species characterised in that the epitope to which they bind is formed by residues of the amino acid sequence 373 to 379 (THKLTFR, SEQ ID NO: 150) of human 2N4R (amino acids 1-441) tau (SEQ ID NO: 2).

In particularly preferred aspects of the invention binding molecules, e.g., antigen-binding proteins, such as antibodies and antigen-binding fragments thereof of the invention bind extracellular tau species characterised in that the epitope is formed by residues of the amino acid sequence 373 to 379 (THKLTFR, SEQ ID NO: 150) of human 2N4R (amino acids 1-441) tau (SEQ ID NO: 2), wherein the epitope comprises residues:

(a) L376 and F378, more preferably comprising residues H374, K375, L376, F378, R379 (e.g., the epitope bound by Clone 1, #66) or (b) K375, T377 and R379, preferably comprising residues T373, K375, T377 and R379 (e.g., the epitope bound by Clone 2, #44).

Amino acids may be referred to by their one letter or three letter codes, or by their full name. The one and three letter codes, as well as the full names, of each of the twenty standard amino acids are set out below.

TABLE 2

Amino acids, one and three-letter codes.

| Amino acid | One letter code | Three letter code |
|---|---|---|
| alanine | A | Ala |
| arginine | R | Arg |
| asparagine | N | Asn |
| aspartic acid | D | Asp |
| cysteine | C | Cys |
| glutamic acid | E | Glu |
| glutamine | Q | Gln |
| glycine | G | Gly |
| histidine | H | His |
| isoleucine | I | Ile |
| leucine | L | Leu |
| lysine | K | Lys |
| methionine | M | Met |
| phenylalanine | F | Phe |
| proline | P | Pro |
| serine | S | Ser |
| threonine | T | Thr |
| tryptophan | W | Trp |
| tyrosine | Y | Tyr |
| valine | V | Val |

In preferred embodiments, an antibody or an antigen-binding fragment thereof of the invention may comprise the set of six CDRs (HCDR1, HCDR2, HCDR3, LCDR1, LCDR2, and LCDR3) of any of clones 1 to 17 (e.g., as set forth in Table 5 when defined by Kabat nomenclature).

An antibody or an antigen-binding fragment thereof of the invention may comprise a VH and/or VL sequence of any of clones 1 to 17.

An antibody or an antigen-binding fragment thereof of the invention may comprise one or more, e.g., 1, 2, 3, 4, 5, 6, 7, 8, 9 or 10 further amino acid modifications in the VH and/or VL sequences, provided that functional properties of the antibody are retained.

A modification may be an amino acid substitution, deletion or insertion. Preferably, the modification is a substitution.

In preferred embodiments in which one or more amino acids are substituted with another amino acid, the substitutions may be conservative substitutions, for example according to the following table. In some embodiments, amino acids in the same category in the middle column are substituted for one another, i.e., a non-polar amino acid is substituted with another non-polar amino acid, for example. In some embodiments, amino acids in the same line in the rightmost column are substituted for one another.

TABLE 3

| | Amino acids | |
|---|---|---|
| ALIPHATIC | Non-polar | GAP |
| | | ILV |
| | Polar - uncharged | CSTM |
| | | NQ |
| | Polar - charged | DE |
| | | KR |
| AROMATIC | | HFWY |

In some embodiments, substitution(s) may be functionally conservative. That is, in some embodiments the substitution may not affect (or may not substantially affect) one or more functional properties (e.g., binding affinity) of the antibody molecule comprising the substitution as compared to the equivalent unsubstituted antibody molecule.

In a preferred embodiment, an antibody or an antigen-binding fragment thereof of the invention may comprise a VH and/or VL domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the VH and/or VL sequences of the invention set forth herein.

In preferred embodiments, an antibody or an antigen-binding fragment thereof of the invention may comprise a VH domain sequence of any one of clones 1 to 17 set forth in SEQ ID NO: 116, 118, 120, 122, 124, 126, 128, 130, 132, 134, 136, 138, 140, 142, 144, 146, 148 or a VH domain with an amino acid sequence which has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the sequence of any one of clones 1 to 17 set forth in SEQ ID NO: 116, 118, 120, 122, 124, 126, 128, 130, 132, 134, 136, 138, 140, 142, 144, 146, 148.

In a preferred embodiment, an antibody of the invention comprises a VH domain amino acid sequence comprising the set of HCDRs: HCDR1, HCDR2, and HCDR3 of any of clones 1 to 17 respectively, e.g., as set forth in Table 5 when defined by Kabat nomenclature and the VH domain has an amino acid sequence with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the sequence of any one of clones 1 to 17 set forth in SEQ ID NO: 116, 118, 120, 122, 124, 126, 128, 130, 132, 134,136, 138, 140, 142, 144, 146, 148.

In preferred embodiments, an antibody or an antigen-binding fragment thereof of the invention may comprise a VL domain amino acid sequence of any one of clones 1 to 17 set forth in SEQ ID NO: 117, 119, 121, 123, 125, 127, 129, 131, 133, 135, 137, 139, 141, 143, 145, 147, 149 or a VL domain with an amino acid sequence which has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the sequence of any one of clones 1 to 17 set forth in SEQ ID NO: 117, 119, 121, 123, 125, 127, 129, 131, 133, 135, 137, 139, 141,143, 145, 147, 149.

In a preferred embodiment, an antibody of the invention comprises a VL domain comprising the set of LCDRs: LCDR1, LCDR2 and LCDR3 of any of clones 1 to 17 respectively, e.g., as set forth in Table 5 when defined by Kabat nomenclature and the VL domain has an amino acid sequence with at least 70%, at least 75%, at least 80%, at least 81%, at least 82%, at least 83%, at least 84%, at least 85%, %, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the sequence of any one of clones 1 to 17 set forth in SEQ ID NO:117, 119, 121, 123, 125, 127, 129, 131, 133, 135, 137, 139, 141, 143, 145, 147, 149.

Sequence identity is commonly defined with reference to the algorithm GAP (Wisconsin GCG package, Accelerys Inc, San Diego USA). GAP uses the Needleman and Wunsch algorithm to align two complete sequences, maximising the number of matches and minimising the number of gaps. Generally, default parameters are used, with a gap creation penalty equaling 12 and a gap extension penalty equaling 4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm may be used (Nucl. Acids Res. (1997) 25 3389-3402). Sequence identity may be defined using the Bioedit, ClustalW algorithm.

Alignments were performed using Snapgene and based on MUSCLE (Multiple Sequence Comparison by Log-Expectation) algorithms (Edgar (2004a) Nucleic Acids Res 32:1792-7; Edgar (2004b) BMC Bioinformatics 5:113.).

The antibody may comprise a CH2 domain. The CH2 domain is preferably located at the N-terminus of the CH3 domain, as in the case in a human IgG molecule. The CH2 domain of the antibody is preferably the CH2 domain of human IgG1, IgG2, IgG3, or IgG4, more preferably the CH2 domain of human IgG1. The sequences of human IgG domains are known in the art.

The antibody may comprise an immunoglobulin hinge region, or part thereof, at the N-terminus of the CH2 domain. The immunoglobulin hinge region allows the two CH2-CH3 domain sequences to associate and form a dimer. Preferably, the hinge region, or part thereof, is a human IgG1, IgG2, IgG3 or IgG4 hinge region, or part thereof. More preferably, the hinge region, or part thereof, is an IgG1 hinge region, or part thereof.

The sequence of the CH3 domain is not particularly limited. Preferably, the CH3 domain is a human immunoglobulin G domain, such as a human IgG1, IgG2, IgG3, or IgG4 CH3 domain, most preferably a human IgG1 CH3 domain.

An antibody of the invention may comprise a human IgG1, IgG2, IgG3, or IgG4 constant region. The sequences of human IgG1, IgG2, IgG3, or IgG4 CH3 domains are known in the art. An antibody of the invention may comprise a non-human IgG constant region, e.g., a rabbit IgG1 constant region.

An antibody of the invention may comprise a human IgG Fc with effector function.

Fc receptors (FcRs) are key immune regulatory receptors connecting the antibody mediated (humoral) immune response to cellular effector functions. Receptors for all classes of immunoglobulins have been identified, including FcγR (IgG), FcεRI (IgE), FcαRI (IgA), FcμR (IgM) and FcδR (IgD). There are three classes of receptors for human IgG found on leukocytes: CD64 (FcγRI), CD32 (FcγRIIa, FcγRIIb and FcγRIIc) and CD16 (FcγRIIIa and FcγRIIIb). FcγRI is classed as a high affinity receptor (nanomolar range KD) while FcγRII and FcγRIII are low to intermediate affinity (micromolar range KD).

In antibody dependent cellular cytotoxicity (ADCC), FcvRs on the surface of effector cells (natural killer cells, macrophages, monocytes and eosinophils) bind to the Fc region of an IgG which itself is bound to a target cell. Upon binding a signalling pathway is triggered which results in the secretion of various substances, such as lytic enzymes, perforin, granzymes and tumour necrosis factor, which mediate in the destruction of the target cell. The level of ADCC effector function various for IgG subtypes. Although this is dependent on the allotype and specific FcvR in simple terms ADCC effector function is high for human IgG1 and IgG3, and low for IgG2 and IgG4. See the below for IgG subtype variation in effector functions, ranked in decreasing potency.

| Effector Function | Species | IgG Subtype Potency |
|---|---|---|
| ADCC | Human | IgG1 ≥ IgG3 >> IgG4 > IgG2 |
| | Mouse | IgG2b > IgG2a > IgG1 >> IgG3 |
| C1q Binding | Human | IgG3 > IgG1 >> IgG2 > IgG4 |
| | Mouse | IgG2a > IgG2b > IgG3 > IgG1 |

FcγRs bind to IgG asymmetrically across the hinge and upper CH2 region. Knowledge of the binding site has resulted in engineering efforts to modulate IgG effector functions Antibodies of the invention may have an Fc with enhanced effector function or with reduced effector function.

The potency of antibodies can be increased by enhancement of the ability to mediate cellular cytotoxicity functions, such as antibody-dependent cell-mediated cytotoxicity (ADCC) and antibody-dependent cell-mediated phagocytosis (ADCP). A number of mutations within the Fc domain have been identified that either directly or indirectly enhance binding of Fc receptors and significantly enhance cellular cytotoxicity: the mutations S239D/A330L/1332E ("3M"), F243L or G236A. Alternatively enhancement of effector function can be achieved by modifying the glycosylation of the Fc domain, FcγRs interact with the carbohydrates on the CH2 domain and the glycan composition has a substantial effect on effector function activity. Afucosylated (non-fucosylated) antibodies, exhibit greatly enhanced ADCC activity through increased binding to FcγRIIIa.

Activation of ADCC and CDC may be desirable for some therapeutic antibodies, however, in some embodiments, an antibody that does not activate effector functions is preferred.

Due to their lack of effector functions, IgG4 antibodies are the preferred IgG subclass for receptor blocking without cell depletion. However IgG4 molecules can exchange half-molecules in a dynamic process termed Fab-arm exchange. This phenomenon can occur between therapeutic antibodies and endogenous IgG4. The S228P mutation has been shown to prevent this recombination process allowing the design of IgG4 antibodies with a reduced propensity for Fab-arm exchange.

Fc engineering approaches have been used to determine the key interaction sites for the IgG1 Fc domain with Fcγ receptors and C1q and then mutate these positions to reduce or abolish binding. Through alanine scanning the binding site of C1q to a region covering the hinge and upper CH2 of the Fc domain was identified. The CH2 domain of an antibody or fragment of the invention may comprise one or more mutations to decrease or abrogate binding of the CH2 domain to one or more Fcγ receptors, such as FcγRI, FcγRIIa, FcγRIIb, FcγRIII and/or to complement. CH2 domains of human IgG domains normally bind to Fcγ receptors and complement, decreased binding to Fcγ receptors is expected to decrease antibody-dependent cell-mediated cytotoxicity (ADCC) and decreased binding to complement is expected to decrease the complement-dependent cytotoxicity (CDC) activity of the antibody molecule. Mutations to decrease or abrogate binding of the CH2 domain to one or more Fcγ receptors and/or complement are known in the art. An antibody molecule of the invention may comprise an Fc with modifications K322A/L234A/L235A or L234F/L235E/P331S ("TM"), which almost completely abolish FcγR and C1q binding. An antibody molecule of the invention may comprise a CH2 domain, wherein the CH2 domain comprises alanine residues at EU positions 234 and 235 (positions 1.3 and 1.2 by IMGT numbering) ("LALA mutation"). Furthermore, complement activation and ADCC can be decreased by mutation of Pro329 (position according to EU numbering), e.g., to either P329A or P329G. The antibody molecule of the invention may comprise a CH2 domain, wherein the CH2 domain comprises alanine residues at EU positions 234 and 235 (positions 1.3 and 1.2 by IMGT numbering) and an alanine (LALA-PA) or glycine (LALA-PG) at EU position 329 (position 114 by IMGT numbering). Additionally or alternatively an antibody molecule of the invention may comprise an alanine, glutamine or glycine at EU position 297 (position 84.4 by IMGT numbering).

Modification of glycosylation on asparagine 297 of the Fc domain, which is known to be required for optimal FcR interaction may confer a loss of binding to FcRs; a loss of binding to FcRs has been observed in N297 point mutations. An antibody molecule of the invention may comprise an Fc with an N297A, N297G or N297Q mutation. An antibody molecule of the invention with an aglycosyl Fc domain may be obtained by enzymatic deglycosylation, by recombinant expression in the presence of a glycosylation inhibitor, or following the expression of Fc domains in bacteria.

IgG naturally persists for a prolonged period in the serum due to FcRn-mediated recycling, giving it a typical half-life of approximately 21 days. Half-life can be extended by engineering the pH-dependant interaction of the Fc domain with FcRn to increase affinity at pH 6.0 while retaining minimal binding at pH 7.4. The T250Q/M428L variant, conferred an approximately 2-fold increase in IgG half-life (assessed in rhesus monkeys), while the M252Y/S254T/T256E variant ("YTE"), gave an approximately 4-fold increase in IgG half-life (assessed in cynomolgus monkeys). Extending half-life may allow the possibility of decreasing administration frequency, while maintaining or improving efficacy.

Immunoglobulins are known to have a modular architecture comprising discrete domains, which can be combined in a multitude of different ways to create multispecific, e.g. bispecific, trispecific, or tetraspecific antibody formats. Exemplary multispecific antibody formats are described in Spiess et al. (2015) Mol Immunol 67: 95-106 and Kontermann (2012) Mabs 4(2): 182-97, for example. The antibodies of the invention may be employed in such multispecific formats.

The invention provides an antigen-binding protein, such as an antibody or antigen binding fragment thereof, capable of competing with an antibody of the invention described herein (e.g., comprising a set of HCDR and LCDRs (e.g., as listed in table 5 when defined by Kabat nomenclature) and/or a VH and VL amino acid sequence of any one of clones 1 to 17) for binding to an isolated recombinant peptide comprising an epitope, said peptide comprising or consisting of residues 369-381 (SEQ ID NO: 1) of human 2N4R tau (SEQ ID NO: 2), when assessed in a competition assay.

Competition assays include cell-based and cell-free binding assays including an immunoassay such as ELISA, HTRF, flow cytometry, fluorescent microvolume assay technology (FMAT) assay, Mirrorball, high content imaging based fluorescent immunoassays, radioligand binding assays, bio-layer interferometry (BLI), surface plasmon resonance (SPR) and thermal shift assays.

An antibody that binds to the same epitope as, or an epitope overlapping with, a reference antibody refers to an antibody that blocks binding of the reference antibody to its binding partner (e.g., an antigen or "target" ") in a competition assay by 50% or more, and/or conversely, the reference antibody blocks binding of the antibody to its binding partner in a competition assay by 50% or more. Such antibodies are said to compete for binding to an epitope of interest.

An antigen-binding protein, such as an antibody or antigen-binding fragment thereof of the invention may be conjugated to a detectable label (for example, a radioisotope); or to a bioactive molecule. In this case, the antigen-binding protein, such as an antibody or antigen-binding fragment thereof may be referred to as a conjugate. Such conjugates may find application in the treatment and/or diagnosis of diseases as described herein. Such conjugates may find application for the detection (e.g., in vitro detection) an epitope within an amino acid sequence consisting of residues 369-381 (SEQ ID NO: 1) of human 2N4R (amino acids 1-441) tau (SEQ ID NO: 2), as described herein.

The antigen-binding proteins of the invention (including conjugates) may be useful in the detection (e.g., in vitro detection) of an epitope of the invention (an epitope present on an isolated recombinant peptide consisting of residues 369-381 (SEQ ID NO: 1) of human 2N4R (amino acids 1-441) tau (SEQ ID NO: 2)) as described herein, thus, the present invention relates to the use of an antigen-binding protein of the invention for detecting the presence of an epitope of the invention in a sample. The antigen-binding protein may be conjugated to a detectable label as described elsewhere herein.

In a preferred embodiment, the present invention relates to an in vitro method of detecting an epitope of the invention in a sample, wherein the method comprises incubating an antigen-binding protein of the invention with a sample of interest, and determining binding of the antigen-binding protein to an epitope of the invention present in the sample, wherein binding of the antigen-binding protein indicates the presence of an epitope of the invention in the sample. Methods for detecting binding of an antigen-binding protein to its target antigen are known in the art and include ELISA, ICC, IHC, immunofluorescence, western blot, IP, SPR and flow cytometry.

The sample of interest may be a sample obtained from an individual. The individual may be human. Samples include, but are not limited to, tissue such as brain tissue, cerebrospinal fluid (CSF), primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, plasma, serum, blood-derived cells, urine, saliva, sputum, tears, perspiration, mucus, tumour lysates, and tissue culture medium, tissue extracts such as homogenized tissue, tumour tissue, cellular extracts, and combinations thereof.

Following incubation, antigen-binding protein to antigen binding, e.g., antibody to antigen binding, is detected using an appropriate detection system. The method of detection can be direct or indirect, and may generate a fluorescent or chromogenic signal. Direct detection involves the use of primary antibodies that are directly conjugated to a label. Indirect detection methods employ a labelled secondary antibody raised against the primary antigen-binding protein, e.g., antibody, host species. Indirect methods may include amplification steps to increase signal intensity. Commonly used labels for the visualization (i.e., detection) of antigen-binding protein—antigen (e.g., antibody—epitope) interactions include fluorophores and enzymes that convert soluble substrates into insoluble, chromogenic end products.

The term "detecting" is used herein in the broadest sense to include both qualitative and quantitative measurements of a target molecule. Detecting includes identifying the mere presence of the target molecule in a sample as well as determining whether the target molecule is present in the sample at detectable levels. Detecting may be direct or indirect.

Suitable detectable labels which may be conjugated to antigen-binding proteins, such as antibodies, are known in the art and include radioisotopes such as iodine-125, iodine-131, yttrium-90, indium-111 and technetium-99; fluorochromes, such as fluorescein, rhodamine, phycoerythrin, Texas Red and cyanine dye derivatives for example, Cy7, Alexa750 and Alexa Fluor 647; chromogenic dyes, such as diaminobenzidine; latex beads; enzyme labels such as horseradish peroxidase; phospho or laser dyes with spectrally isolated absorption or emission characteristics; electrochemiluminescent labels, such as SULFO-TAG which may be detected via stimulation with electricity in an appropriate chemical environment; and chemical moieties, such as biotin, which may be detected via binding to a specific cognate detectable moiety, e.g., labelled avidin or streptavidin.

An antigen-binding protein, such as an antibody or fragment thereof, of the invention may be conjugated to the detectable label by means of any suitable covalent or non-covalent linkage, such as a disulphide or peptide bond. Suitable peptide linkers are known in the art and may be 5 to 25, 5 to 20, 5 to 15, 10 to 25, 10 to 20, or 10 to 15 amino acids in length.

The invention also provides a nucleic acid or set of nucleic acids encoding an antibody or antigen-binding fragment of the invention, as well as a vector comprising such a nucleic acid or set of nucleic acids.

Where the nucleic acid encodes the VH and VL domain, or heavy and light chain, of an antibody molecule of the invention, the two domains or chains may be encoded on the same or on separate nucleic acid molecules.

An isolated nucleic acid molecule may be used to express an antibody molecule of the invention. The nucleic acid will generally be provided in the form of a recombinant vector for expression. Another aspect of the invention thus provides a vector comprising a nucleic acid as described above. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Vectors may be plasmids, viral e.g. phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant antibody molecules are known in the art, and include bacterial, yeast, insect or mammalian host cells. A preferred host cell is a mammalian cell, such as a CHO, NSO, or HEK cell, for example a HEK293 cell.

A recombinant host cell comprising a nucleic acid or the vector of the invention is also provided. Such a recombinant host cell may be used to produce an antigen-binding protein (e.g., antibody) of the invention. Thus, also provided is a method of producing an antigen-binding protein, e.g., antibody, of the invention, the method comprising culturing the recombinant host cell under conditions suitable for production of the antigen-binding protein, e.g., antibody. The method may further comprise a step of isolating and/or purifying the antigen-binding protein, e.g., antibody.

Thus the invention provides a method of producing an antigen-binding protein, e.g., antibody, of the invention comprising expressing a nucleic acid encoding the antigen-binding protein, 20 e.g., antibody, in a host cell and optionally isolating and/or purifying the antigen-binding protein, e.g., antibody, thus produced. Methods for culturing host cells are well-known in the art. Techniques for the purification of recombinant antigen-binding proteins, e.g., antibodies, are well-known in the art and include, for example HPLC, FPLC or affinity chromatography, e.g., using Protein A or Protein L. In some embodiments, purification may be performed using an affinity tag on an antigen-binding protein, e.g., antibody. The method may also comprise formulating the antigen-binding protein, e.g., antibody, into a pharmaceutical composition, optionally with a pharmaceutically acceptable excipient or other substance as described below.

Antigen-binding proteins, e.g., antibodies, of the invention are expected to find application in therapeutic applications, in particular therapeutic applications in humans, for example in the treatment of a tauopathy, including but not limited to, a tauopathy selected from Alzheimer's disease, amyotrophic lateral sclerosis/parkinsonism-dementia complex, argyrophilic grains disease, beta-propeller protein associated neurodegeneration (BPAN), British type amyloid angiopathy, cerebral amyloid angiopathy, Creutzfeldt-Jakob disease, dementia pugilistica, diffuse neurofibrillary tangles with calcification, Down's syndrome, chronic traumatic encephalopathy (CTE), corticobasal degeneration (CBD), frontotemporal dementia (FTD), frontotemporal dementia and parkinsonism linked to chromosome 17 (FTDP-17), frontotemporal lobar degeneration, Gerstmann-Straussler-Scheinker disease, Hallervorden-Spatz disease, inclusion body myositis, multiple system atrophy, myotonic dystrophy, Niemann-pick disease type C, non-guamanian motor neuron disease with neurofibrillary tangles, Pick's disease, post-encephalitic parkinsonism, primary age-related tauopathy (PART), prion protein cerebral amyloid angiopathy, progressive subcortical gliosis, progressive supranuclear palsy (PSP), subacute sclerosing panencephalitis, tangle-dominant dementia, globular glial tauopathy, parkinsonism dementia complex of Guam, progressive non-fluent aphasia, multi-infarct dementia, ischemic stroke, traumatic brain injury (TBI) and stroke.

Also provided is a composition, such as a pharmaceutical composition, comprising an antigen-binding protein, e.g., antibody, according to the invention and an excipient, such as a pharmaceutically acceptable excipient.

The invention further provides an antigen-binding protein, e.g., antibody, of the invention, for use in a method of treatment. Also provided is a method of treating a patient, wherein the method comprises administering to the patient a therapeutically-effective amount of an antigen-binding protein, e.g., antibody, according to the invention. Further provided is the use of an antigen-binding protein, e.g., antibody, according to the invention for use in the manufacture of a medicament. A patient, as referred to herein, is preferably a human patient.

The invention also provides an antigen-binding protein, e.g., antibody, of the invention, for use in a method of treating a tauopathy, such as Alzheimer's disease, in a patient. Also provided is a method of treating a tauopathy, such as Alzheimer's disease, in a patient, wherein the method comprises administering to the patient a therapeutically-effective amount of an antigen-binding protein, e.g., antibody, according to the invention. Further provided is the use of an antigen-binding protein, e.g., antibody, according to the invention for use in the manufacture of a medicament for the treatment of a tauopathy, such as Alzheimer's disease, in a patient. The treatment may further comprise administering to the patient a second therapy, such as an FDA-approved AD medication, e.g., acetylcholinesterase inhibitors (e.g. donepezil), acetylcholine receptor positive modulators (e.g., Galantamine), NMDA receptor antagonists (e.g., memantine), or Parkinson's disease medications e.g., carbidopa-levodopa, dopamine receptor antagonists (e.g. pramipexole), monoamine oxidase B inhibitors (e.g., selegiline), catechol O-methyltransferase (COMT) inhibitors, amantadine, or anticholinergics (e.g., benztropine). The second therapy may be administered to the patient simultaneously, separately, or sequentially to the antigen-binding protein, e.g., antibody, of the invention.

In another aspect, the invention relates to an antigen-binding protein, e.g., antibody, of the invention for use in: a)

treating a tauopathy, b) delaying progression of a tauopathy, c) preserving cognitive function of a patient suffering from a tauopathy, d) prolonging the survival of a patient suffering from a tauopathy e) reducing levels of free C-terminal tau in the CSF and/or serum, f) reducing levels of total tau in the CSF and/or serum, g) reducing the ratio of free C-terminal tau:total tau in the CSF and/or serum, h) reducing levels of neurofilament light chain protein (NfL) in CSF and/or serum, i) reducing total intracellular tau levels in neurons and/or astrocytes and/or microglia, j) reducing the rate of decline of whole brain volume and/or regional brain volume, k) reducing the rate of decline of functional connectivity of brain, l) improving functional connectivity of the brain, or m) reducing the brain tau burden based on PET or other imaging methodology.

The antigen-binding protein, e.g., antibody, as described herein may thus be for use for therapeutic applications, in particular for the treatment of a tauopathy, such as Alzheimer's disease.

An antigen-binding protein, e.g., antibody, as described herein may be used in a method of treatment of the human or animal body. Related aspects of the invention provide;

(i) an antigen-binding protein, e.g., antibody, described herein for use as a medicament, (ii) an antigen-binding protein, e.g., antibody, described herein for use in a method of treatment of a disease or disorder, (iii) the use of an antigen-binding protein, e.g., antibody, described herein in the manufacture of a medicament for use in the treatment of a disease or disorder; and, (iv) a method of treating a disease or disorder in an individual, wherein the method comprises administering to the individual a therapeutically effective amount of an antigen-binding protein, e.g., antibody, as described herein.

The individual may be a patient, preferably a human patient.

Treatment may be any treatment or therapy in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, ameliorating, delaying, abating or arresting one or more symptoms and/or signs of the condition or prolonging survival of an individual or patient beyond that expected in the absence of treatment.

Treatment as a prophylactic measure (i.e., prophylaxis) is also included. For example, an individual susceptible to or at risk of the occurrence of a tauopathy, such as AD, may be treated as described herein. Such treatment may prevent or delay the occurrence of the disease in the individual.

A method of treatment as described may comprise administering at least one further treatment to the individual in addition to the antigen-binding protein, e.g., antibody. The antigen-binding protein, e.g., antibody, described herein may thus be administered to an individual alone or in combination with one or more other treatments. When the antigen-binding protein, e.g., antibody, is administered to the individual in combination with another treatment, the additional treatment may be administered to the individual concurrently with, sequentially to, or separately from the administration of the antigen-binding protein, e.g., antibody. Where the additional treatment is administered concurrently with the antigen-binding protein, e.g., antibody, the antigen-binding protein, e.g., antibody, and additional treatment may be administered to the individual as a combined preparation. For example, the additional therapy may be a known therapy or therapeutic agent for the disease to be treated.

Whilst an antigen-binding protein, e.g., antibody, may be administered alone, antigen-binding proteins, e.g., antibodies, will usually be administered in the form of a pharmaceutical composition, which may comprise at least one component in addition to the antigen-binding protein, e.g., antibody. Another aspect of the invention therefore provides a pharmaceutical composition comprising an antigen-binding protein, e.g., antibody, as described herein. A method comprising formulating an antigen-binding protein, e.g., antibody, into a pharmaceutical composition is also provided.

Pharmaceutical compositions may comprise, in addition to the antigen-binding protein, e.g., antibody, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by infusion, injection or any other suitable route, as discussed below.

For parenteral, for example subcutaneous or intravenous administration, e.g., by injection, the pharmaceutical composition comprising the antigen-binding protein, e.g., antibody, may be in the form of a parenterally acceptable aqueous solution which is pyrogen-free and has suitable pH, isotonicity and stability. Those of relevant skill in the art are able to prepare suitable solutions using, for example, isotonic vehicles, such as Sodium Chloride Injection, Ringer's Injection, or Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g., Zn-protein complexes); and/or non-ionic surfactants, such as TWEEN™, PLURONICS™ or polyethylene glycol (PEG).

In some embodiments, antigen-binding proteins, e.g., antibodies may be provided in a lyophilised form for reconstitution prior to administration. For example, lyophilised antigen-binding proteins, e.g., antibodies may be reconstituted in sterile water or saline prior to administration to an individual.

Administration may be in a "therapeutically effective amount", this being sufficient to show benefit to an individual. The actual amount administered, and rate and timecourse of administration, will depend on the nature and severity of what is being treated, the particular individual being treated, the clinical condition of the individual, the cause of the disorder, the site of delivery of the composition, the type of antigen-binding protein, e.g., antibody, the method of administration, the scheduling of administration and other factors known to medical practitioners. Prescription of treatment, e.g., decisions on dosage etc., is within the responsibility of general practitioners and other medical doctors, and may depend on the severity of the symptoms and/or progression of a disease being treated. Appropriate doses of antigen-binding protein, e.g., antibodies, are well known in the art. A therapeutically effective amount or suitable dose of an antigen-binding protein, e.g., antibody, can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the antigen-binding protein, e.g., antibody.

A typical antibody dose is in the range 100 μg to 1 g for systemic applications, and 1 μg to 1 mg for topical applications. An initial higher loading dose, followed by one or more lower doses, may be administered. This is a dose for a single treatment of an adult individual, which may be proportionally adjusted for children and infants, and also adjusted for other antibody formats in proportion to molecular weight.

Treatments may be repeated at daily, twice-weekly, weekly or monthly intervals, at the discretion of the physician. The treatment schedule for an individual may be dependent on the pharmacokinetic and pharmacodynamic properties of the antibody composition, the route of administration and the nature of the condition being treated.

Treatment may be periodic, and the period between administrations may be about two weeks or more, e.g., about three weeks or more, about four weeks or more, about once a month or more, about five weeks or more, or about six weeks or more. For example, treatment may be every two to four weeks or every four to eight weeks. Suitable formulations and routes of administration are described above.

In a preferred embodiment, an antibody as described herein may be for use in a method of treating Alzheimer's disease.

In preferred embodiments, an antigen-binding protein, such as an antibody or an antigen-binding fragment thereof of the invention does not bind to an epitope comprised in residues 379-408 or 379-391 of human tau 2N4R.

FIGURES

FIG. 1. Multiple species of tau released from human familial Alzheimer's disease neurons are not found in control neuron supernatants. Tau was immunoprecipitated (IP) from culture supernatants from non-disease control (NDC; lanes 1-3), familial Alzheimer's disease (fAD)-associated mutation, PSEN1 Y115C (PSEN; lanes 4-6) and frontotemporal dementia (FTD; lanes 7-9) associated mutation, MAPT IVS10+16 (MAPT) neurons, using commercial antibody, HT7 (lanes 3, 6, 9) or Tau-13 (lanes 2, 5, 8) and compared to an IgG control (1, 4, 7). Western blots show detection of tau species following each IP using anti-tau antibody (K9JA) (A). Bands highlighted and numbered 1-5 were excised and analysed by mass spectrometry.

Figure 2:
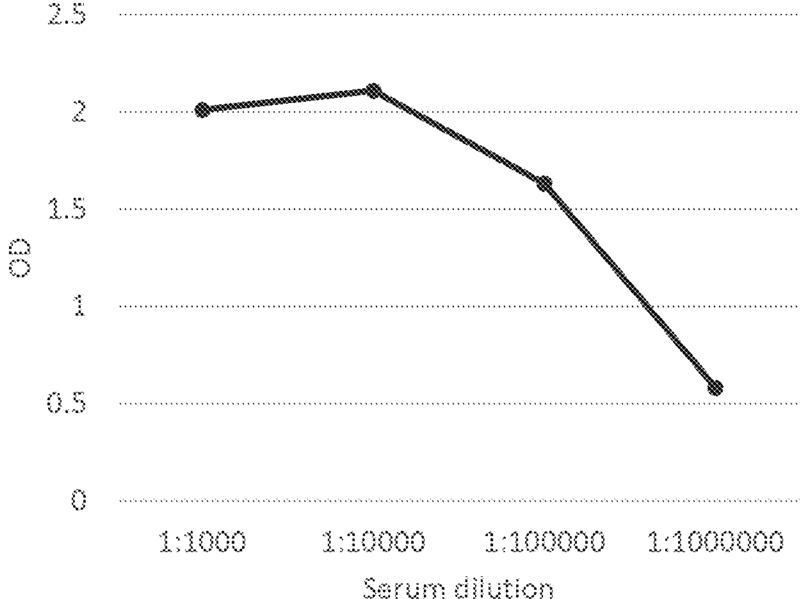

FIG. 2. A robust immune response was mounted following immunisation of a rabbit with KLH-conjugated target immunogen. Serum was taken at day 76-post-immunisation and tested for binding to immobilised target immunogen by ELISA. Binding of polyclonal IgG was observed at dilutions of 1:1000000 and below based on detection with an anti-rabbit IgG-HRP antibody. Data are shown as raw OD values from a single experiment. This rabbit was taken forward for isolation of plasma cells and screening for target-specific monoclonal IgG.

Figure 3:
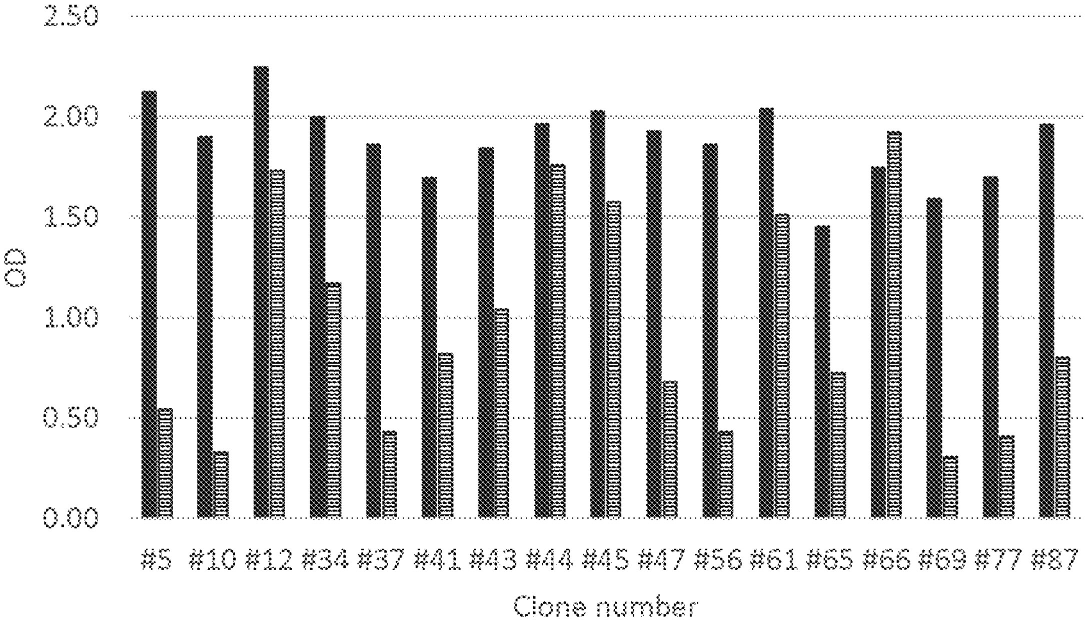

FIG. 3. A panel of IgG bind to the linear target peptide (SEQ ID NO: 13) and full length recombinant 2N4R tau in ELISA format. Supernatants from HEK cells transiently transfected with each IgG clone were tested at 1:50 for binding to the short linear peptide (black bars) and to full length recombinant 2N4R tau (striped bars). Binding of anti-tau IgG was detected using an HRP-conjugated anti-rabbit secondary antibody and data shown are from a representative experiment (n=1).

Figure 4:
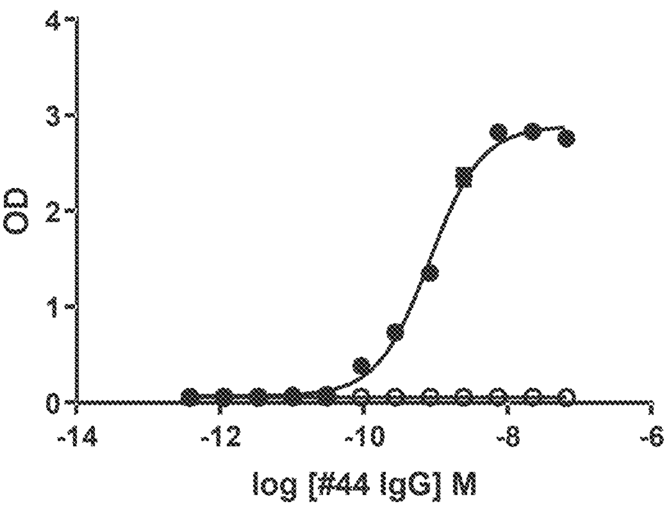
Figure 4:
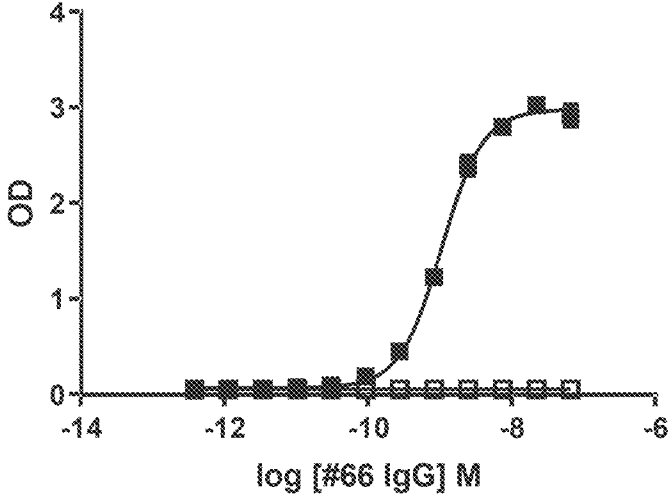

FIG. 4. Monoclonal antibodies detect full length recombinant 2N4R tau by ELISA in a concentration-dependent manner. Purified IgG generated in HEK cells were tested at concentrations from 0.1 ng/mL (0.67 pM) to 10 μg/mL (67 nM) for binding to full length recombinant 2N4R tau (solid symbols) and BSA (open symbols). Binding of anti-tau IgG, clone #44 (clone 2) (A) and clone #66 (clone 1) (B) was detected using an HRP-conjugated anti-rabbit secondary antibody and data shown are mean+/−SEM from a representative experiment based on n=2 wells per condition.

Figure 5:
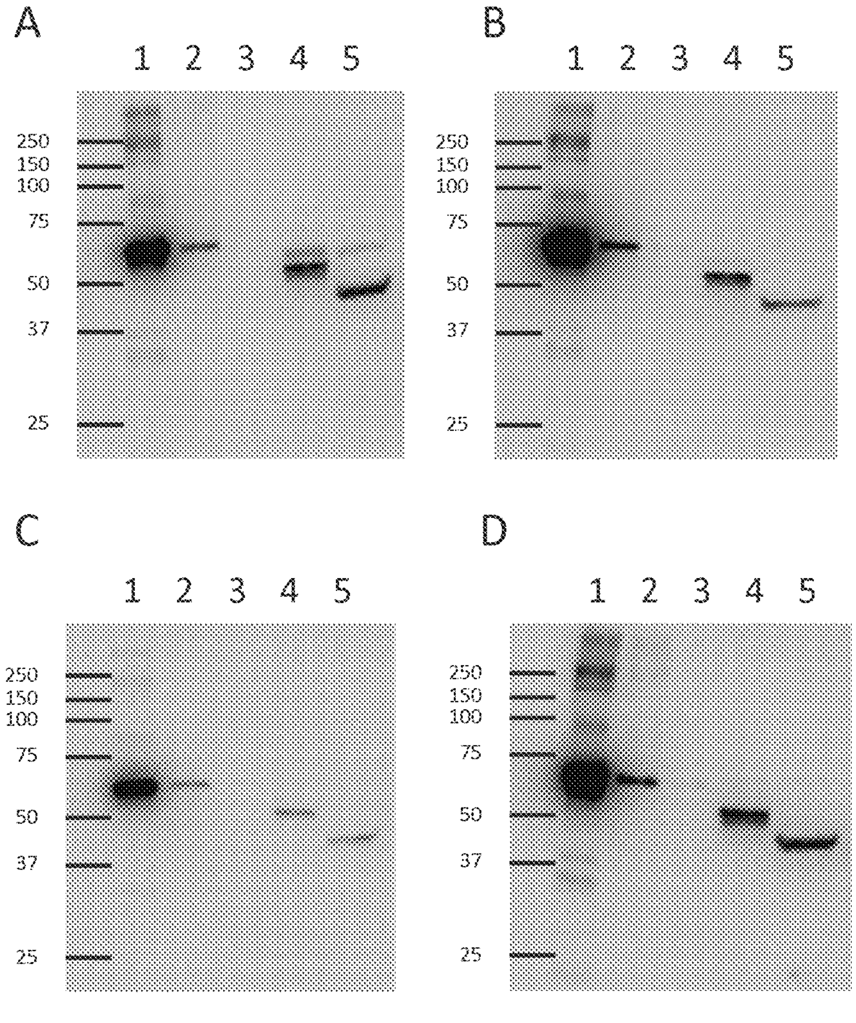

FIG. 5. Supernatants containing monoclonal anti-tau IgG detect phosphorylated and non-phosphorylated tau by western blot. Supernatants from HEK cells transiently expressing rabbit IgG clone #12 (Clone 3) (A), clone #44 (Clone 2) (B), clone #45 (Clone 4) (C) and clone #66 (Clone 1) (D) detect recombinant 2N4R tau at ~60 kD (200 ng, lane 1; 67 ng, lane 2; 22 ng, lane 3) and a dominant band at ~50 kD in human non-demented control iPSC-derived neurons, representing phosphorylated full length tau (lane 4). Lambda-phosphatase treatment of neuronal lysates is associated with a reduction in apparent molecular weight of tau species detected by all IgG clones (lane 5), consistent with dephosphorylation of tau. IgG clones are able to detect both phosphorylated and dephosphorylated tau equally.

Figure 6:
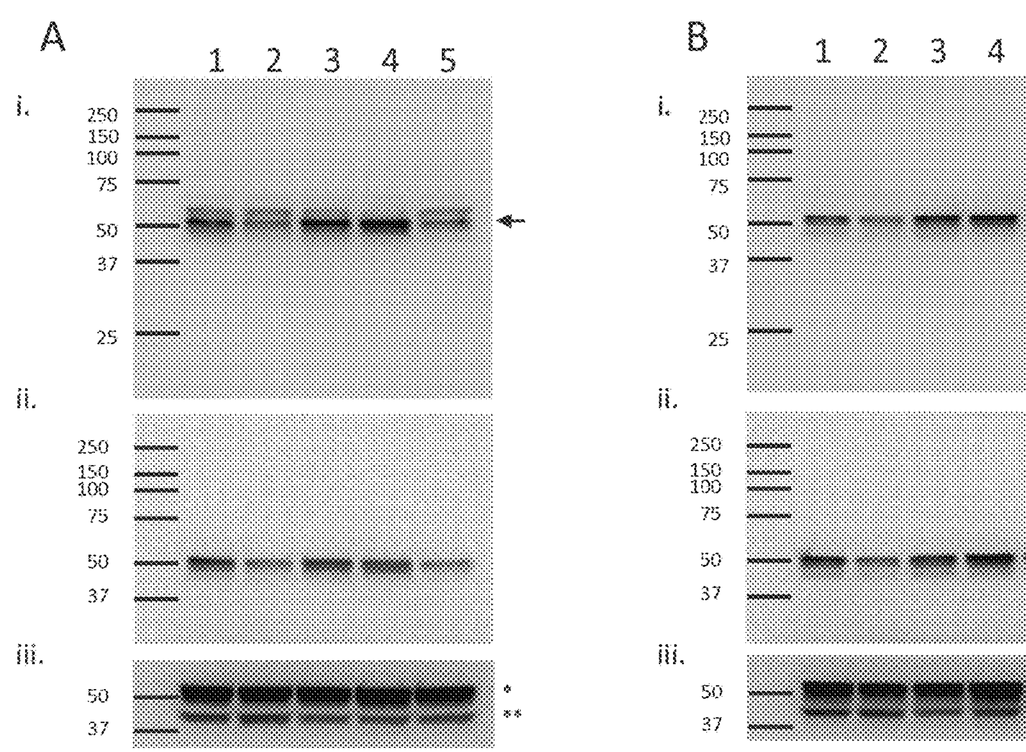

FIG. 6. Purified monoclonal anti-tau antibodies detect tau in human IPSC-derived neuronal cultures. Western blots of iPSC-derived neuronal lysates (day 80) are shown. Clone #44 (clone 2) (A) and clone #66 (clone 1) (B) IgG detect a dominant band at ~50 kD representing full length tau (arrows, i.). The middle panel shows the same blots reprobed using the commercially available antibody, HT7 (ii.). Actin (**) and neuronal tubulin (*) are shown on the lower blot and were included to control for loading and post-mortem protein degradation respectively (iii.). Neuronal lysates from non-disease controls (lane 1), familial Alzheimer's disease associated, PSEN Y115C (lane 2), trisomy 21 (lanes 3 and 4) and frontotemporal dementia associated, MAPT (IVS10+16) (lane 5) are shown.

Figure 7:
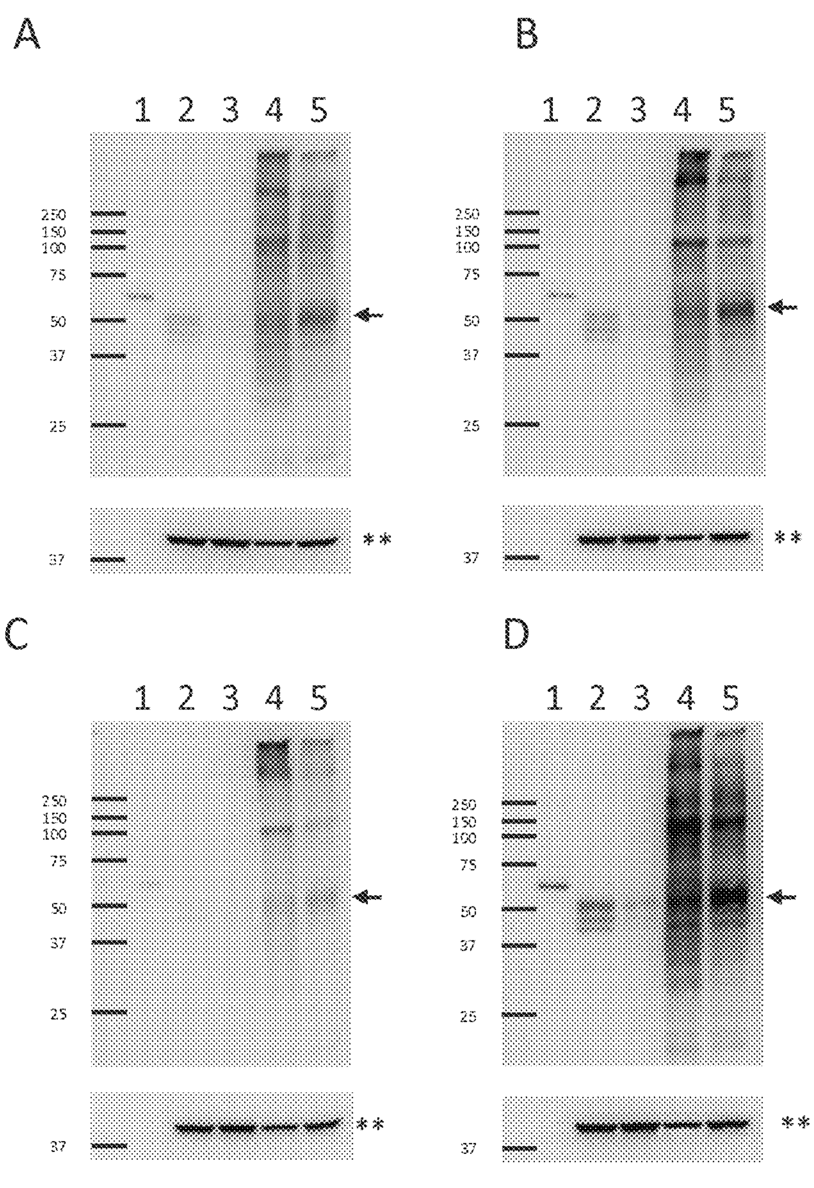

FIG. 7. Supernatants containing monoclonal anti-tau IgG detect increased levels of tau in Alzheimer's disease compared to non-demented control (NDC) post-mortem brain. Western blots of full length recombinant 2N4R tau (lane 1), brain lysates from NDC (lanes 2, 3) and Alzheimer's disease patients (lanes 4, 5) are shown. Supernatants from HEK cells transiently expressing clone #12 (Clone 3) (A), clone #44 (Clone 2) (B), clone #45 (Clone 4) (C) and clone #66 (Clone 1) (D) antibodies detect multiple species corresponding to different forms of tau, with increased detection of both high and low MW species in Alzheimer's samples. The arrow indicates a band corresponding to the expected size for full length tau. Actin (**) is shown on the lower blot as a loading control.

Figure 8:
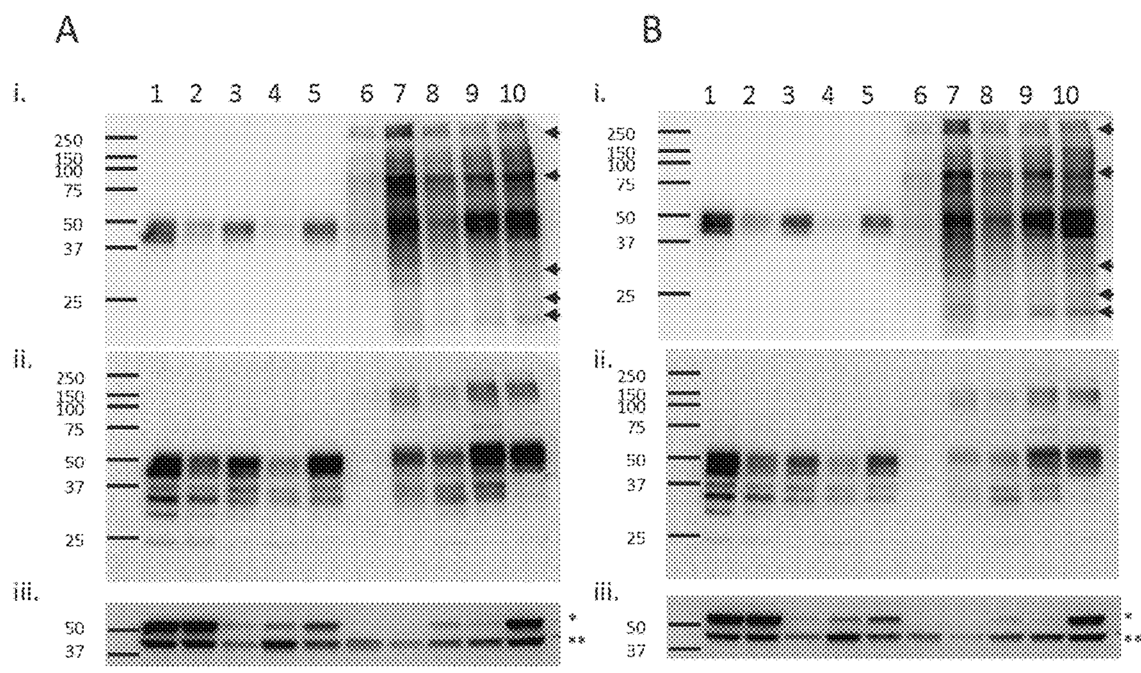

FIG. 8. Purified monoclonal anti-tau antibodies detect increased levels of tau in familial Alzheimer's disease (AD) compared to NDC post-mortem brain. Western blots of brain lysates from NDC (lanes 1-5) and Alzheimer's disease patients (lanes 6-10) are shown. Clone #44 (Clone 2) (A) and clone #66 (Clone 1) (B) antibodies detect multiple species corresponding to different forms of tau, with increased detection of both high and low MW species in Alzheimer's samples (top panel, i.). The middle panel shows the same blots re-probed using the commercially available mid-region anti-tau antibody, HT7 (ii.), and highlight the differences in tau species detected with mid-region compared to C-terminally directed antibodies. Arrows indicate tau species detected by C-terminal antibodies but not by HT7. Actin (**) and neuronal tubulin (*) are shown on the lower blot and were included to control for loading and post-mortem protein degradation respectively (iii.).

Figure 9:
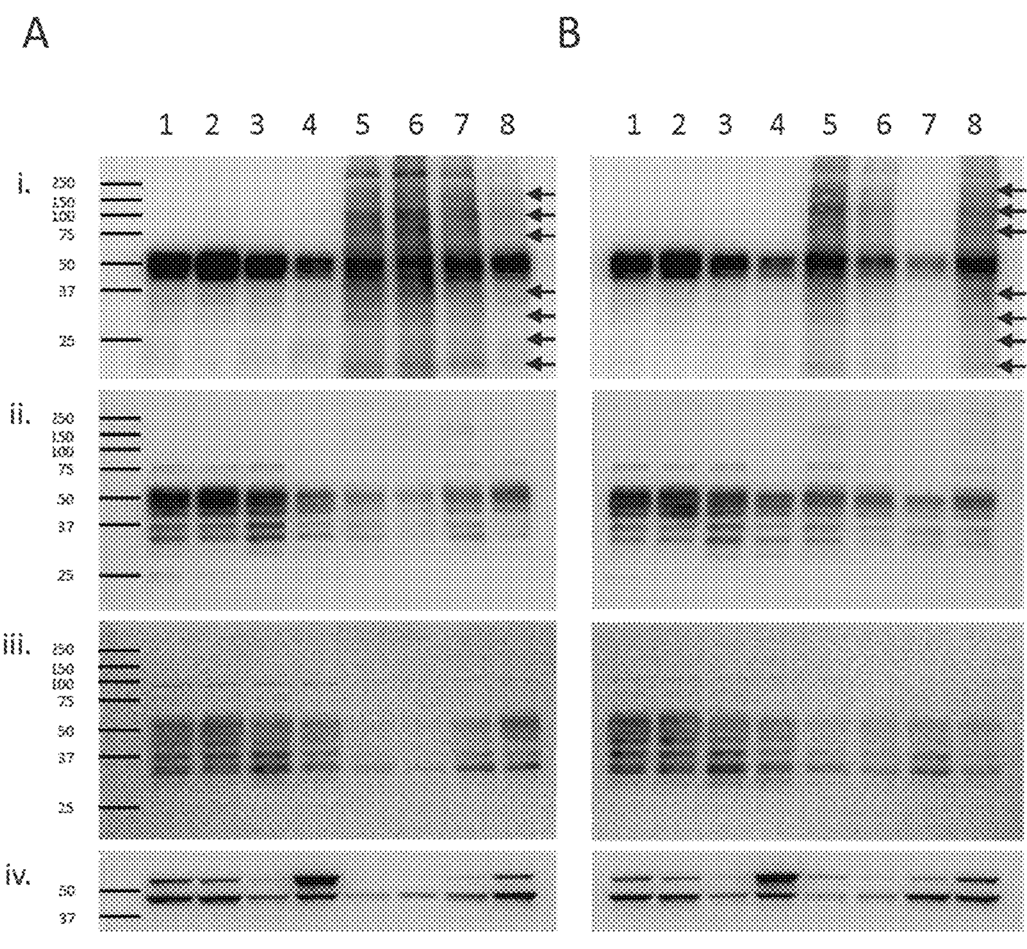

FIG. 9. Purified monoclonal anti-tau antibodies detect increased levels of tau in sporadic Alzheimer's disease (AD) and Dementia with Lewy Bodies (DLB) compared to non-demented control post-mortem brain. Western blots of brain lysates from NDC (A, B; lanes 1-4); sporadic Alzheimer's disease patients (A; lanes 5-8); and DLB patients (B; lanes 5-8) are shown. Clone #66 (Clone 1) detects multiple species corresponding to different forms of tau, with increased detection of both high and low MW species in Alzheimer's and DLB samples (top panel, i.). The middle panels show the same blots re-probed using the commercially available mid-region anti-tau antibodies, HT7 (ii.), and BT2 (iii.) and highlight the differences in tau species detected with mid-region compared to C-terminally directed antibodies. Arrows indicate tau species detected by C-terminal antibodies but not by HT7. Actin (**) and neuronal tubulin (*) are shown on the lower blot (iv.) and were included to control for loading and post-mortem protein degradation respectively FIG. 10. Monoclonal anti-tau antibody, clone #66 (clone 1) detects natively expressed tau in NDC and FTD-associated mutation (MAPT IVS10+16) iPSC-derived neurons by immunocytochemistry. NDC (A) and MAPT IVS10+16 iPSC-derived neurons (day 50+) (B) were incubated with anti-tau IgG, clone #66 overnight, before the addition of Alexa 488-conjugated anti-rabbit secondary antibody. Scale bar represents 50 μm in all images.

Figure 11:
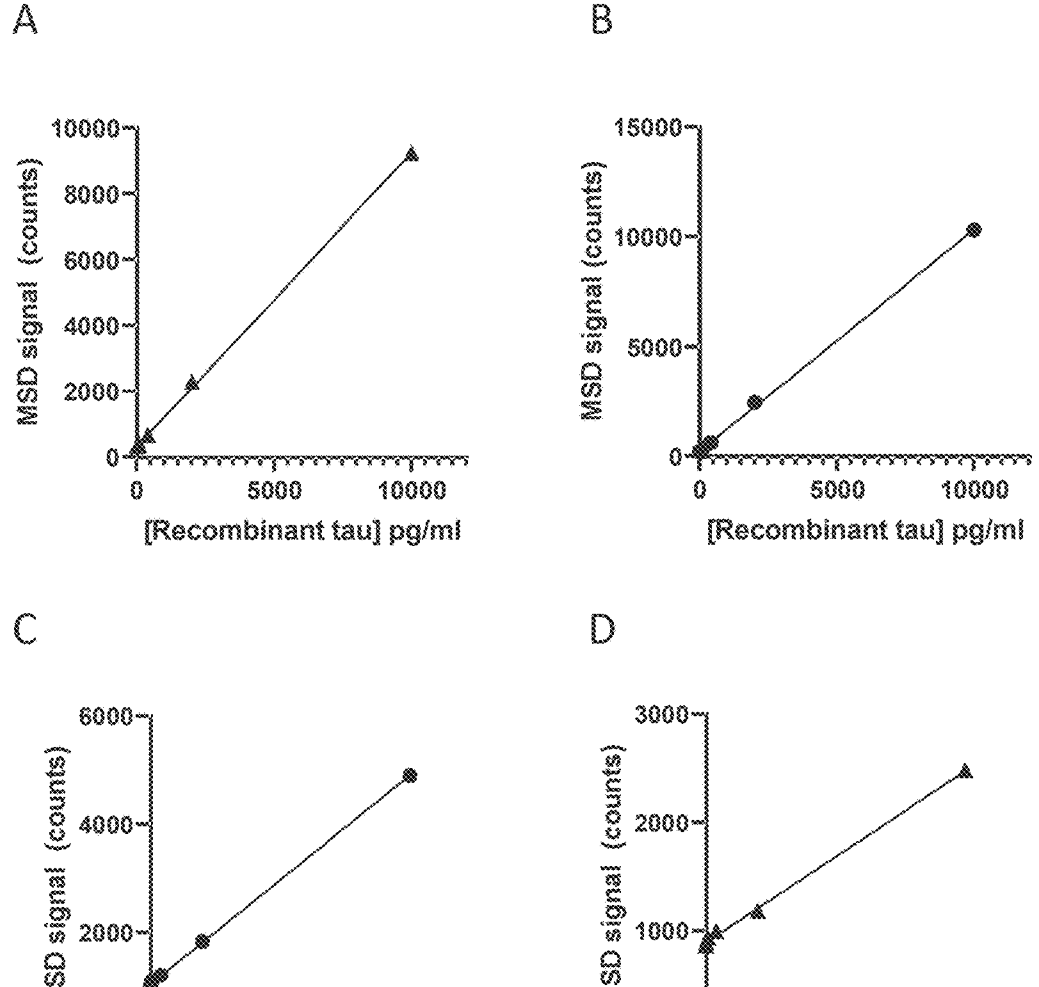

FIG. 11. Monoclonal antibodies detect full length recombinant 2N4R tau in MSD assays in combination with commercially available polyclonal and monoclonal antibodies. Clone #44 (Clone 2) (A, C) and clone #66 (Clone 1) (B, D) were used as capture antibodies (1 pg/mL), in combination with the commercial polyclonal antibody, K9JA (1 pg/mL) as detection antibody (A, B) or commercial monoclonal antibody, Tau5 (2 pg/mL; C, D). In this format, all antibody combinations were able to detect recombinant tau at concentrations above 80 μg/mL. Data represent single samples from a representative experiment.

Figure 12:
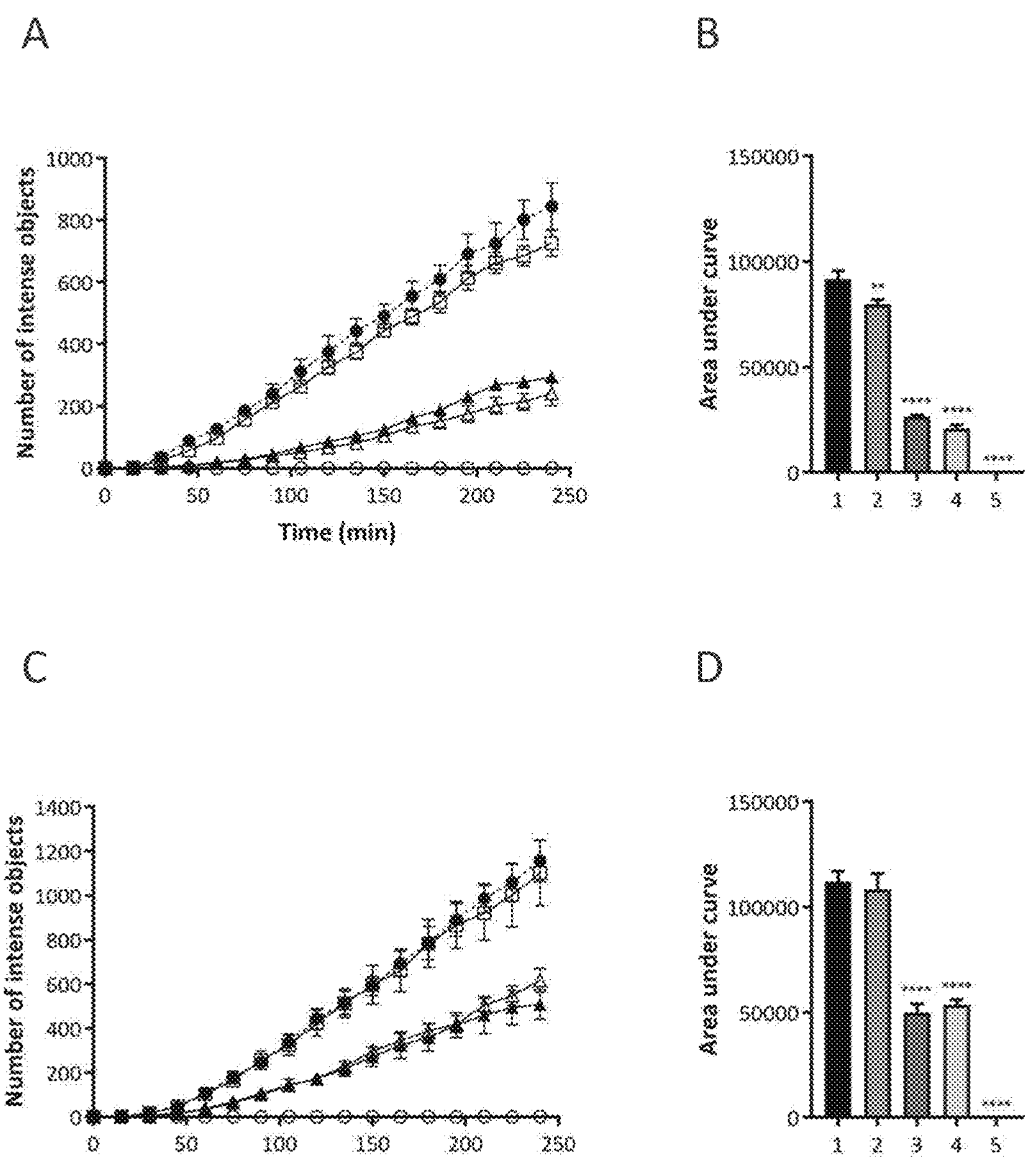

FIG. 12. Monoclonal anti-tau antibodies inhibit tau uptake by neurons. Antibody clones #44 (Clone 2) (solid triangles, solid line) or #66 (Clone 1) (open triangles, solid line) or an isotype control rabbit IgG (open squares, solid line) were incubated with full length pHrodo-labelled monomeric 2N4R tau (A, B) or aggregated 2N4R tau (C, D) before imaging on the OPERA-Phenix. Number of intense fluorescent objects quantified every 15 mins increased steadily over time in isotype control and no antibody (solid circles, dashed line) treatments, but was markedly reduced in cells treated with anti-tau antibody clones. Negative control wells including no pHrodo-labelled tau are also shown (open circles, dashed line). Data are shown as mean+/−SEM of n=4 wells from one representative experiment (A, C). Bar charts representing mean+/−SEM of area under curve calculated for no antibody (1), isotype control (2), clone #44 (clone 2) (3), clone #66 (clone 1) (4) and no pHrodo-labelled tau (5). **, p<0.0001; *, p<0.001; one-way ANOVA with Dunnett's multiple comparison test versus no antibody control (1).

Figure 13:
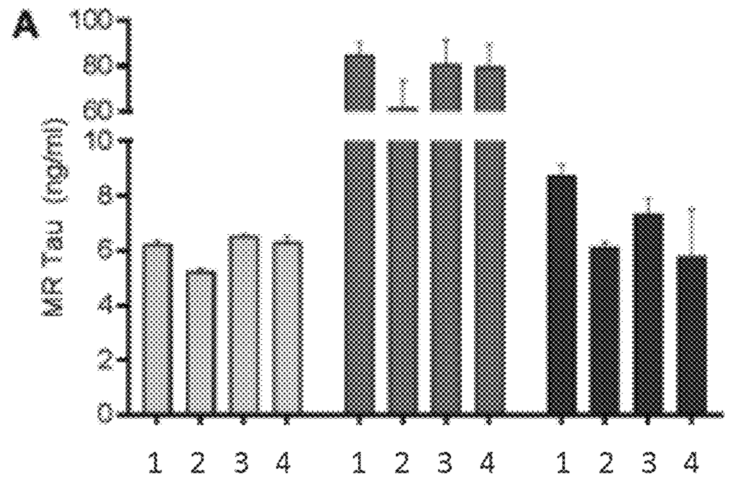
Figure 13:
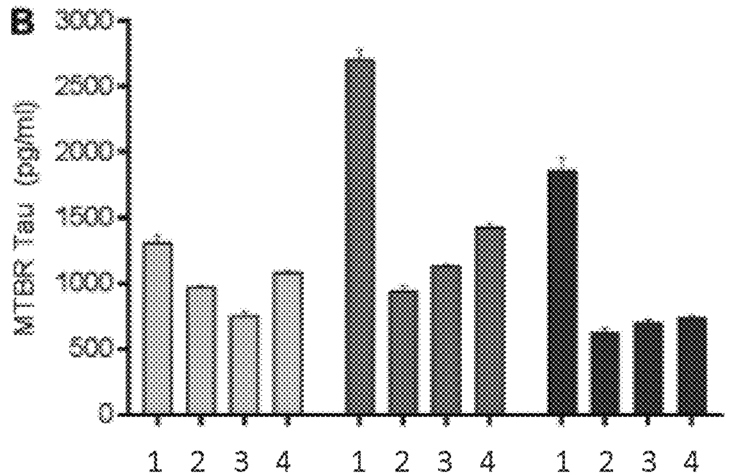

FIG. 13. Anti-tau IgG clones #44 (clone 2) and #66 (clone 1) immunodepleted tau species from human iPSC derived neuronal secretomes. Conditioned media from NDC (pale grey) and 2 separate TS21 lines (dark grey, black) were immunodepleted with preimmune serum (1), K9JA polyclonal antibody (2), #44 (Clone 2) (3) and #66 (Clone 1) (4) and analysed by mid-region (MR tau; based on commercial antibodies BT2 and Tau5; A) and microtubule binding region (MTBR tau; based on commercially available antibody, K9JA; B) ELISAs. Preimmune serum served as a negative control to mock deplete samples. Values represent the mean+/−SD of three technical replicates.

Figure 14:
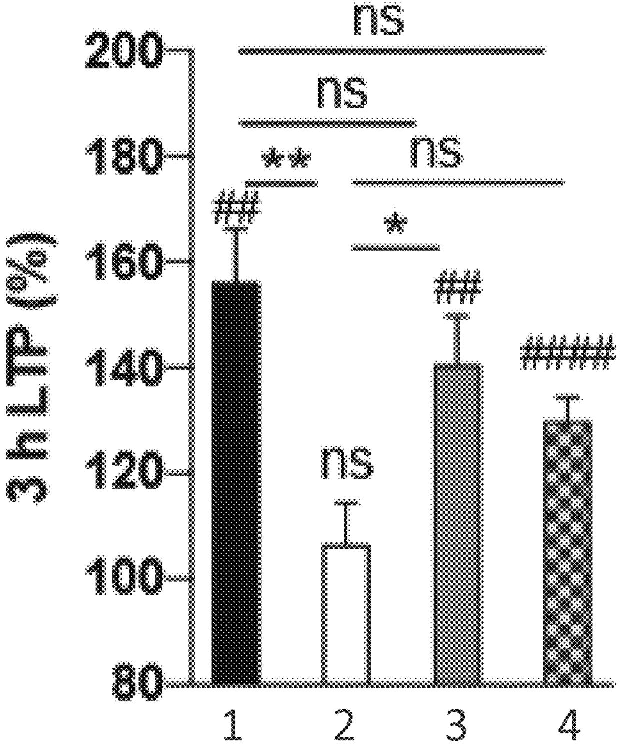

FIG. 14. Anti-tau IgG clones #44 (Clone 2) and #66 (Clone 1) prevented tau-mediated blockade of long term potentiation (LTP) in vivo. Hippocampal LTP was measured in anesthetized rats in the presence of secretomes generated by trisomy 21 (TS21) iPSC-derived neuronal cultures. LTP was induced in vehicle treated animals (black bar; 1), but was inhibited in the presence of mock-depleted TS21 secretome (white bar; 2). LTP induction was observed in the presence of TS21 secretomes immunodepleted using IgG clone #44 (clone 2) (grey bar; 3) or #66 (clone 1) (checked bar; 4), indicating the removal of tau species responsible for the LTP block. The magnitude of LTP is expressed as the percentage of pre-stimulation baseline EPSP amplitude (±SEM) for n=4 (vehicle) or n=7 (secretome samples) animals. **, p<0.01; −p<0.05; one-way ANOVA with Bonferroni multiple comparison test versus vehicle control (1); ####, p<0.0001, ##, p<0.01, paired t-test, post-versus pre-LTP induction.

Figure 15:
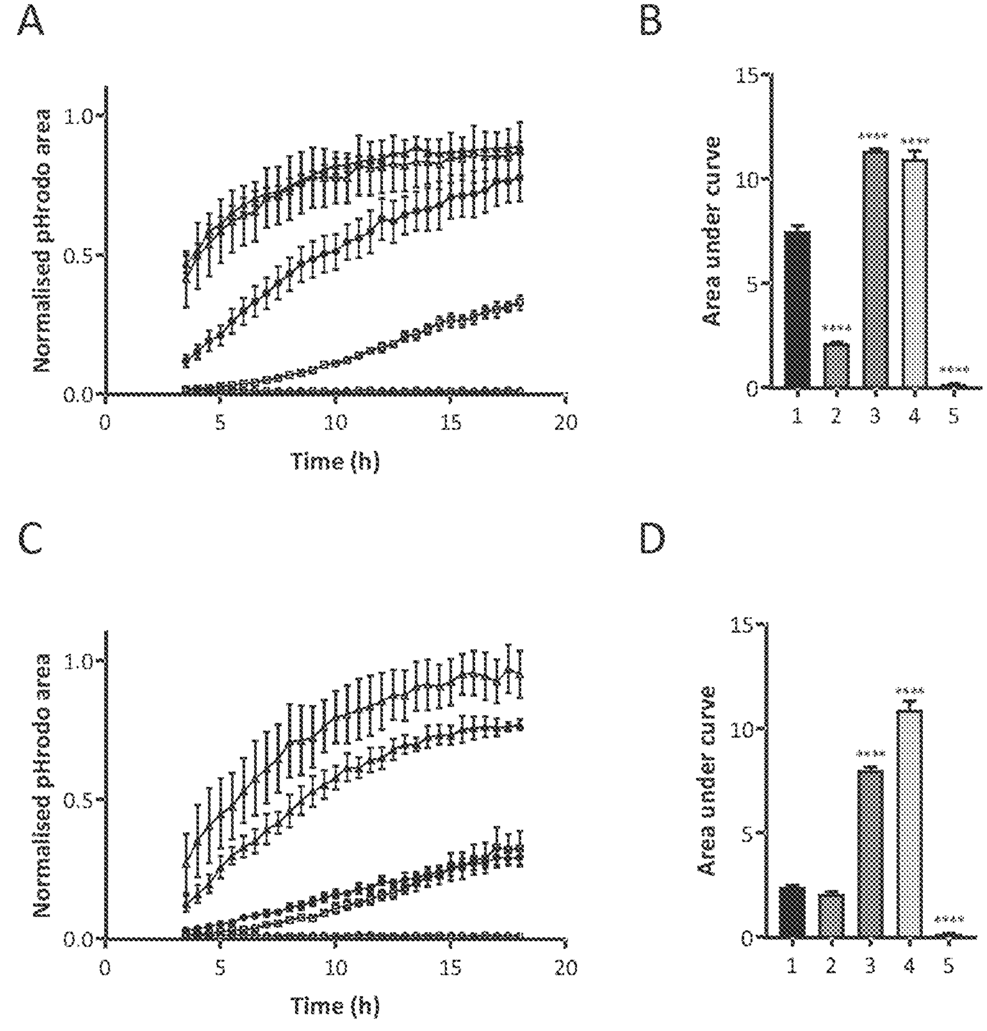

FIG. 15. Monoclonal anti-tau antibodies with effector function increase tau uptake by microglia. Rabbit IgG antibody clones #44 (Clone 2) (solid triangles, solid line) or #66 (Clone 1) (open triangles, solid line) or an isotype control rabbit IgG (open squares, solid line) were incubated with full length pHrodo-labelled monomeric 2N4R tau (A) or aggregated tau (B) before imaging on the OPERA-Phenix. pHrodo area per microglial area quantified after 3 h and subsequently every 30 mins increased steadily over time in isotype and no antibody (solid circles, dashed line) treatments, but was markedly increased in cells treated with anti-tau antibody clones. Negative control wells including no pHrodo-labelled tau are also shown (open circles, dashed line). Data are given as mean+/−SEM of n=4 wells from one representative experiment (A, C). Bar charts representing mean+/−SEM of area under curve calculated for no antibody (1), isotype control (2), clone #44 (clone 2) (3), clone #66 (clone 1) (4) and no pHrodo-labelled tau (5). **, p<0.0001; *, p<0.001; one-way ANOVA with Dunnett's multiple comparison test versus no antibody control (1).

Figure 16:
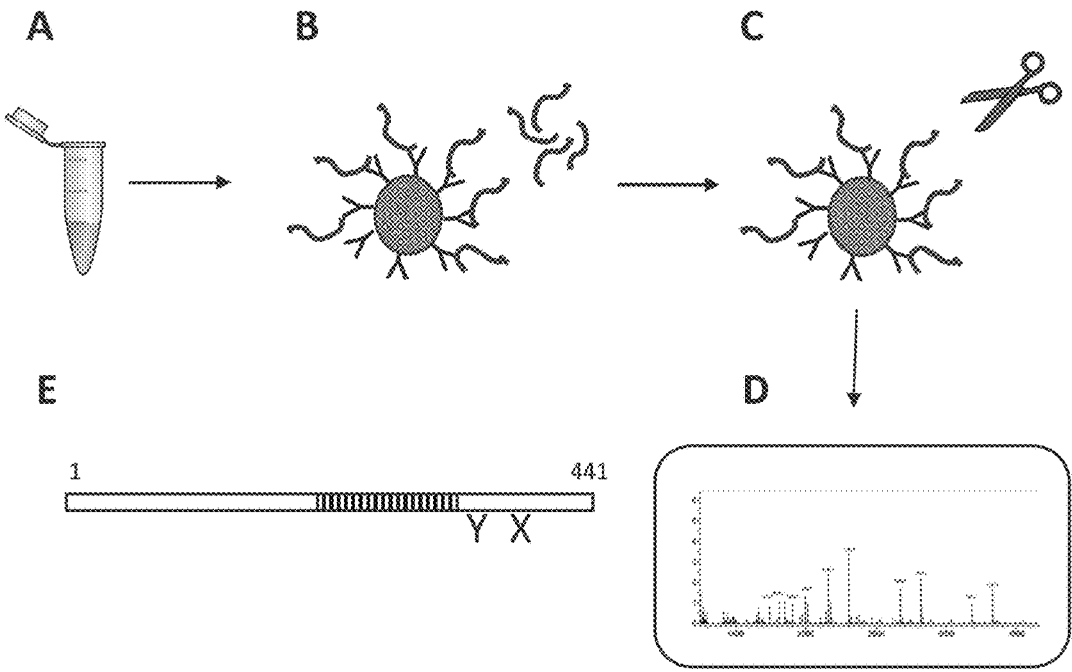

FIG. 16. Human AD CSF contains C-terminal tau. CSF samples from 16 individuals with clinically confirmed Alzheimer's disease were pooled (final volume 8.5 mL) (A). 150 ng of clone #44 (clone 2) IgG was bound and cross-linked to protein A-coated beads, and the beads used to immunopurify tau present in the pooled AD CSF, which contained the target epitope (B). Proteins were digested on the beads with trypsin (C), and eluted peptides resolved by mass spectrometry (D). A C-terminal tau peptide was identified in the pooled AD CSF (E, shown as 'X'), adjacent to the Gen2B epitope (shown as 'Y'), confirming the presence of C-terminal tau fragments in AD CSF.

Figure 17:
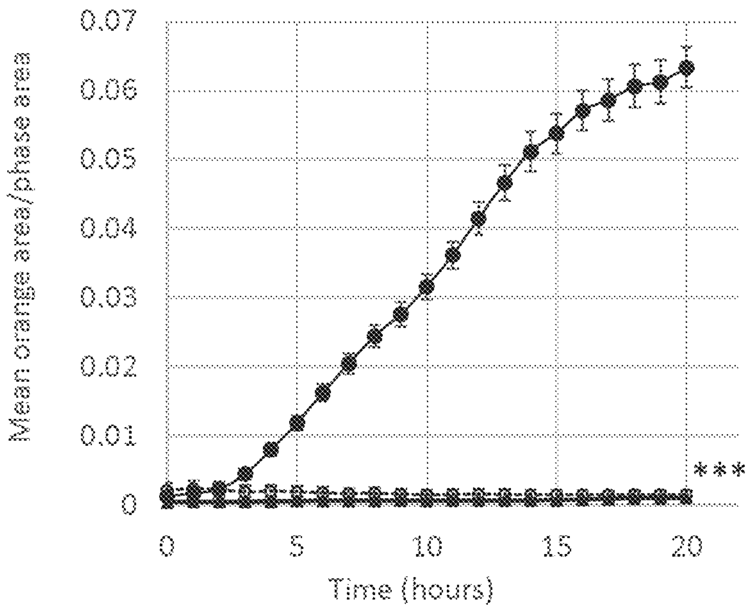
Figure 17:
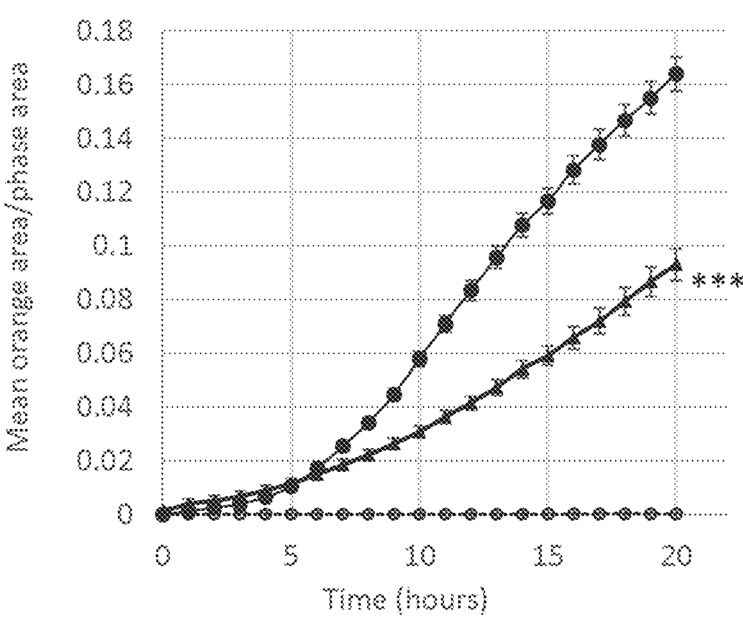

FIG. 17. Anti-tau rabbit IgG inhibited uptake of monomeric and aggregated tau by human iPSC-derived astrocytes. Antibody clone #44 (Clone 2) (solid triangles, solid line) was incubated with full length pHrodo-labelled monomeric 2N4R tau (A) or aggregated tau (B) before imaging on the Incucyte S3. Mean orange (pHrodo) area per microglial (phase) area quantified every 60 mins for 20 h increased over time in isotype and no antibody (solid circles, dashed line) treatments, but was significantly reduced in cells treated with anti-tau antibody clone #44. Negative control wells including no pHrodo-labelled tau are also shown (open circles, dashed line). Data are given as mean+/−SEM of n=4 wells from one representative experiment (A, B). ***, p<0.001; one-way ANOVA with Tukey's multiple comparison test versus no antibody control.

Figure 18:
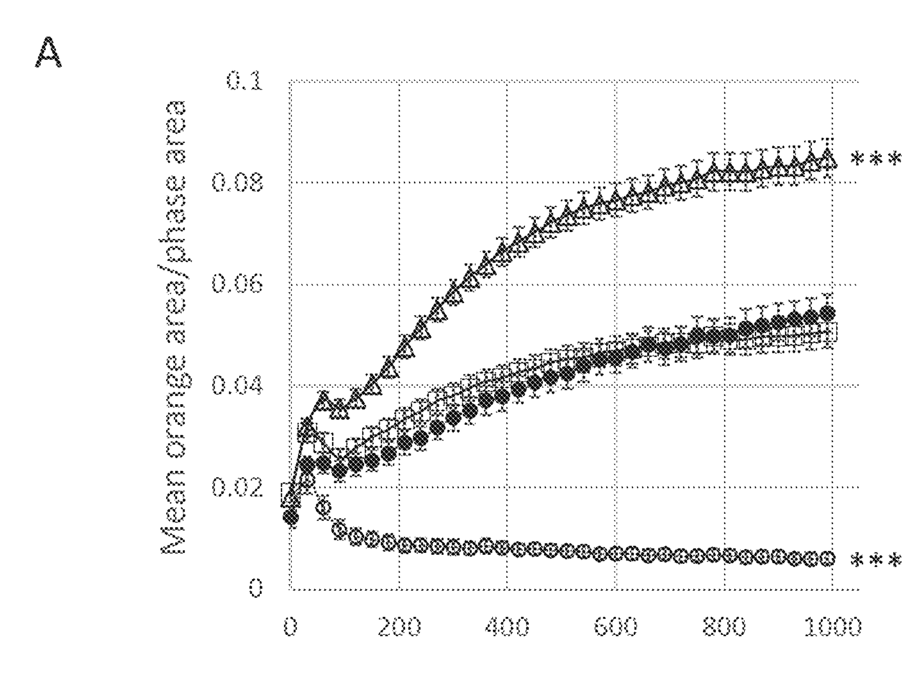
Figure 18:
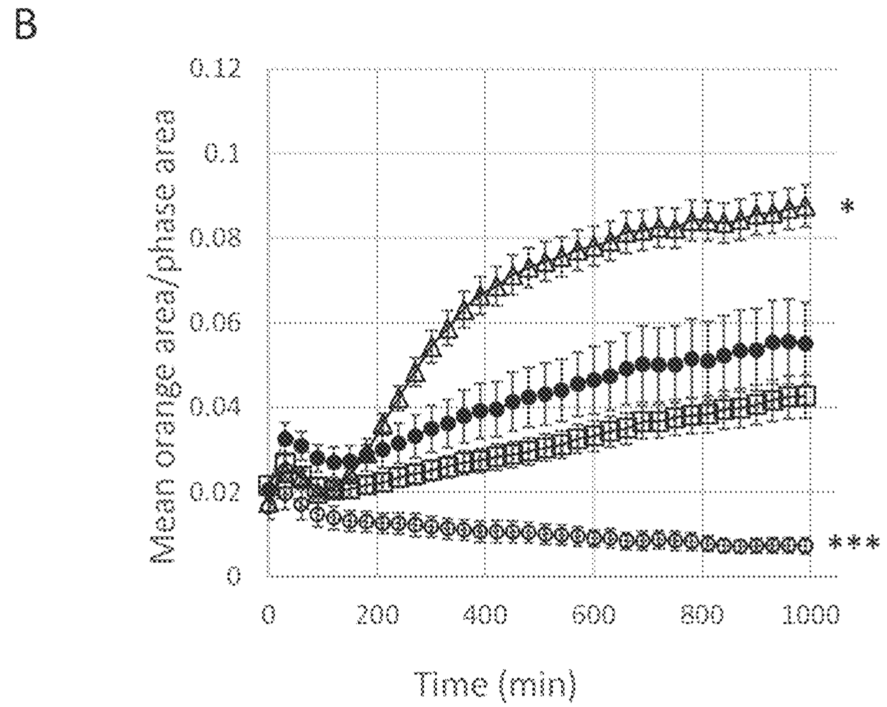

FIG. 18. Anti-tau chimeric human IgG1 increased uptake of monomeric and aggregated tau by human iPSC-derived microglia. Antibody clone #66 (Clone 1) (open triangles, solid line) or an isotype control hlgG (open squares, solid line) were incubated with full length pHrodo-labelled monomeric 2N4R tau (A) or aggregated tau (B) before imaging on the Incucyte S3. Mean orange (pHrodo) area per microglial (phase) area quantified every 30 mins for 16 h increased moderately over time in isotype and no antibody (solid circles, dashed line) treatments, but was significantly increased in cells treated with anti-tau antibody clones. Negative control wells including no pHrodo-labelled tau are also shown (open circles, dashed line). Data are given as mean+/−SEM of n=4 wells from one representative experiment (A, B). ***, p<0.001; *, p<0.05; one-way ANOVA with Tukey's multiple comparison test versus no antibody control.

Figure 19:
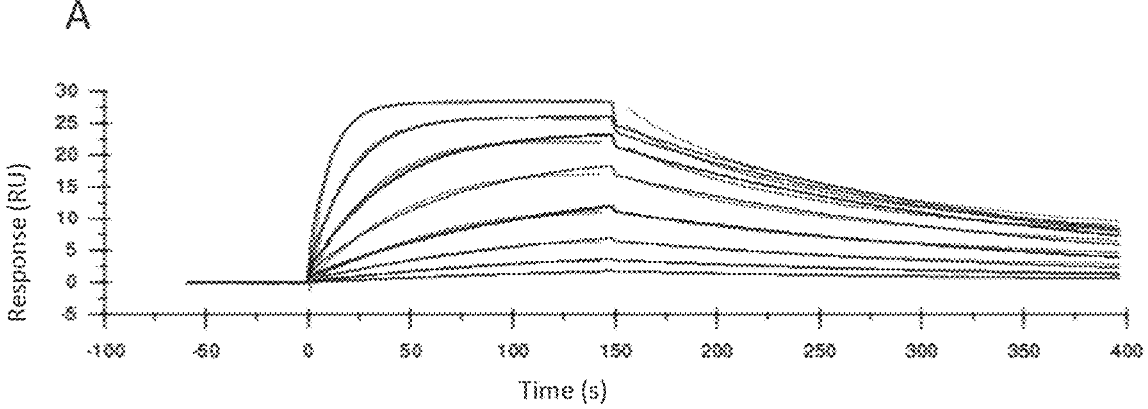
Figure 19:
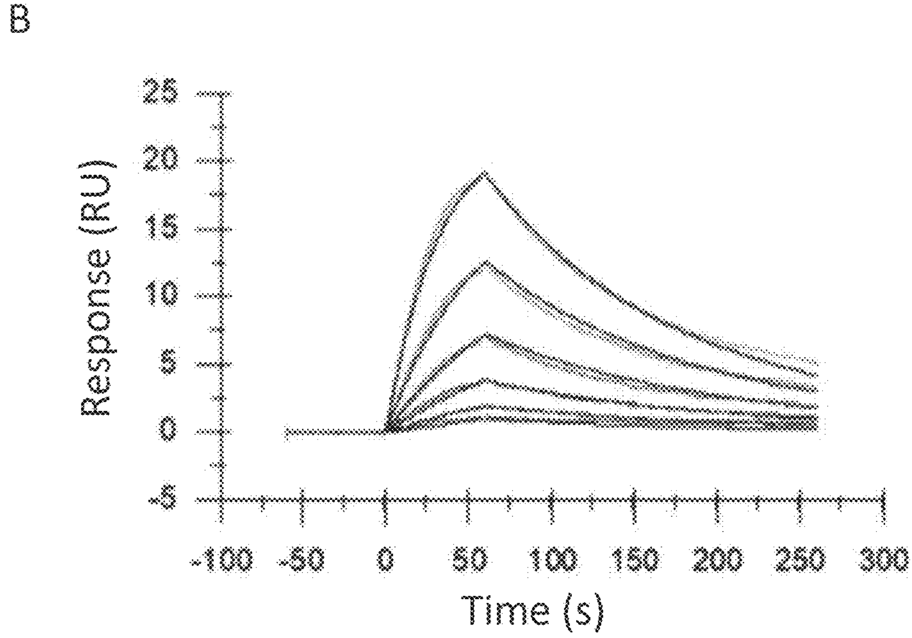

FIG. 19. Anti-tau IgG bind to tau with high affinity. Representative SPR binding curves show clone #66 (Clone 1) (A; 0.39 nM to 50 nM applied at 2-fold dilutions) and clone #44 (Clone 2) (B; 0.39 nM to 12.5 nM applied at 2-fold dilutions) binding to full length recombinant 2N4R tau. Experiments were run using a Biacore T200 with an association time of 150 s (#66) or 60 s (#44) and a dissociation time of 250 s (#66) or 200 s (#44).

Figure 20:
Figure 20:
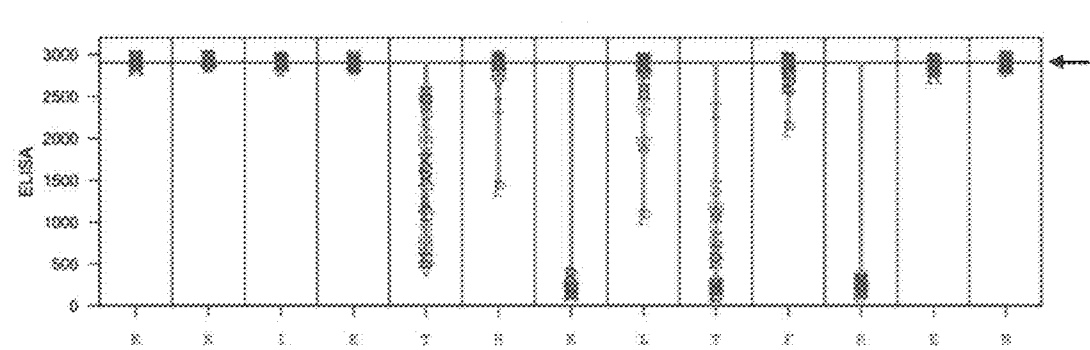
Figure 20:
Figure 20:
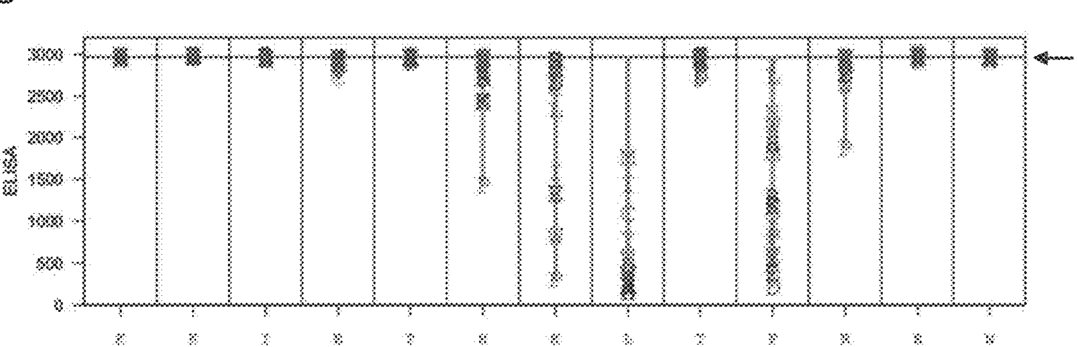
Figure 20:
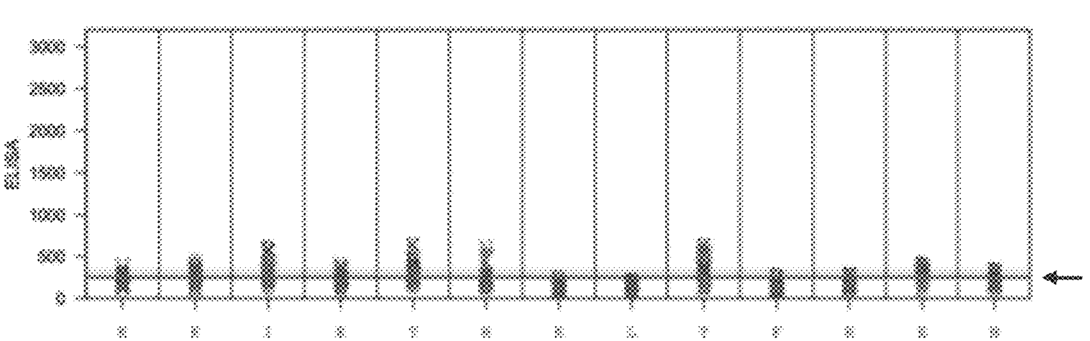

FIG. 20. Anti-tau antibodies bind to distinct epitopes within the immunogen sequence. Letter plot representations of epitope substitution scan analysis for antibody clones #44 (Clone 2; A) and #66 (Clone 1, B) highlight key residues required for binding to tau. Low level of binding of isotype control rabbit IgG to the peptide array (C) demonstrates that anti-tau antibody binding is CDR-specific. The linear peptides were generated bearing single amino acid substitutions at each position of the native lead peptide sequence, shown below the plot. Values obtained for replacements are indicated by the letter code for each replacement residue plotted at the height of the recorded value. Arrow indicates median value for the lead sequence.

Figure 21:
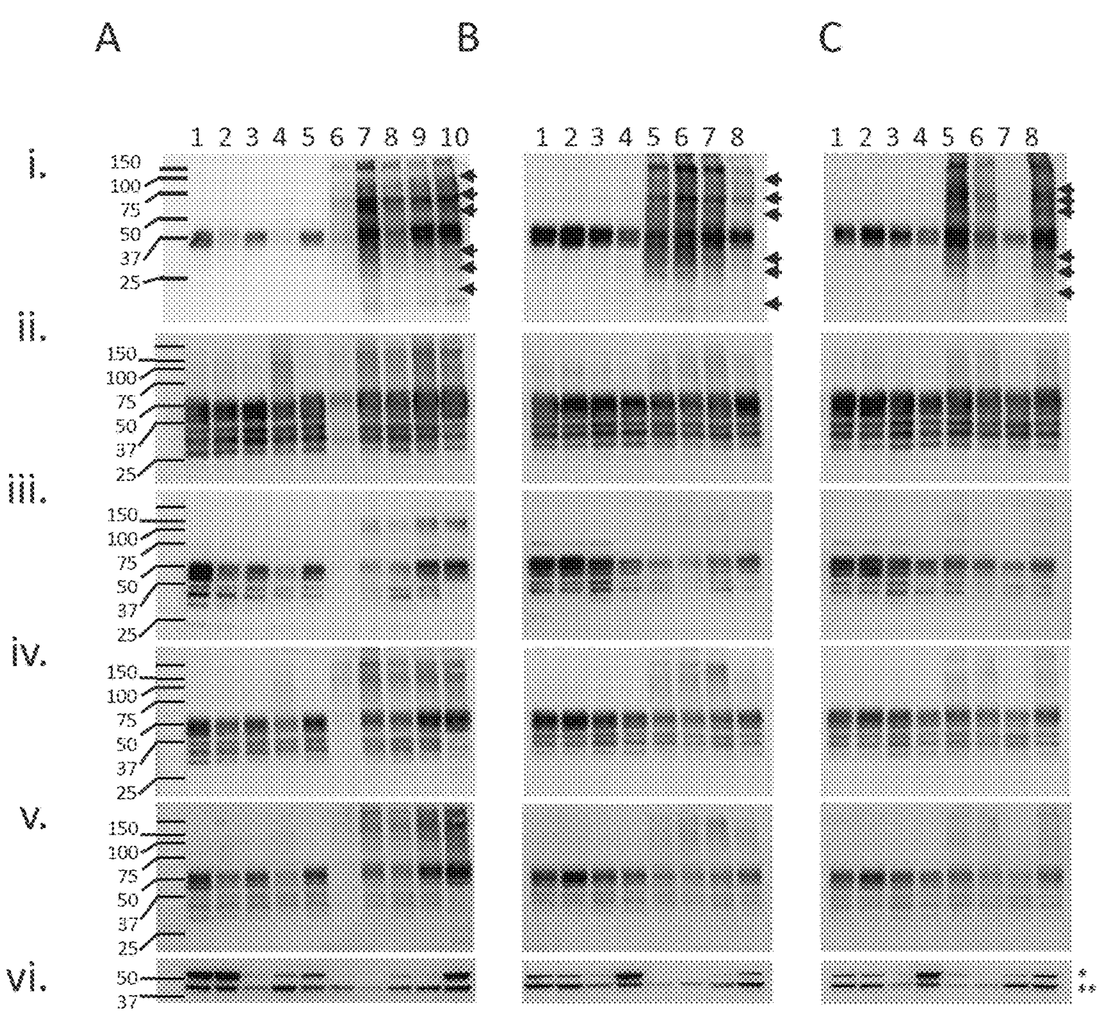

FIG. 21. Anti-tau antibodies detect increased levels of tau in familial Alzheimer's disease (AD), sporadic AD and dementia with Lewy bodies (DLB) compared to non-demented control (NDC) post-mortem cerebral cortex that are not detected by antibodies targeting N-terminal, mid-region or far C-terminal tau sequences. Western blots of cerebral cortex lysates from NDC (A, lanes 1-5; B-C, lanes 1-4); familial AD patients (A; lanes 6-10); sporadic AD patients (B, lanes 5-8) and DLB patients (C; lanes 5-8) are shown. Rabbit IgG clone #44 (i) detects multiple species corresponding to different forms of tau, with increased detection of both high and low MW species in Alzheimer's and DLB samples. Panels ii-vi show the same blots re-probed using commercially available anti-tau antibodies: Tau13 (ii.), HT7 (iii.), Tau5 (iv.) and Tau46 (v.), and highlight the clear disease specificity of tau species detected with antibodies targeting SEQ ID NO: 1, compared to N-terminal (Taul3), mid-region (HT7, Tau5) and far C-terminal (Tau46) antibodies. Arrows indicate tau species detected in disease samples, but not NDC, by antibodies targeting SEQ ID NO: 1 but not by commercially available antibodies. Actin (**) and neuronal tubulin (*) are shown (vi.) and were included to control for loading and post-mortem protein degradation respectively.

EXAMPLES

Example 1: Multiple Species of Tau Released from Familial Alzheimer's Disease Neuronal Cultures are not Found in Control Culture Supernatants (FIG. 1)

Multiple species of tau released from familial Alzheimer's disease (fAD) and fronto-temporal dementia (FTD) neuronal cultures are not found in non-demented control (NDC) neuronal culture supernatants. Tau was immunoprecipitated (IP) from neuronal cell culture supernatants from NDC, fAD-associated mutation, PSEN1 Y115C (PSEN) and FTD-associated mutation, MAPT IVS10+16 (MAPT) using commercial antibody, HT7 (Invitrogen, Carlsbad, CA, USA) or Tau13 (Santa-Cruz, Dallas, TX, USA), and compared to a mouse monoclonal IgG control. Western blots (FIG. 1) show detection of tau species following each immunoprecipitation, using anti-tau antibody (K9JA; Agilent, Santa Clara, CA, USA). Bands (highlighted in boxes 1-5, FIG. 1) were excised and analysed by mass spectrometry to identify the tau peptides that are enriched in disease-related secretomes. This analysis reveals an increase in the number of peptides from the microtubule binding domain (corresponding to amino acids 260-267 (SEQ ID NO: 9), 306-317 (SEQ ID NO: 10) and 354-369 (SEQ ID NO: 11) of 2N4R tau) and C-terminus (corresponding to amino acids 396-406 (SEQ ID NO: 12) of 2N4R tau) in disease-associated secretomes compared to those from NDC (Table 4). Data show that tau species including the microtubule binding domain and neighbouring C-terminal regions are secreted at higher levels from disease-associated neurons compared to NDC and may therefore represent pathological or toxic forms of tau.

1.1 Cell culture of human iPSC-derived neurons: Differentiation of human pluripotent stem cells (iPSC) to projection neuron cultures was carried out as described by Shi et al., Nature Neurosci. 15(3):477-86 (2012). iPSC lines from different genetic backgrounds were used: NDC (Shi et al., Nature Neurosci. 15(3):477-86; Shi et al. Nature Protocols 7(10): 1836-46 (2012)); trisomy 21 (TS21; Shi et al. Nature Protocols 7(10): 1836-46 (2012)); PSEN1 Y115C mutation (PSEN; Moore et al. Cell Rep 11(5): 689-96 (2015)); APP V7171 mutation (APP; Moore et al. Cell Rep 11(5): 689-96 (2015); MAPT IVS10+16 (MAPT; Sposito et al. Hum Mol Genet 24(18):5260-5269 (2015)). Cells were plated out for individual experiments at day 40 in vitro and maintained to day 60+(D60+), where days in vitro refers to days post-induction (as detailed later).

1.2 Immunoprecipitation and western blotting (FIG. 1): iPSC-derived neurons were cultured in 12 well plates (Corning, New York, USA) and matured to D60, after this, conditioned media was collected every 48 hours. Media was spun to remove cell debris and the supernatant stored at −20° C. Conditioned media was defrosted on ice and concentrated about 10-fold using Vivaspin 20, 10 kDa MWCO Polyethersulfone (Sigma, St Louise, Ml, USA). 1.2.1 Antibody conjugation: Dynabeads (Thermo Fisher Scientific, Waltham, MA, USA) were washed prior to incubation with 5 pg specified antibody for 10 mins. IgG antibody bead mix were then added to concentrated conditioned media and incubated overnight on a roller. Dynabeads were removed from the conditioned media and replaced with Tau13 (Abcam, Cambridge, UK) antibody bead mix and incubated for ~8 hours. Dynabeads were removed from the conditioned media and replaced with HT7 (Invitrogen, Carlsbad, CA, USA) antibody bead mix and incubated overnight. All beads were washed three times with 0.05% tween (PBS). 100 µl Laemlli lysis buffer were added to all beads and boiled for 10 mins. The supernatant was kept for running on SDS gel.

1.2.2 Western blotting: 20 µl of sample were loaded in 12% Mini-Protean TGX precast gel (Bio-Rad, Hercules, CA, USA) and transferred onto 0.2 µm PVDF membranes (GE Healthcare Life science, Chicago, IL, USA) at 200 mA for two hours at 4° C. Membranes were blocked in 5% dried skimmed milk (Marvel, Premier Foods, St Albans, UK), 0.1% Tween in PBS for 1 hour at room temperature (RT).

The protein-transferred membranes were probed overnight at RT with the primary antibody (at the concentration specified). Membranes were subsequently incubated with secondary antibody (goat anti-rabbit HRP) for 1 hour at RT.

1.3 Mass spectrometry: 20 µl of sample were loaded in 12% Mini-Protean TGX precast gel (Bio-Rad, Hercules, CA, USA). Gel were then incubated with EZBlue™ Gel Staining Reagent (Sigma, St Louis, MO, USA) for 4 hrs and then destained with $ddH_2O$ overnight. Bands that corresponded to tau by western blot analysis were excised from the colloidal blue SDS-PAGE. Excised bands were subjected to 20° C., in 200 µl 100 mM ammonium bicarbonate/50% acetonitrile, followed by, reduction with 5 mM tris(2-carboxyethyl) phosphine. Then alkylation by addition of iodoacetamide (25 mM final concentration; each incubation for 30 min per step) then liquid was removed. Gel pieces were dried in vacuum for 10 min and 25 µl 100 mM ammonium bicarbonate containing 5 µg/mL modified trypsin (Promega, Madison, WI, USA) was added (digestion for 17 h at 37° C.). Peptides were recovered and desalted using µC18 ZipTip (Millipore, Burlington, MA, USA) and eluted to a maldi target plate using 1-2 µl alpha-cyano-4-hydroxycinnamic acid matrix (Sigma, St Louis, MO, USA) in 50% acetonitrile/0.1% trifluoroacetic acid. Peptide masses were determined using a Bruker ultrafleXtreme Maldi mass spectrometer in reflectron mode and ms/ms fragmentation performed in LIFT mode. Data analysis was with FlexAnalysis, BioTools and ProteinScape software (Bruker, Billerica, MA, USA). Database searches of the combined mass fingerprint-ms/ms data were performed using Mascot (matrixscience.com). (Table 4)

TABLE 4

Peptide fragments identified by mass spectrometry in samples prepared from excised Bands 1-5 (FIG. 1) are summarised. The amino acid sequence and position within the full length 2N4R tau sequence (SEQ ID NO: 2) are given, with the number of times each peptide was identified.

| POSITION | SEQUENCE | BAND 1 | BAND 2 | BAND 3 | BAND 4 | BAND 5 |
|---|---|---|---|---|---|---|
| 6-23 | QEFEVMEDHAGTYGLGDR (SEQ ID NO: 3) | 2 | 2 | 2 | 2 | 3 |
| 181-190 | TPPSSGEPPK (SEQ ID NO: 4) | 0 | 5 | 0 | 4 | 0 |
| 195-209 | SGYSSPGSPGTPGSR (SEQ ID NO: 5) | 4 | 4 | 2 | 4 | 4 |
| 210-224 | SRTPSLPTPPTREPK (SEQ ID NO: 6) | 0 | 0 | 2 | 0 | 0 |
| 212-224 | TPSLPTPPTREPK (SEQ ID NO: 7) | 4 | 4 | 6 | 4 | 4 |
| 243-254 | LQTAPVPMPDLK (SEQ ID NO: 8) | 4 | 8 | 8 | 8 | 6 |
| 260-267 | IGSTENLK (SEQ ID NO: 9) | 0 | 4 | 0 | 0 | 0 |
| 306-317 | VQIVYKPVDLSK (SEQ ID NO: 10) | 2 | 4 | 4 | 3 | 2 |
| 354-369 | IGSLDNITHVPGGGNK (SEQ ID NO: 11) | 0 | 2 | 0 | 0 | 0 |
| 396-406 | SPVVSGDTSPR (SEQ ID NO: 12) | 0 | 4 | 4 | 4 | 4 |

Example 2: Peptide Synthesis

To further investigate the importance of microtubule binding domain/C-terminal containing tau fragments in neurodegenerative disease, novel antibodies targeting this region were generated. Peptide sequence KKIETHKLTFREN (SEQ ID NO: 1), corresponding to amino acids 369-381 of 2N4R tau was selected as an immunogen to generate rabbit IgG, for a number of reasons. First, the sequence adjoins the microtubule binding region (MTBR) but, unlike the MTBR itself, shows low identity with other regions within the tau protein and with microtubule binding protein family members. This increases the probability that antibodies generated bind specifically and selectively to the target region in tau, with low risk of cross-reactivity with other regions/proteins. Second, the absence of putative phosphorylation sites simplifies the interpretation of data obtained, in an area where tau phosphorylation has been linked to pathological outcomes (Augustinack et al., Acta Neuropathol 103(1): 26-35 (2002)). Antibodies targeting this peptide therefore enable the role of C-terminal containing tau species to be explored/targeted, without complication associated with binding to multiple sites and/or differential binding to phosphorylated/dephosphorylated tau. No similar antibodies are available in the public domain that meet these criteria. Antigenic peptide, [C]-KKIETHKLTFREN-amide (SEQ ID NO: 13) was synthesised by Cambridge Research Biochemicals (Billingham, UK) using standard techniques and shown to be >95% pure by HPLC. The peptide was assembled on a fully automated peptide synthesiser (Symphony, Protein Technologies, Tucson, AZ, USA) using standard Fmoc solid phase synthesis on Rink amide NovaPEG resin (100 μM). Standard Fmoc protected amino-acids (Novabiochem, San Diego, CA, USA) were coupled using PyBOP as activator and Diisopropylethylamine. Following assembly, the peptide was cleaved for 3 h using TFA/TIPS/Water/DODT (94.5/2.5/2.5/0.5). The volatiles were evaporated and the peptide was precipitated with cold ether. The precipitate was washed several times with ether and dried. Following analysis of the crude by RP-HPLC and MALDI (Waters Maldi Micro MX MS System, Milford, MA, USA), the peptide was purified on a C18 HPLC system (Gilson, Middleton, WI, USA) using a gradient of acetonitrile (5-35% over 30 min). Fractions were re-analysed by MALDI and pooled to give 2 mg of material at >95% purity after lyophilisation.

Peptides for immunisation were conjugated to Keyhole Limpet Haemocyanin (KLH) through the free thiol on the N-terminal cysteine, via a maleimidobenzoyl-N-hydroxysuccinimide ester (MBS) linker.

Peptides for use in the Single Plasma cell Interrogation (SPIN) protocol were conjugated to a biotinylated polymer using the free thiol on the N-terminal cysteine, using proprietary methods (Exonbio, San Diego, CA, USA).

Example 3: Immunisation of Rabbits with Target Immunogen 3.1: Immunisation of rabbits with target immunogen: One New Zealand White rabbit was used to generate the rabbit monoclonal antibodies. The rabbit was immunised with 200 pg (prepared at a 1 mg/mL dilution) purified KLH-conjugated peptide ([C]-KKIETHKLTFREN (SEQ ID NO: 13), corresponding to amino acids 369-381 of 2N4R tau) at day 0 (in Freund's complete adjuvant), then every 19 days to day 76 (in Freund's complete adjuvant). Adjuvant and antigen boosts were given (i.p.) on day 94 and 97 respectively before final bleeds were taken on day 104 and antisera collected using standard methods (Hancock & O'Reilly Methods Mol Biol 295:27-40 (2005)).

Animal husbandry and the procedures used complied with the Animal Welfare Act, 1966 (US Animal and Plant Health Inspection Service).

3.2: Peptide ELISA (FIG. 2): In order to confirm the generation of a robust immune response, serum was tested for immunoreactivity to the immobilised target antigen at various time points post-immunisation. Serum taken at day 76 post-immunisation showed immunoreactivity to the linear peptide target at dilutions of 1:1000-1:1000,000, indicative of IgG titres sufficient to proceed to monoclonal antibody isolation (FIG. 2).

ELISA plates were coated with antigen (non-conjugated antigen peptide (Antigen peptide ([C]-KKIETHKLTFREN-amide (SEQ ID NO: 13); 2 pg/well in 1×PBS) overnight at 4° C. Antigen was removed from wells and the plates were blocked for 1 hour at RT with 5% dried milk in 1×PBS. Blocking solution was removed, 100 μL of diluted serum (diluted in 1% BSA/1×PBS) was added to relevant wells, and plates were incubated for 1 hour at RT with gentle shaking. Plates were then washed four times with PBS/0.1% Tween (PBST). Anti-rabbit IgG-HRP antibody (Sigma, St Louis, MO, USA), diluted 1:10,000 in 1% BSA in PBS, was added to each well and plates were incubated for 30 min at RT with gentle shaking before being washed four times with PBST. 50 μL 3,3',5,5'-tetramethylbenzidine (TMB) ELISA solution was added to each well and plates were incubated for 15 mins at RT, an equal volume of 1 M sulfuric acid was added to each well and OD was measured at 450 nm.

Example 4: Isolation of Monoclonal IgG Specific for the Target Epitope 96 individual antigen-specific plasma cells were identified and isolated using the target immunogen by Exonbio using proprietary methods (Exonbio, San Diego, CA, USA).

Splenocytes were isolated from the spleen of the immunised rabbit with Ficoll gradient (1.084) and were stained with plasma cell marker and biotin-conjugated antigen. Antigen-specific plasma cells were isolated and sorted into 96-well plates at one cell per well. Variable regions of antibody heavy and light chains were amplified individually by single cell polymerase chain reaction (PCR). Amplified heavy and light chains were then cloned into pRab293 plasmid and expressed in HEK293F suspension cells in serum-free medium using Invitrogen (Carlsbad, CA, USA) 293fectin transfection reagent, as per the manufacturer's instructions.

TABLE 5

| Heavy and Light Chain amino acid CDR sequences for Clones 1-17 | | | | | | | | |
|---|---|---|---|---|---|---|---|---|
| | | Anti- | HC sequence | | | LC sequence | | |
| Clone | Code | body | CDR1 | CDR2 | CDR3 | CDR1 | CDR2 | CDR3 |
| 1 | #66 | B9 | SNAMI (SEQ ID NO: 14) | NIGTHGTTYYASWAKG (SEQ ID NO: 15) | GDI (SEQ ID NO: 16) | QASQSVDDNNNLA (SEQ ID NO: 17) | EASTLAS (SEQ ID NO: 18) | LGEFSCSSADCVV (SEQ ID NO: 19) |
| 2 | #44 | D6 | SYAMA (SEQ ID NO: 20) | CIDRRGGTFYASWVKG (SEQ ID NO: 21) | DSGAFDP (SEQ ID NO: 22) | QASQSVYDNYLA (SEQ ID NO: 23) | AASNLAS (SEQ ID NO: 24) | LGEFSCTTTDCNV (SEQ ID NO: 25) |
| 3 | #12 | D2 | SYAVG (SEQ ID NO: 26) | CIDSRDSKFYASWAKG (SEQ ID NO: 27) | DSGAFNP (SEQ ID NO: 28) | QASQSVYDNYLA (SEQ ID NO: 29) | AVSNLAS (SEQ ID NO: 30) | LGEFYCSSIDCNA (SEQ ID NO: 31) |
| 4 | #45 | E6 | SYAVG (SEQ ID NO: 32) | CIDGRDSAFYASWAKG (SEQ ID NO: 33) | DSGAFNP (SEQ ID NO: 34) | QASQSVYDNYLS (SEQ ID NO: 35) | AVSNLAS (SEQ ID NO: 36) | LGEFYCSSIDCNA (SEQ ID NO: 37) |
| 5 | #61 | E8 | TYAMA (SEQ ID NO: 38) | CIDRRGGTFYASWAKG (SEQ ID NO: 39) | DSGAFDP (SEQ ID NO: 40) | QASQSVYDNYLA (SEQ ID NO: 41) | AASNLAS (SEQ ID NO: 42) | LGEFSCTTTDCNV (SEQ ID NO: 43) |
| 6 | #34 | B5 | KNAMI (SEQ ID NO: 44) | NIGTRGTTYYASWTKG (SEQ ID NO: 45) | GDI (SEQ ID NO: 46) | QSSQSVNNNDLA (SEQ ID NO: 47) | EASTLAS (SEQ ID NO: 48) | LGEFSCSSADCVA (SEQ ID NO: 49) |
| 7 | #43 | C6 | SYAMS (SEQ ID NO: 50) | CIDSRGSVYYASWAKG (SEQ ID NO: 51) | DSGAFDP (SEQ ID NO: 52) | QASQSVYDNYLS (SEQ ID NO: 53) | AASNLAS (SEQ ID NO: 54) | LGEFYCSSMDCNA (SEQ ID NO: 55) |
| 8 | #41 | A6 | SNAMI (SEQ ID NO: 56) | NIGTHGTTYYASWAKG (SEQ ID NO: 57) | GDI (SEQ ID NO: 58) | QASQSVDNNNNLA (SEQ ID NO: 59) | EASTLAS (SEQ ID NO: 60) | LGEFSCSSADCVA (SEQ ID NO: 61) |
| 9 | #87 | G11 | SYAVG (SEQ ID NO: 62) | CIDSHDNTFYASWAKG (SEQ ID NO: 63) | DSGAFNP (SEQ ID NO: 64) | QASQSVYDNYLS (SEQ ID NO: 65) | AVSNLAS (SEQ ID NO: 66) | LGEFYCSSIDCNA (SEQ ID NO: 67) |
| 10 | #65 | A9 | SNAMI (SEQ ID NO: 68) | NIGTHGTTYYASWSKG (SEQ ID NO: 69) | GDI (SEQ ID NO: 70) | QASQSVDNNNNLA (SEQ ID NO: 71) | EASTLAS (SEQ ID NO: 72) | LGEFSCSSADCVA (SEQ ID NO: 73) |
| 11 | #47 | G6 | NYAMA (SEQ ID NO: 74) | CIDRRGGTFYASWAKG (SEQ ID NO: 75) | DSGAFDP (SEQ ID NO: 76) | QASQSVYDNYLA (SEQ ID NO: 77) | AASNLAS (SEQ ID NO: 78) | LGEFSCTTTDCNV (SEQ ID NO: 79) |
| 12 | #5 | E1 | SYAVG (SEQ ID NO: 80) | CIDSHDNTFYASWAKS (SEQ ID NO: 81) | DSGAFNP (SEQ ID NO: 82) | QASQSVYDNYLS (SEQ ID NO: 83) | AVSNLAS (SEQ ID NO: 84) | LGEFYCSSIDCNA (SEQ ID NO: 85) |
| 13 | #37 | E5 | SYAMG (SEQ ID NO: 86) | CIDRRGATFYASWAKG (SEQ ID NO: 87) | DSGAFDP (SEQ ID NO: 88) | QASQSVYDNYLS (SEQ ID NO: 89) | AASNLAS (SEQ ID NO: 90) | LGEFSCTTTDCNV (SEQ ID NO: 91) |
| 14 | #56 | H7 | SYAMG (SEQ ID NO: 92) | CIDRRGGTFYASWAKG (SEQ ID NO: 93) | DSGAFDP (SEQ ID NO: 94) | QASQSVYDNYLA (SEQ ID NO: 95) | AASNLAS (SEQ ID NO: 96) | LGEFSCTTTDCNV (SEQ ID NO: 97) |
| 15 | #77 | E10 | SYAMT (SEQ ID NO: 98) | CIDTGGSAYYASWAKG (SEQ ID NO: 99) | DTGAFDP (SEQ ID NO: 100) | QASQSVYDNNLA (SEQ ID NO: 101) | AASNLPS (SEQ ID NO: 102) | LGEFSCSSTDCNA (SEQ ID NO: 103) |
| 16 | #10 | B2 | SYAVG (SEQ ID NO: 104) | CIDSRDSAFYASWAKG (SEQ ID NO: 105) | DSGAFNP (SEQ ID NO: 106) | QASQSVYDNYLS (SEQ ID NO: 107) | AVSNLAS (SEQ ID NO: 108) | LGEFYCSSIDCNA (SEQ ID NO: 109) |
| 17 | #69 | E9 | IYAMG (SEQ ID NO: 110) | CIDRRGATFYATWAKG (SEQ ID NO: 111) | DSGAFDP (SEQ ID NO: 112) | QASQSVYDNNLA (SEQ ID NO: 113) | AASNLAS (SEQ ID NO: 114) | LGEFSCTTTDCNV (SEQ ID NO: 115) |

Example 5: Transiently Expressed IgG Bind to the Isolated Peptide Immunogen (FIG. 3)

Individual rabbit IgG clones were transiently expressed in HEK293F cells in order to generate IgG samples for in vitro testing. Supernatants containing single IgG clones were tested for ability to bind to both the short peptide immunogen ([C]-KKIETHKLTFREN-amide; SEQ ID NO: 13) and full length 2N4R recombinant tau (SEQ ID NO: 2) (FIG. 3). 23 clones were found to bind full length tau with OD>0.3 and were prioritised for sequencing. Seventeen unique clones were identified and expressed (Table 5). Data demonstrate the utility of short peptide immunogen ([C]-KKIETHKLTFREN-amide) for the generation of IgG able to bind to full length recombinant 2N4R tau; and demonstrate the ability of the 17 prioritised clones to bind to both the immunogen and full length 2N4R tau.

5.1 Transient Expression of IgG in HEK Cells

Individual rabbit IgG clones were transiently expressed in HEK293F cells in order to generate IgG samples for in vitro testing. HEK293F cells cultured in suspension were transiently transfected with constructs in pRab293 plasmid using 293fectin transfection reagent (Invitrogen, Carlsbad, CA, USA) as per the manufacturer's instructions.

Supernatants were collected 7 days post-transfection. Antibodies were purified using a protein A column (25 mL resin) on an AKTA chromatography system (GE Healthcare, Chicago, IL, USA) and standard methods. Briefly, Protein A column was loaded with supernatant at 5 mL/min, then washed with PBS (5×total column volume). The protein peak was collected and dialysed in PBS overnight at 4° C.

For generation of mg quantities of IgG, 300 mL-1 litre HEK293F cells were transiently transfected and IgG was purified from culture media 7 days post-transfection using a protein A column, as above.

5.2 Peptide ELISA

ELISA plates were coated with antigen (non-conjugated antigen peptide (Antigen peptide ([C]-KKIETHKLTFREN-amide (SEQ ID NO: 13)) or full length 2N4R tau (SEQ ID NO: 2), 100 ng/well; or 1% BSA in 1×TBS) in 1×carbonate-bicarbonate buffer for 1 hour at 37° C. Antigen was removed from wells and the plates were then blocked for 1 hour at RT with 5% dried milk in 1×TBS. Blocking solution was removed, HEK293F cell supernatant (10 μg/mL, to 0.0001 μg/mL in 1% BSA/1×TBS) was added to relevant wells, and plates were incubated for 1 hour at RT with gentle shaking. Plates were then washed four times with TBS/0.1% Tween (TBST). Anti-rabbit IgG-HRP antibody (Sigma, St Louis, MO, USA), diluted 1:5000 in 5% milk/TBS, was added to each well and plates were incubated for 1 hour at RT with gentle shaking before being washed four times with TBST. 3,3',5,5'-tetramethylbenzidine (TMB) ELISA solution was added to each well and plates were incubated for 15 mins at RT. An equal volume of 1 M sulfuric acid was added to each well and OD was measured at 450 nm.

Example 6: Monoclonal Antibodies Detect Full-Length Recombinant Tau by ELISA in a Concentration-Dependent Manner. (FIG. 4)

Anti-tau rabbit IgG clones #66 (Clone 1) and #44 (Clone 2) bind to full length recombinant 2N4R tau (SEQ ID NO: 2), immobilised on an ELISA plate, in a concentration-dependent manner, with half maximal ELISA signal observed at 0.82 nM [0.7 to 0.95 nM] and 1.05 nM [0.96 to 1.15 nM] respectively (mean and 95% confidence intervals from n=2 wells in a single experiment are given). Data demonstrate high affinity binding of both clones to full length tau.

6.1 ELISA analyses (FIG. 4): ELISA plates were coated with antigen (full length 2N4R tau, 100 ng/well; or 1% BSA in 1×TBS) in 1× carbonate-bicarbonate buffer for 1 hour at 37° C. Antigen was removed from wells and the plates were then blocked for 1 hour at RT with 5% dried milk in 1×TBS (200 μL/well). Blocking solution was removed, diluted IgG (10 μg/mL, to 0.0001 μg/mL in 1% BSA/1×TBS) was added to relevant wells, and plates were incubated for 1 hour at RT with gentle shaking. Plates were then washed four times with TBS/0.1% Tween (TBST). Anti-rabbit IgG-HRP antibody (Sigma, St Louis, MO, USA), diluted 1:5000 in 5% milk/TBS, was added to each well and plates were incubated for 1 hour at RT with gentle shaking before being washed four times with TBST. 25 μl 3,3',5,5'-tetramethylbenzidine (TMB) ELISA solution was added to each well and plates were incubated for 15 mins at RT, an equal volume of 1 M sulfuric acid was added to each well and OD was measured at 450 nm.

Data were plotted as log concentration of IgG against ELISA signal (OD) and $EC_{50}$ values were calculated using a four parameter logistic equation with variable slope using GraphPad Prism (GraphPad Software Inc, La Jolla, CA, USA).

Example 7: Monoclonal Anti-Tau Antibodies Detect Tau in Human iPSC-Derived Neuronal Cultures (FIGS. 5, 6)

Western blots demonstrate the ability of anti-tau IgG to detect recombinant and natively expressed tau. HEK293F cell-derived supernatants (generated as per Example 5.1) containing rabbit IgG clones #12 (Clone 3), #44 (Clone 2), #45 (clone 4) or #66 (Clone 1) detected full length recombinant 2N4R tau (SEQ ID NO: 2) (rPeptide, Watkinsville, GA, USA) as a dominant band at ~60 kD (FIG. 5). All clones tested were able to detect 22 ng tau loaded into a single lane (FIG. 5, lane 2). All 4 clones detected a dominant band at ~50 kD in human iPSC-derived neuronal lysates. Treatment of neuronal lysates with lambda phosphatase to dephosphorylate proteins, decreased the apparent molecular weight of detected tau species detected in neuronal lysates (consistent with successful dephosphorylation), but did not impact the ability of antibodies to detect natively expressed tau. Data demonstrate that all 4 IgG clones tested bind equally well to phosphorylated and dephosphorylated tau samples and are able to detect both recombinant and natively expressed tau by western blot.

Purified clones #44 (Clone 2) and #66 (Clone 1) IgG detect tau in human iPSC-derived neurons from NDC, disease-AD-associated (PSEN Y115C, trisomy 21) and FTD-associated (MAPT IVS10+16) genetic backgrounds (FIG. 6). A dominant band is detected at ~50 kD in each neuronal sample. Commercially available antibody, HT7 (raised against an epitope corresponding to amino acids 159-163 of 2N4R tau; Invitrogen, Carlsbad, CA, USA) also detected a dominant band at ~50 kD when used to reprobe the blots, consistent with this representing full length tau. Data show that tau present intracellularly in human iPSC-derived neurons in culture can be detected by antibodies targeting the epitope corresponding to amino acids 369-381

(SEQ ID NO: 1) of 2N4R tau (SEQ ID NO: 2) (FIG. 6). 7.1. Protein extraction: iPSC-derived neuronal cultures were lysed using RIPA buffer (Sigma, St Louis, MO, USA) supplemented with protease inhibitors (cOmplete Mini, EDTA free, Roche Diagnostics, Rotkreux, Switzerland). Protein concentration was measured with Pierce BCA Protein Assay Kit (Thermo Fisher Scientific, Waltham, MA, USA), and where specified, brain lysates were treated with lambda protein phosphatase (I-PP); (New England Biolabs, Ipswich, MA, USA), according to manufacturer's instructions.

7.2 Western blotting: 40 μg protein in 20 μL total volume (unless otherwise stated) were loaded on a 12% Mini-Protean TGX precast gel (Bio-Rad, Hercules, CA, USA) and transferred onto 0.2 μm PVDF membranes (GE Healthcare Life science, Chicago, IL, USA) at 200 mA for two hours at 4° C. Membranes were incubated in blocking solution (5% dried skimmed milk, 0.1% Tween in PBS) for 1 hour at RT.

7.3 Antibody incubation: The protein-transferred membranes were probed overnight at RT with the primary antibody (at the concentration specified). Membranes were subsequently incubated with secondary antibody (anti-rabbit-HRP (Sigma, St Louis, MO, USA) 1:1000) for 1 hour at RT.

7.4 Membrane visualization: Each membrane was detected using enhanced chemiluminescence (ECL) western blotting detection reagent (GE Healthcare Life Science, Chicago, IL, USA) and visualized using ImageQuant LAS 4000 (GE Healthcare Life Science, Chicago, IL, USA).

7.5 Beta-Actin normalization: Beta-actin was included as a loading control. After imaging the first antibody complex was removed from PVDF membranes using Restore PLUS Western Blot Stripping Buffer (Thermo Fisher Scientific, Waltham, MA, USA) for 25 minutes at RT. The membranes were incubated with blocking solution for 1 hour at RT. Each membrane was probed with mouse monoclonal anti-beta-Actin (Sigma, St Louis MO, USA; 1:1000), or TuJ1 primary antibody (R&D Systems, Minneapolis, MN, USA; 1:1000) and then incubated with goat anti-mouse IgG-peroxidase secondary antibody (Sigma, St Louis, MO, USA; 1:2000). Both antibodies were incubated for 1 hour at RT consecutively.

Example 8: Monoclonal Anti-Tau Antibodies Detect Increased Levels of Tau in Familial Alzheimer's Disease (fAD) Compared to Non-Demented Control Post-Mortem Brain (FIG. 7, 8)

Western blots were run using brain lysates from NDC and Alzheimer's disease patients. HEK293F cell-derived supernatants containing IgG clones #12 (Clone 3), #44 (Clone 2), #45 (Clone 4) or #66 (Clone 1) detect tau in human post-mortem brain samples (FIG. 7). All 4 clones detect increased levels of tau in AD compared to NDC brain samples, including multiple high (>75 kD) and low (<40 kD) molecular weight species that are absent in the NDC samples tested. Data demonstrate that 4 distinct IgG clones targeting the sequence corresponding to amino acids 369-381 of 2N4R tau (SEQ ID NO: 1) all detect a similar pattern of disease-specific high and low molecular weight species of tau in AD brain lysates, in addition to bands at ~50 kD that are present in NDC and disease samples. This suggests that observations made are generalisable to all antibodies binding to SEQ ID NO: 1.

When a broader selection of post-mortem samples was assessed, purified clone #44 (Clone 2) and #66 (Clone 1) IgG again detected multiple species corresponding to different forms of tau, with increased detection of both high and low molecular weight species in Alzheimer's samples (FIG. 8). Actin and neuronal tubulin were included to control for loading and post-mortem protein degradation respectively, demonstrate that increased detection of tau in AD samples is not a result of increased protein loading or reduced degradation but rather reflects an increase in the abundance of C-terminal tau containing species in AD brain compared to NDC. Notably, antibodies targeting SEQ ID NO: 1 detected a distinct pattern of tau species in post-mortem brain samples that were not detected by commercially available anti-mid-region tau antibody, HT7. These include both low and high MW species that are clearly increased in abundance in AD compared to NDC brain samples (FIG. 8, arrows). Low molecular weight species detected by the HT7 antibody are relatively unchanged or reduced in disease compared to non-disease brains. This suggests that disease-specific tau species are detected by the novel antibodies described here, that are not detected by commercially available mid-region antibodies. Data confirm the presence and increased abundance of tau species containing the epitope of interest in Alzheimer's disease brain compared to controls.

8.1 Western blot: See Example 7.1 for detailed methods.

8.2 Human brain samples: Human post-mortem brain samples were obtained from the Kings College London Neurodegenerative Diseases Brain Bank. All work was ethically approved and informed consent was obtained prior to brain donation. Alzheimer's disease brain samples were from the frontal cortex of individuals with familial Alzheimer's disease (PSEN1 mutations; summarised in Table 6). Non-demented control brain samples were from age-matched individuals who showed no clinical signs of dementia. Causes of death for the control individuals were: lung carcinoma (1), coronary artery occlusion (2), lung cancer (3), acute hepatic failure (4), metastatic prostate cancer (5); none of which would be predicted to impact tau levels/species detected post-mortem.

TABLE 6

A summary of the known mutations associated with familial Alzheimer's disease present in the AD brain samples.

| Sample number | Disease-associated mutation |
| --- | --- |
| AD6 | PS1 (E280G) |
| AD7 | PS1 mutation |
| AD8 | PS1 mutation |
| AD9 | PS1 Delta4 truncation |
| AD10 | PS1 mutation |

8.3 Protein extraction: Post-mortem brain samples were provided by the brain bank as homogenised tissue (1 $cm^3$ homogenised in 4 mL). Homogenised PM brain samples were cleared by centrifugation at full speed, for 30 minutes at 4° C. Protein concentration of cleared lysates was measured with Pierce BCA Protein Assay Kit (Thermo Fisher Scientific, Waltham, MA, USA).

Example 9: Monoclonal Anti-Tau Antibodies Detect Increased Levels of Tau in Sporadic Alzheimer's Disease (AD), and Dementia with Lewy Bodies (DLB) Compared to Non-Demented Control Post-Mortem Brain (FIG. 9)

In order to extend the dataset beyond familial forms of AD, post-mortem brain samples from sporadic AD and DLB patients were assessed by western blot. Clone #66 (clone 1) IgG detected increased levels of both high and low molecular weight tau species in all disease associated samples when compared to NDC (FIG. 9, arrows). As previously described (Example 8), commercially available mid-region tau antibodies, HT7 and BT2 (ThermoFisher, Waltham, MA), detected a range of predominantly lower molecular weight (<40 kD) tau species in all samples (in addition to full length tau at ~50 kD), with no detectable disease-associated increases. Actin and neuronal tubulin controls confirm that changes in tau levels are not due to variations in protein and/or neuronal levels in samples shown. Data demonstrate the presence and increased abundance of tau species containing the epitope of interest (SEQ ID NO: 1) in sporadic AD and tauopathy brains, in addition to familial AD. This suggests that these species may be a general feature of AD and tauopathy and that therapeutics targeting this region may have broad utility in treating a range of tauopathies, in addition to both sporadic and familial forms of AD.

9.1 Western blot: See Example 7.1 for detailed methods.

9.2 Human brain samples: See Example 8 for provenance of human post-mortem brain samples. All samples were from the frontal cortex of individuals with clinically and pathologically confirmed sporadic Alzheimer's disease (Braak stage 6) or DLB. Non-demented control brain samples were from age-matched individuals who showed no clinical signs of dementia or pathological signs of AD/tauopathy (Braak stage 0). Causes of death for the control individuals, where noted, would not be predicted to impact tau levels/species detected post-mortem.

9.3 Protein extraction: Post-mortem brain samples were prepared as described in Example 8.

Example 10: Anti-Tau IgG Detect Natively Expressed Tau in Human iPSC-Derived Neuronal Cultures by Immunocytochemistry. (FIG. 10)

Figure 10:
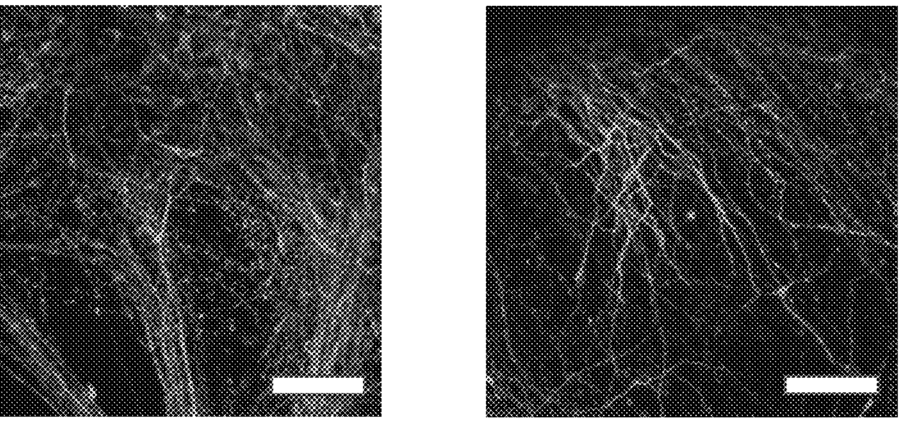

Clone #66 (Clone 1) was used to visualise tau expression in NDC and FTD-associated (MAPT IVS10+16) iPSC-derived neurons (day 50+) by immunocytochemistry (FIG. 10). Staining patterns are consistent with a predominantly axonal localisation of tau, with low levels of background. Data demonstrate that clone #66 (clone 1) is able to detect natively expressed tau, in situ in human neurons and is a useful tool for histological analyses.

10.1 Production of human iPSC-derived cerebral cortex neurons: iPSC-derived neurons (generated as described in Section 1.1) were plated in 96 well imaging plates (Corning, New York, USA; or Ibidi, Martinsried, Germany).

10.2 Culture Fixation: Cultures were washed with 1× Hanks Balanced Salt Solution and fixed with 4% paraformaldehyde (PFA) at RT for 20 minutes. PFA was then removed, and cultures were washed twice with PBS prior to labelling.

10.3 Fluorescent labelling of fixed cultures: Cultures were permeabilised by incubation with 0.1% Triton X-100 in PBS (PBS-Tr) for 1 h at RT. Cultures were incubated in blocking solution (200 μL/well; PBS/2% BSA/0.1% Triton X-100) at RT for 2 h, then with clone #66 (Clone 1) (at 1:200 dilution, in blocking solution overnight at 4° C. The following day, cultures were washed 3× in 0.1% PBS-Tr followed by incubation with species-specific Alexa Fluor-conjugated secondary antibodies (1:500; Life Technologies, Carlsbad, CA, USA) for 2 h at RT, protected from light. After secondary antibody labelling, cultures were washed 3×5 min in PBS, and finally stored in PBS at 4° C. prior to confocal imaging.

10.4 Confocal Imaging: Fluorescently labelled cultures were imaged on an Olympus FV1000 confocal microscope (Olympus, Tokyo, Japan). Regions of interested were manually selected and imaged using a 60× objective. Confocal Z-stacks were obtained for all images and processed using the maximum Z-projection function in the ImageJ software (FIJI, Open source software). (FIG. 10)

Example 11: Monoclonal Antibodies Detect Full Length Recombinant Tau in Sandwich Immunoassays (FIG. 11)

Anti-tau rabbit IgG clones #44 (Clone 2) and #66 (Clone 1) detect recombinant tau as part of an antibody pair in a MesoScale Discovery (MSD) assays. Standard curves were constructed using full length recombinant 2N4R tau (rPeptide, Watkinsville, GA, USA) and clone #44 (clone 2) or #66 (clone 1) as capture antibodies, in combination with either commercially available polyclonal antibody, K9JA (targeting amino acids 244-441; Agilent, Santa Clara, CA, USA), or commercially available monoclonal antibody, Tau5 (targeting amino acids 210-241; Thermo Fisher Scientific, Waltham, MA, USA). The limit of detection of each assay was approximately 80 μg/mL. Data demonstrate the utility of antibodies targeting the epitope of interest (SEQ ID NO: 1) in combination with commercially available monoclonal or polyclonal antibodies, for the detection of tau using sandwich immunoassays.

11.1 MesoScale Discovery (MSD) analyses (FIG. 11): Custom MSD assays were developed based on standard methods provided by the manufacturer (MesoScale Discovery, Rockville, MD, USA). Plates were coated with clone #44 (Clone 2) or #66 (Clone 1) as capture antibodies, by incubation at 4° C. overnight in PBS (1 μg/mL). Plates were then washed 1× with PBS and blocked with MSD Blocker A for 1 h at RT on a plate shaker. Following blocking, the plates were washed 1× with PBS+0.05% Tween (PBS-T), and then a recombinant 2N4R tau (rPeptide, Watkinsville, GA, USA) 1:5 serial dilution was added covering the range 0-10,000 μg/mL. The recombinant tau was incubated with the capture antibody in the plate at RT on a plate shaker for 2-3 hours at 4° C. The plate was then washed 3× with PBS-T, and detection antibody (commercially available antibodies: K9JA (1 μg/mL); or Tau5 (2 μg/mL) or HT7 (2 μg/mL) sulfotagged as per the MSD kit instructions) was added to each well. The detection antibody was incubated on the plates at 4° C. overnight.

Plates were then washed 3× with 0.05% PBS-T and labelled with MSD Sulfo-TAG anti-mouse or anti-rabbit secondary antibody (depending on the species of the detection antibody) at 1:500 in 0.05% PBS-T at RT on the plate shaker for 1 h. Following this, the plates were washed 3× with PBS-T, 150 μl 2×MSD read buffer was added to each well and incubated for 5 min before imaging on the MSD plate reader using a standard protocol.

Example 12: Anti-Tau IgGs Inhibit Uptake of Monomeric and Aggregated Tau into Human Neurons (FIG. 12)

Extracellular monomeric and aggregated tau is taken up by human neurons via a combination of endocytosis and macropinocytosis (Evans et al. (2018) Cell Rep 22(13): 3612-3624). This process occurs physiologically, but is also proposed to play a role in the pathogenic spreading of toxic forms of tau observed in tauopathies, including Alzheimer's disease. Inhibiting uptake of toxic tau species is therefore predicted to be therapeutically beneficial in limiting the spread of tau pathology in the brain. Neuronal uptake of tau can be assessed and quantified by measuring fluorescence associated with tau labelled with the pH-sensitive dye, pHrodo. Increased fluorescence occurs following internalisation of labelled tau into the acidic endosome compartment, thereby providing a dynamic measure of tau uptake/internalisation. Anti-tau IgG clones, #44 (Clone 2) and #66 (Clone 1) inhibit the uptake of pHrodo-labelled monomeric tau (FIG. 12A; by 65% and 71% inhibition respectively at 4 h) and pHrodo-labelled aggregated tau (FIG. 12B; by 56% and 47% inhibition respectively at 4 h) into human iPSC-derived neurons. Isotype control antibody (monoclonal rabbit IgG; Thermo Fisher Scientific, Waltham, MA, USA) had no significant effect on tau uptake in this system.

Data demonstrate that antibodies targeting SEQ ID NO: 1 are able to reduce the uptake of tau species containing this epitope, by human neurons. Such antibodies would therefore be predicted to limit the neuron-to-neuron propagation of toxic tau species that include this epitope (SEQ ID NO: 1) in Alzheimer's disease and tauopathies and thereby reduce/slow the progression of clinical symptoms in patients.

12.1 Production of human iPSC-derived cerebral cortex neurons: As detailed in Example 1.1

12.2 Generation of aggregated (oligomeric) tau species: Tau P301S_10×his-tag_avi-tag was overexpressed in BL21(DE3) bacteria. Cells were lysed using BugBuster (Millipore, Burlington, MA, USA) and clarified lysate was applied to a 5 mL HisTrapHP column (GE Healthcare, Chicago, IL, USA) in 2×PBS. Tau was eluted using a 0- to 500-mM imidazole gradient. Peak fractions were pooled and further purified in 2×PBS using a Superdex 200 16/60 gel filtration column (GE Healthcare, Chicago, IL, USA). Pooled fractions were then concentrated to approximately 8 mg/mL using a spin concentrator (Millipore, Burlington, MA, USA). Final protein concentration was determined by Nanodrop analysis.

1 mL tau P301S at 8 mg/mL was incubated with 4 mg/mL heparin (Sigma, St Louis, MO, USA) in PBS/30 mM 3-(N-morpholino)propanesulfonic acid (MOPS) (pH 7.2) at 37° C. for 72 h. Aggregated material was diluted in 9 mL PBS plus 1% (v/v) sarkosyl (Sigma, St Louis, MO, USA) and left rocking for 1 h at RT to completely solubilize any non-aggregated material. Insoluble tau was pelleted by ultracentrifugation for 1 h at 4° C. The pellet was resuspended in 1 mL PBS and sonicated at 100W for 3×20 s (Hielscher UP200St ultrasonicator; Teltow, Germany) to disperse clumps or protein and break large filaments into smaller species.

12.3 Labelling ofpurified recombinant tau: Monomeric recombinant 2N4R tau was purchased from rPeptide (Watkinsville, GA, USA). Aggregated tau was prepared as described above. Recombinant monomeric tau (150 μM) or equivalent aggregated tau concentration (~7 μg/mL) was incubated with 1.5 mM pHrodo Red Maleimide (dissolved in DMSO) and 1.5 mM tris(2-carboxyethyl)phosphine (1:10:10 molar ratio respectively) for 2 h in the dark at RT. Labelled samples were then subjected to size exclusion chromatography at 4° C. (Superdex 200 Increase 10/300 GL; GE Healthcare, Chicago, IL, USA) in 50 mM phosphate (pH 7.4) and 150 mM NaCl to remove unreacted dye. Oligomeric state of aggregates was assessed and found to be unaffected by labelling.

12.4 Quantification of tau uptake by human iPSC-derived cortical neurons: Monomeric tau (25 nM) and aggregated tau (50 nM) were prepared in N2B27 (Thermo Fisher Scientific, Waltham, MA, USA) and incubated with a 10-fold molar excess of antibody over tau (i.e. 250 and 50 nM IgG) for 90 min at 37° C. 100 μL antibody/tau mix was added to NDC neurons (day 60+) and fluorescence was imaged every 15 min for 4 h at 37° C./5% $CO_2$ from 18 fields per well using the Opera Phenix imaging system (Perkin Elmer, Waltham, MA, USA). Algorithms to identify 'intense spots' in the Alexa 568 channel were used to quantify the number of intense spots of fluorescence per well and these were plotted as mean+/−SEM from n=4 cells over time. One-way ANOVA with Dunnett's multiple comparison test was run vs no antibody control to determine significance.

Example 13. Monoclonal Anti-Tau IgGs Immunodeplete Tau Species from Conditioned Media Obtained from Human iPSC-Derived Neurons (FIG. 13)

Secretomes were collected from human iPSC-derived neuronal cultures (generated as described in Example 1.1) at 48 hour intervals between days 70 and 80 post-neuronal induction. Secretomes were clarified by centrifugation before freezing at −20° C. Samples were thawed on ice and dialysed against artificial cerebrospinal fluid (aCSF). Immunodepletion of tau was achieved by 2 rounds of 12 hour incubations with monoclonal antibody and protein G agarose beads at 4° C. Preimmune serum from a rabbit was used as a control to mock deplete samples. Secretomes were collected from iPSC-derived neuronal cultures generated from two genetically distinct trisomy 21 lines, and from one NDC. Quantification of tau levels using a mid-region (BT2 (ThermoFisher, Waltham, MA)/Tau5 antibody pair) MSD assay and a microtubule binding region (MTBR; K9JA/K9JA antibody pair) assay confirmed the presence of elevated tau levels in trisomy 21 secretomes compared to NDC. In addition, MTBR tau levels were substantially (at least 4×) lower than mid-region tau, indicative of cleavage events leading to the generation of mid-region tau fragments that lack the MTBR and/or C-terminal domains, or the presence of tau species in which the MTBR and/or C-terminal epitopes are unavailable. Clones #44 (Clone 2) and #66 (Clone 1) deplete tau species from all three secretomes (FIG. 13). Clones #44 (Clone 2) and #66 (Clone 1) depleted MTBR containing tau to a greater extent in the trisomy 21 secretomes (line B, dark grey bars, 58% and 47% depletion by #44 (Clone 2) and #66 (Clone 1) respectively; and, line C, black bars, 62% and 60% depletion by #44 (Clone 2) and #66 (Clone 1) respectively) than in the NDC secretome (pale grey bars, 42% and 17% depletion by #44 (clone 2) and #66 (clone 1) respectively), indicating an increase in relative levels of tau species that include both the MTBR and the target epitope (SEQ ID NO: 1) in trisomy 21 compared to NDC secretomes. Clones #44 (Clone 2) and #66 (Clone 1) depleted mid-region tau only from TS21 secretomes (not NDC), most notably from one batch (line C; 16% and 34% respectively) indicating a disease-specific presence of tau species containing both mid-region and target epitopes (SEQ ID NO: 1). These data demonstrate a shift in the balance of different tau species (potentially due to disease-specific cleavage events, altered post-translational modification and/or conformational changes) present in disease compared to NDC, leading to an increase in both absolute tau levels and the proportion of MTBR and/or MR containing tau that can be detected by antibodies targeting SEQ ID NO: 1.

TABLE 8

Shows the immunodepletion efficiency (in percent removed) of antibodies tested, relative to pre-immune serum, based on tau levels quantified using the mid-region and MTBR assays.

| Line | Assay | K9JA | Clone #44 (clone 2) | Clone #66 (clone 1) |
|---|---|---|---|---|
| A (NDC) | Mid-region | 15.8 | N/A | N/A |
| | MTBR | 25.3 | 42.2 | 17.2 |
| B (TS21) | Mid-region | 27.4 | 5.0 | 6.1 |
| | MTBR | 65.1 | 57.9 | 47.2 |
| C (TS21) | Mid-region | 30.1 | 16.0 | 33.8 |
| | MTBR | 66.2 | 62.0 | 60.3 |

Example 14. Tau-Mediated Blockade of In Vivo Long Term Potentiation (LTP) by Trisomy 21 Neuronal Secretomes is Prevented by Immunodepletion of Samples with IgG Clones #44 (Clone 2) or #66 (Clone 1) Prior to Dosing (FIG. 14)

Electrophysiology experiments were carried out on urethane-anesthetized (105-106 g/kg, intra-peritoneally) male Lister Hooded rats (250-350 g). Hippocampal LTP was measured by recording field excitatory postsynaptic potentials (EPSPs) from the stratum *radiatum* of CA1 in response to stimulation of the ipsilateral Schaffer collateral/commissural pathway before and after 200 Hz high frequency stimulation (HFS), as previously described (Hu et al. (2014) Nature Commun 5:3374). Secretomes were injected via cannula into the lateral ventricle of rats 30 min before the induction of synaptic plasticity.

All statistical analyses of LTP were conducted in v6.07 (GraphPad Software, La Jolla, CA, USA). The magnitude of LTP is expressed as the percentage of pre-HFS baseline EPSP amplitude (±SEM). The n refers to the number of animals per group. Control experiments were interleaved randomly throughout. For graphical representation, EPSP amplitudes were grouped into 5 min epochs; for statistical analyses, EPSP amplitudes were grouped into 10 min epochs. One way ANOVA with Sidak's multiple comparison test (one-way ANOVA-Sidak) was used for comparisons between groups of three or more. Two-way ANOVA with repeated measures with Sidak's multiple comparison test (two-way ANOVA RM-Sidak) was used when there were only two groups. Paired ttests were carried out to compare pre- and post-HFS values within groups. A value of $p<0.05$ was considered statistically significant.

The secretome isolated from trisomy 21 'line C' (shown in FIG. 13) was tested. Mock-depleted samples significantly blocked the induction of LTP ($p<0.01$), compared to vehicle control treated animals, consistent with the presence of 'toxic' or inhibitory molecules in the secretome, as previously described (Hu et al., 2014, Nat Commun 5: 3374). Trisomy 21 secretome that had been immune-depleted using either clone #44 (clone 2) or #66 (clone 1) to remove tau species including the target epitope (SEQ ID NO: 1) exhibited statistically significant LTP when compared to baseline ($p<0.01$ and $p<0.001$ respectively). Data demonstrate that the LTP block induced by Trisomy 21 secretomes can be prevented by removal of tau species that include the target epitope (SEQ ID NO: 1) and thereby show that C-terminal containing tau species are responsible for a component of the LTP block. Removal of these tau species in patients by administration of specific antibodies, would therefore be predicted to be therapeutically useful.

Example 15: Monoclonal Anti-Tau Antibodies with Effector Function Increase Tau Uptake by Microglia Microglia play an important role in clearing extracellular material in the central nervous system, to prevent accumulation of debris and enable repair processes to occur. In the context of neurodegenerative disease, phagocytosis of extracellular proteins, including aggregates, oligomers and monomeric forms, helps to reduce the extracellular concentrations of these species. Antibody clones #44 (Clone 2) and #66 (Clone 1) with effector function (i.e., rabbit IgG Fc) increase the uptake of both monomeric and aggregated tau by human iPSC-derived microglia compared to either tau alone or tau plus isotype control IgG conditions (FIG. 15). Data suggest that therapeutic antibodies with effector function (e.g., formatted as hIgG1) would increase clearance of toxic forms of tau by microglia, and thereby reduce the extracellular concentration and deleterious effects of toxic forms of tau in the CNS. This activity would be predicted to be therapeutically beneficial.

15.1 Imaging microglial uptake of pHrodo-labelled tau: Antibody clones #44 (Clone 2) and #66 (Clone 1) or an isotype control rabbit IgG were incubated with full length pHrodo-labelled monomeric aggregated tau (prepared as described in Example 12) before imaging on the OPERA-Phenix. pHrodo area per microglial area quantified after 3 h and subsequently every 30 mins increased steadily over time in isotype control (FIG. 15, open squares, solid line) and no antibody (FIG. 15, solid circles, dashed line) treatments, indicative of baseline level of phagocytosis. Internalisation of pHrodo-labelled tau was markedly increased in cells treated with anti-tau antibody clones.

Data are given as mean+/−SEM of n=4 wells from one representative experiment. One-way ANOVA with Dunnett's multiple comparison test was run versus no antibody control and significance recorded as: **, $p<0.0001$; *, $p<0.001$ (FIG. 15 C, D).

Example 16. Human AD CSF Contains C-Terminal Tau

In order for an antibody to effectively target tau in vivo/in patients, relevant tau species must be present extracellularly. To demonstrate the presence of extracellular tau species containing the epitope of interest (SEQ ID NO: 1) we purified tau from pooled cerebrospinal fluid (CSF) samples obtained from AD patients using antibody clone #44 (clone 2). The bound proteins were then digested using trypsin and resolved by mass spectrometry (FIG. 16). Multiple tau peptides were identified, including a C-terminal peptide (SPVVSGDTSPR; corresponding to amino acids 396-406 of 2N4R tau; SEQ ID NO: 12) located adjacent to the antibody epitope. These data confirm the presence of tau species that include both the antibody epitope (SEQ ID NO: 1) and other C-terminal regions in AD CSF, and demonstrate the presence of such species extracellularly. These C-terminal tau-containing species are therefore targetable by therapeutic antibodies and present in fluids that could be exploited for biomarker detection.

16.1 Human CSF samples: 16 de-identified samples of CSF from AD patients, leftover from clinical routine, were provided by H. Zetterberg (University of Gothenburg, Sweden). Such samples (not traceable back to any individual) may be used for method development and standardization, without specific ethical consent according to Swedish legislation. 16 CSF samples were pooled (total volume 8.5 mL). The final concentration of total tau in the pooled sample (calculated based on mid-region ELISA data from the individual samples) was 700 ng/mL.

16.2 Immunoprecipitation mass spectrometry: Protein A-coated Dynabeads were washed prior to incubation with 150 ng clone #44 (clone 2) overnight at 4° C. on a roller. IgG antibody bead mix was then added to pooled CSF samples and incubated for 3 days at 4° C. on a roller. Beads were washed three times with 0.02% tween (PBS) then resuspended in 20 mM Ammonium bicarbonate. An on bead trypsin digest was performed. Peptide masses were determined using a Bruker ultrafleXtreme Maldi mass spectrometer in reflectron mode and ms/ms fragmentation performed in LIFT mode. Data analysis was with FlexAnalysis, BioTools and ProteinScape software (Bruker, Billerica, MA, USA). Database searches of the combined mass fingerprint-ms/ms data were performed using Mascot (matrixscience.com).

Example 17. Anti-Tau IgGs Inhibit Uptake of Monomeric and Aggregated Tau into Human Astrocytes (FIG. 17)

Limited information is available on the uptake of extracellular tau species by human astrocytes, although this is known to occur in rodents (Martini-Stoica et al. J Exp Med 215(9): 2355-2377 (2018)). In addition, a recently described receptor for neuronal tau uptake, lipoprotein receptor-related protein 1 (LRP1), is reported to be expressed in astrocytes (Rauch et al. Nature 580(7803):381-385 (2020)), suggesting that the mechanisms of uptake may be shared. As a major cell type in the central nervous system, with putative roles in the propagation of tau pathology in Alzheimer's disease and tauopathy (reviewed in Sidoryk-Wegrzynowicz & Struzyrska Biochem J 476(22):3493-3504 (2019)) we explored whether antibodies targeting the sequence corresponding to amino acids 369 to 381 of 2N4R tau (SEQ ID NO: 1) have any impact on uptake of tau species by astrocytes.

Human iPSC-derived astrocytes readily take up both monomeric and aggregated tau species (FIG. 17). Incubation of tau with anti-tau clone #44, significantly (P<0.001) inhibits its uptake of monomeric 2N4R tau by 98.4±0.4% and of aggregated tau by 43.3±2.9% compared to uptake in the absence of antibody. Data provide evidence that therapeutic anti-tau antibodies targeting SEQ ID NO: 1, would reduce the uptake of extracellular tau by astrocytes, and thereby reduce the impact of astrocytes in the propagation of tau pathology. This activity is predicted to be therapeutically beneficial.

17.1 Production of human iPSC-derived astrocytes: Differentiation of human iPSC to astrocytes was carried out using iPSC lines from an NDC background. Neuroepithelial sheets were generated as described for cortical neurons (Shi et al., Nature Protocols 7(10): 1836-46, 2012; protocol followed to step 31). From day 16, cells were passaged with Accutase into new Matrigel-coated plates ($1.5\times10^6$ cells/well of a 6 well plate) and transferred into 'Astrocyte differentiation media 1' (neural maintenance media described in Shi et al., Nature Protocols 7(10): 1836-46, 2012; supplemented with 20 ng/mL FGF2, 20 ng/mL EGF) for 7 days, with media changes every other day. Cells were then passaged with Accutase into new Matrigel-coated plates (as before) and transferred into 'Astrocyte differentiation media 2' (Neural maintenance media supplemented with 10 ng/mL BDNF, 10 ng/mL CNTF, 1 μM purmorphamine) for 7 days, with media changes every other day. Astrocytes were then maintained in 'maturation media' (Neurobasal media, 1×B27 supplement, 1% FBS, 50 U/mL penicillin and 50 mg/mL streptomycin, 1×GlutaMAX) until use (at ~day 130+).

17.2 Generation of aggregated (oligomeric) tau species: See Example 12.2.

17.3 Labelling of purified recombinant tau: See Example 12.3.

P301S tau was used for both monomeric and aggregated tau preparations.

17.4 Quantification of tau uptake by human iPSC-derived astrocytes: Monomeric tau (25 nM) and aggregated tau (50 nM) were prepared in serum-free Optimem (ThermoFisher) media and incubated with tested antibodies at a 10-fold molar excess concentration (i.e. 250 and 500 nM IgG respectively) for 90 min at 37° C. 200 μL antibody/tau mix was added to iPSC-derived astrocytes and images were taken (bright field and orange channel) every hour for 20 h at 37° C./5% $CO_2$ from 9 fields per well using the Incucyte S3 imaging system (Sartorius, Göttingen, Germany). Algorithms to quantify (per well) the mean area of fluorescence in the orange channel (excitation: 513-568 nm) were normalised to the mean area occupied by cells (phase area), and this was plotted as mean+/−SEM from 4 wells over time. One-way ANOVA with Tukey's multiple comparison test was run vs no antibody control to determine significance.

Example 18. Monoclonal Anti-Tau Chimeric Human IgG1 Increase Uptake of Monomeric and Aggregated Tau by Human iPSC-Derived Microglia As described in Example 15, monoclonal anti-tau rabbit IgG with effector function, increased uptake of both monomeric and aggregated tau by microglia. This increase in tau uptake was also observed with anti-tau human IgG1. Antibody clone #66 (Clone 1) expressed as a chimeric human IgG1 (i.e. with effector function) significantly increased the uptake of both monomeric (by 56±7%; P<0.001) and aggregated tau (by 59±9%; P<0.05) by human iPSC-derived microglia compared to uptake of tau alone (FIG. 18). Isotype control human IgG had no significant effect on microglial uptake of monomeric (6.7±6% reduction) or aggregated tau (23±9% reduction), compared to baseline tau uptake in the absence of antibody. Data provided further evidence that therapeutic hIgG1 would increase clearance of extracellular tau by microglia, and thereby reduce the extracellular concentration and deleterious effects of extracellular forms of tau in the CNS. This activity is predicted to be therapeutically beneficial.

18.1 Production of chimeric hIgG1 antibodies: Chimeric hIgG1 were generated by Absolute Antibody (Oxford, UK) using the rabbit VH and VK sequences (#66, Clone 1 SEQ ID NO: 116 and SEQ ID NO: 117) using proprietary methods (HEXpress™ service). Briefly, antibodies were produced following transient expression in HEK293 cells, affinity purified, buffer exchanged into phosphate buffered saline, sterile filtered and provided at a purity of >98% (based on SDS-PAGE) with <1 EU/mg endotoxin.

18.2 Production of human iPSC-derived microglia: Differentiation of human pluripotent stem cells (iPSC) to microglial cultures was carried out as described by Brownjohn et al. Stem Cell Rep 10(4): 1294-1307 (2018). An iPSC line from an NDC background was used. Microglial progenitor cells were collected, plated in 96 well plates and maintained in complete microglia media (as described in Brownjohn et al., 2018) for approximately 14 days before use. On the day prior to use, cultures were switched into serum free media (RPMI 1640/Glutamax supplemented with 10 ng/mL GM-CSF and 100 ng/mL IL-34 (growth factors from Peprotech, NJ, US)) and phagocytosis experiments were completed in serum-free conditions.

18.3 Generation of aggregated (oligomeric) tau species: See Example 12.2

18.4 Labelling of purified recombinant tau: See Example 12.3.

P301S tau was used for both monomeric and aggregated tau preparations.

18.5 Quantification of tau uptake by human iPSC-derived microglia: Monomeric tau (25 nM) and aggregated tau (50 nM) were prepared in serum-free microglial media and incubated with a 1:10 ratio of antibody:tau (i.e. 2.5 and 5 nM IgG respectively) for 90 min at 37° C. Anti-tau hIgG1 was compared to an isotype control (anti-fluorescein [4-4-20 (enhanced)], Absolute Antibody, Oxford, UK). 100 μL antibody/tau mix was added to iPSC-derived microglia and images were taken (bright field and orange channel) every 30 min for 16 h at 37° C./5% $CO_2$ from 9 fields per well using the Incucyte S3 imaging system (Sartorius, Göttingen, Germany). Algorithms to quantify (per well) the mean area of fluorescence in the orange channel (excitation: 513-568 nm), normalised to the mean area occupied by cells (phase area) and this was plotted as mean+/−SEM from n=4 cells over time. One-way ANOVA with Tukey's multiple comparison test was run vs no antibody control to determine significance.

Example 19. Anti-Tau IgG Bind to Tau with High Affinity

Anti-tau IgGs bind to full length 2N4R tau (SEQ ID NO: 2) with high affinity. Clone #66 (Clone 1) and clone #44 (Clone 2) bind to full length recombinant 2N4R tau with KDs of 2.39 nM and 3.83 nM respectively (FIG. 19, Table 9). It is predicted that the binding affinity of these antibodies would be equivalent to any tau species containing the epitope corresponding to that present within amino acids 369-381 of 2N4R tau (SEQ ID NO: 1), if this sequence is accessible.

19.1 Production of chimeric hIgG1 antibodies: Clone #66 hIgG1 was generated as described in Example 18.1. Clone #44 (VH SEQ ID NO: 118 and VL SEQ ID NO: 119) hIgG1 was generated by Abzena (Cambridge, UK) using proprietary methods. Briefly, antibodies were produced following transient expression in CHO cells, affinity purified, buffer exchanged into phosphate buffered saline, sterile filtered and provided at a purity of >98% (following size exclusion chromatography).

19.2 Assessment of antibody binding to tau: Binding of anti-tau hIgG1 to full length recombinant 2N4R tau (Rpeptide; SEQ ID NO: 2) was assessed using the Biacore T200 (GE Healthcare, Chicago, IL, USA) running Biacore T200 Evaluation Software V2.0.1. hIgG1 were immobilised on a Protein A capture sensor chip in running buffer (HBS-EP+ buffer containing 1 mg/mL BSA) at 25° C., captured to ~50 RU at 10 μL/min. For multi-cycle kinetics experiments (clone #66), recombinant 2N4R tau was flowed at concentrations ranging from 0.39 nM to 50 nM in running buffer at 40 μL/min, with an association time of 150 s and a dissociation time of 250 s. Optimised conditions for multiple-cycle kinetics experiments were applied to clone #44: recombinant 2N4R tau was flowed at concentrations ranging from 0.39 nM to 12.5 nM (2-fold dilutions) with an association time of 60 s and a dissociation time of 200 s (cropped to 65 s to improve analysis fit). Curves were compared to a reference cell that was mock immobilized (no antibody present).

Data were analysed using Langmuir (1:1) binding analysis, describing a 1:1 interaction at the surface:

$$A + B \underset{k_d}{\overset{k_a}{\rightleftarrows}} AB$$

$$K_D = \frac{k_d}{k_a}$$

Where: $k_a$ is the association rate constant ($M^{-1}s^{-1}$) and $k_d$ is the dissociation rate constant ($s^{-1}$) Closeness of fit was judged in terms of the Chi square value, which describes the deviation between the experimental and fitted curves:

$$\text{Chi square} = \frac{\sum (r_f - r_x)^2}{n - p}$$

Where: rf is the fitted value at a given point, rx is the experimental value at the same point, n is the number of data points, p is the number of fitted parameters. The fitting algorithm sought to minimise Chi square.

TABLE 9

Summary of MCK binding analysis data for clones #66 (Clone 1) and #44 (Clone 2) binding to full length recombinant 2N4R tau.

| Antibody | $K_a$ (1/Ms) | $K_d$ (1/s) | $K_D$ (M) | $R_{MAX}$ | $Chi^2$ ($RU^2$) |
|---|---|---|---|---|---|
| #66 | 2.01E+06 | 0.004783 | 2.39E−09 | 25.98 | 0.194 |
| #44 | 2.07E+06 | 9.68E−03 | 4.68E−09 | 30.5 | 0.041 |

Example 20: Anti-Tau Antibodies Bind to Distinct Epitopes within the Region ${}_{373}$THKLTFR${}_{379}$ Epitope fine mapping was carried out to identify critical residues within the synthetic peptide amino acids 369-381 of 2N4R tau (SEQ ID NO: 1) that define the epitope and are required for antibody binding. In a replacement analysis, each residue was mutated to other amino acids to evaluate the importance of the residue for binding to the antibody.

For antibody clone #44 (Clone 2), the replacement analysis showed that amino acid residues in the region, ${}_{373}$THKLTFR${}_{379}$ (SEQ ID NO: 150) were important for binding (FIG. 20A). Specifically, residues, $T_{373}$, $K_{375}$, $T_{377}$ and $R_{379}$ were important for antibody binding, as substitution of these residues resulted in a drop of intensity for all substitutes. Substitution of $K_{375}$, $T_{377}$ and $R_{379}$, reduced signal intensities to background level, suggesting that these residues are critical for binding of this clone.

For antibody clone #66 (Clone 1), ${}_{374}$HKL${}_{376}$ and ${}_{378}$FR${}_{379}$ were important for binding (FIG. 20B). Specifically, substitution of $L_{376}$ or $F_{378}$ resulted in reduced antibody binding for all substitutes, suggesting a key role of these residues for binding of this clone.

Little binding of the isotype control rabbit IgG was detected in this system (FIG. 20C), indicating that the ELISA signal obtained for anti-tau antibody clones #44 and #66 was CDR-specific.

Data demonstrate that the antibodies described here, exemplified by clones #44 (Clone 2) and #66 (Clone 1) bind to different specific epitopes within the peptide sequence of amino acids 369-381 of 2N4R tau (SEQ ID NO: 1). The antibodies described share functional properties, indicating that it is the epitopes within and formed by this sequence 369-381 of 2N4R tau that dictate functional outcome.

20.1 Epitope substitution scan analysis—peptide synthesis: Replacement analysis was conducted by Pepscan Presto BV (Lelystad, The Netherlands) using proprietary methods. Briefly, a library of peptides was synthesised using Fmoc-based solid-phase peptide synthesis. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Peptides were designed based on the starting epitope (${}_{369}$KKIETHKLTFREN${}_{381}$; SEQ ID NO: 1) such that each amino acid was mutated, one at a time, to every other natural amino acid. The order of peptides on the mini-cards was randomised and data were compared to that obtained with an isotype control antibody (rabbit IgG; Abcam, Cambridge, UK). 20.2 Epitope substitution scan analysis—ELISA screening: The binding of antibody to each of the synthesized peptides was tested in a Pepscan-based ELISA. The peptide arrays were incubated with primary antibody solution (5 μg/mL; overnight at 4° C.). After washing, the peptide arrays were incubated with a 1/1000 dilution of a swine anti-rabbit IgG peroxidase conjugate (DAKO, Jena, Germany) for 1 h at 25° C. After washing, the peroxidase substrate 2,2'-azino-di-3-ethylbenzthiazoline sulfonate (ABTS) and 20 μL/mL of 3% $H_2O_2$ were added. After 1 h, the colour development was measured. The colour development was quantified with a charge coupled device (CCD)—camera and an image processing system. Values obtained from the CCD camera are quoted (range: 0 to 3000 mAU).

Data are presented as letter plots showing ELISA signal obtained for each peptide tested. Observed deviations from the maximum ELISA signal are indicative of mutations associated with altered (reduced) binding of the tested antibody to the target peptide.

Example 21. Anti-Tau Antibody #44 Detects Increased Levels of High and Low MW Tau Species in Familial Alzheimer's Disease, Sporadic Alzheimer's Disease and Dementia with Lewy Bodies Brain Compared to Non-Demented Control Brain, that are not Detected by Antibodies Targeting N-Terminal, Mid-Region or Far C-Terminal Sequences Building on data described in Examples 8 and 9 (describing antibody #66, Clone 1, SEQ ID NO: 116 and 117), antibody clone #44 (Clone 2, SEQ ID NO: 118 and 119) was profiled to explore the species of tau detected across a range of tauopathies and across a panel of patient samples. Clone #44 detected increased levels of both high and low MW species across a panel of patient samples representing familial Alzheimer's disease (fAD, Presenilin 1 mutations), sporadic Alzheimer's disease (sAD) and Dementia with Lewy bodies (DLB) (FIG. 21). Actin and neuronal tubulin controls confirm that changes in tau levels are not due to variations in protein and/or neuronal levels in the samples tested. Data confirm that clone #44 detects disease-relevant tau species in a similar manner to that described for antibody clone #66 (clone 1, Examples 8, 9), and suggest that other antibodies binding to SEQ ID NO: 1, are likely to behave similarly and have the potential to be therapeutically useful in the treatment of AD and tauopathy.

In addition, detection of tau species by commercially-available tau antibodies showed limited detection of disease-specific tau species across fAD, sAD and DLB brain samples (FIG. 21), in both the higher and lower molecular weight range, the commercially-available antibodies used were N-terminal Taul3 (that targets amino acids 2-18 of tau, Abcam, Cambridge, UK), mid-region HT7 (that targets amino acids 159-163 of tau, Invitrogen, Carlsbad, CA, USA) and Tau5 (that targets amino acids 210-241 of tau, Thermo Fisher Scientific, Waltham, MA, USA), and far C-terminal tau Tau46 (that targets amino acids 404-441 of tau, New England Biolabs, Ipswich, MA, USA). Data demonstrate that antibodies targeting epitopes present within the sequence corresponding to amino acids 369-381 of 2N4R tau (SEQ ID NO: 1) bind to disease-specific tau species that are not detected by a range of antibodies targeting N-terminal, mid-region or far C-terminal regions of tau, and therefore show unique and beneficial properties related to the targeted sequence.

21.1 Human brain samples: See Examples 8.2 and 9.2 for details.

21.2 Western blot: See Example 7.1-7.5 for full details. Note that to minimise the influence of contaminating human IgG present in the postmortem brain samples, Tidyblot (Bio-Rad, Hercules, CA, USA) was used at a dilution of 1:200 in place of a standard secondary antibody when using hIgG1 for detection.

REFERENCES

Altschul S F, Gish W, Miller W, Myers E W & Lipman D J (1990) Basic local alignment search tool. *J. Mol. Biol.* 215: 405-410

Augustinack J C, Schneider A, Mandelkow E M, Hyman B T (2002) Specific tau phosphorylation sites correlate with severity of neuronal cytopathology in Alzheimer's disease. *Acta Neuropathol* 103(1):26-35

Brownjohn P W, Smith J, Solanki R, Lohmann E, Houlden H, Hardy J, Dietmann S, Livesey F J (2018) Functional studies of missense TREM2 mutations in human stem cell-derived microglia. *Stem Cell Rep* 10(4): 1294-1307

Edgar R C. 2004a. MUSCLE: multiple sequence alignment with high accuracy and high throughput. Nucleic Acids Res 32:1792-7.

Edgar R C. 2004b. MUSCLE: a multiple sequence alignment method with reduced time and space complexity. BMC Bioinformatics 5:113.

Evans L D, Wassmer T, Fraser G, Smith J, Perkinton M, Billinton A & Livesey F J (2018) Extracellular monomeric and aggregated tau efficiently enter human neurons through overlapping but distinct pathways. *Cell Rep* 22(13): 3612-3624

Hancock D C, O'Reilly N J (2005) Production of polyclonal antibodies in rabbits. *Methods Mol Biol* 295: 27-40

Hu S, Shively L, Raubitschek A, Sherman M, Williams L E, Wong J Y, Shively J E & Wu A M (1996) Minibody: A novel engineered anti-carcinoembryonic antigen antibody fragment (single-chain Fv-CH3) which exhibits rapid, high level targeting of xenografts. *Cancer Res* 56(13): 3055-61

Hu N W, Nicoll A J, Zhang D, Mably A J, O'Malley T, Purro S A, Terry C, Collinge J, Walsh D M, Rowan M J (2014) mGlu5 receptors and cellular prion protein mediate amyloid b-facilitated synaptic long-term depression in vivo. *Nat Commun* 5: 3374

Kabat E A & Wu T T (1991) Identical V region amino acid sequences and segments of sequences in antibodies of different specificities. Relative contributions of V H and V L genes, minigenes, and complementarity-determining regions to binding of antibody-combining sites. *J Immunol* 147(5): 1709-19

Kontermann R E (2012) Dual targeting strategies with bispecific antibodies. *Mabs* 4(2): 182-97

Lefranc M P, Pommie C, Kaas Q, Duprat E, Bosc N, Guiraudou D, Jean C, Ruiz M, Da Piedade I, Rouard M, Foulquier E, Thouvenin V, Lefranc G (2005) IMGT unique numbering for immunoglobulin and T cell receptor constant domains and Ig superfamily C-like domains. *Dev Comp Immunol* 29(3): 185-203

Martini-Stoica H, Cole A L, Swartzlander D B, Chen F, Wan Y-W, Bajaj L, Bader D A, Lee VMY, Trojanowski J Q, Liu Z, Sardiello M, Zheng H (2018) TFEB enhances astroglial uptake of extracellular species and reduces tau spreading. *J Exp Med* 215(9): 2355-2377

Moore S, Evans LDB, Andersson T, Portelius E, Smith J, Dias T B, Saurat N, McGlade A, Kirwan P, Blennow K, Hardy J, Zetterberg H, Livesey F J (2015) APP metabolism regulates tau proteostasis in human cerebral cortex neurons. *Cell Reports* 11(5): 689-96

Morris M, Knudsen Gm, Maeda S, Trinidad J C, loanoviciu A, Burlingame A L & Mucke L (2015) Tau post-translational modifications in wild-type and human amyloid precursor protein transgenic mice. *Nature Neurosci* 18: 1183-1189

Pearson W R & Lipman D J (1988) Improved tools for biological sequence comparison. *Proc Natl Acad Sci USA* 85: 2444-2448

Pedersen J T & Sigurdsson E M (2015) Tau immunotherapy for Alzheimer's disease. *Trends Mol Med* 21(6): 394-402

Rauch J N, Luna G, Guzman E, Audouard M, Challis C, Sibih Y E, Leshuk C, Hernandez I, Wegmann S, Hyman B T, Gradinaru V, Kampmann M, Kosik K S (2020) LRP1 is a master regulator of tau uptake and spread. *Nature* 580(7803): 381-385

Roberts M, Sevastou I, Imaizumi Y, Mistry K, Talma S, Dey M, Gartlon J, Ochiai H, Zhou Z, Akasofu S, Tokuhara N, Ogo M, Aoyama M, Aoyagi H, Strand K, Sajedi E, Agarwala K L, Spidel J, Albone E, Horie K, Staddon J M, deSilva R (2020) Pre-clinical characterisation of E2814, a high-affinity antibody targeting the microtubule-binding repeat domain of tau for passive immunotherapy in Alzheimer's disease. *Acta Neuropathologica Comms* 8:13

Sandusky-Beltran L A, Sigurdsson E M (2020) Tau Immunotherapies: lessons Learned, Current Status and Future Considerations. *Neuropharmacol.* 175: 108104

Shi Y, Kirwan P, Smith J, Robinson HPC, Livesey F J (2012a) Human cerebral cortex development from pluripotent stem cells to functional excitatory synapses. *Nature Neurosci* 15(3): 477-86

Shi Y, Kirwan P, Livesey F J (2012b) Directed differentiation of human pluripotent stem cells to cerebral cortex neurons and neural networks. *Nature Protocols* 7(10): 1836-46

Shi Y, Kirwan P, Smith J, MacLean G, Orkin S H, Livesey F J (2012c) A human stem cell model of early Alzheimer's disease pathology in Down Syndrome. *Science Trans Med* 4(124): 124ra29

Sidoryk-Wegrzynowicz M & Struzyrska L (2019) Astroglial contribution to tau-dependent neurodegeneration. *Biochem J* 476(22):3493-3504

Smith T F & Waterman M S (1981) Identification of common molecular subsequences. *J. Mol Biol.* 147: 195-197

Spiess C, Zhai Q & Carter P J (2015) Alternative molecular formats and therapeutic applications for bispecific antibodies. *Mol Immunol* 67 (2 Pt A): 95-106

Sposito T, Preza E, Mahoney C J, Seto-*Salvia* N, Ryan N S, Morris H R, Arber C, Devine M J, Houlden H, Warner T T, Bushell T J, Zagnoni M, Kunath T, Livesey F J, Fox N C, Rossor M N, Hardy J, Wray S (2015) Developmental regulation of tau splicing is disrupted in stem cell-derived neurons from frontotemporal dementia patients with the 10+16 splice-site mutation in MAPT. *Hum Mol Genet* 24(18): 5260-5269

SEQUENCE LISTING

The sequence listing submitted herewith forms part of the specification as filed.

The invention claimed is:

1. An antibody or antigen-binding fragment thereof, comprising an antigen-binding site comprising HCDR1, HCDR2, HCDR3, LCDR1, LCDR2 and LCDR3 of antibody:

(a) Clone 1 of SEQ ID NO: 14, SEQ ID NO: 15, SEQ ID NO: 16, SEQ ID NO: 17, SEQ ID NO: 18 and SEQ ID NO: 19;

(b) Clone 2 of SEQ ID NO: 20, SEQ ID NO: 21, SEQ ID NO: 22, SEQ ID NO: 23, SEQ ID NO: 24 and SEQ ID NO: 25;

(c) Clone 3 of SEQ ID NO: 26, SEQ ID NO: 27, SEQ ID NO: 28, SEQ ID NO: 29, SEQ ID NO: 30 and SEQ ID NO: 31;

(d) Clone 4 of SEQ ID NO: 32, SEQ ID NO: 33, SEQ ID NO: 34, SEQ ID NO: 35, SEQ ID NO: 36 and SEQ ID NO: 37;

(e) Clone 5 of SEQ ID NO: 38, SEQ ID NO: 39, SEQ ID NO: 40, SEQ ID NO: 41, SEQ ID NO: 42 and SEQ ID NO: 43;

(f) Clone 6 of SEQ ID NO: 44, SEQ ID NO: 45, SEQ ID NO: 46, SEQ ID NO: 47, SEQ ID NO: 48 and SEQ ID NO: 49;

(g) Clone 7 of SEQ ID NO: 50, SEQ ID NO: 51, SEQ ID NO: 52, SEQ ID NO: 53, SEQ ID NO: 54 and SEQ ID NO: 55;

(h) Clone 8 of SEQ ID NO: 56, SEQ ID NO: 57, SEQ ID NO: 58, SEQ ID NO: 59, SEQ ID NO: 60 and SEQ ID NO: 61;

(i) Clone 9 of SEQ ID NO: 62, SEQ ID NO: 63, SEQ ID NO: 64, SEQ ID NO: 65, SEQ ID NO: 66 and SEQ ID NO: 67;

(j) Clone 10 of SEQ ID NO: 68, SEQ ID NO: 69, SEQ ID NO: 70, SEQ ID NO: 71, SEQ ID NO: 72 and SEQ ID NO: 73;

(k) Clone 11 of SEQ ID NO: 74, SEQ ID NO: 75, SEQ ID NO: 76, SEQ ID NO: 77, SEQ ID NO: 78 and SEQ ID NO: 79;

(l) Clone 12 of SEQ ID NO: 80, SEQ ID NO: 81, SEQ ID NO: 82, SEQ ID NO: 83, SEQ ID NO: 84 and SEQ ID NO: 85;

(m) Clone 13 of SEQ ID NO: 86, SEQ ID NO: 87, SEQ ID NO: 88, SEQ ID NO: 89, SEQ ID NO: 90 and SEQ ID NO: 91;

(n) Clone 14 of SEQ ID NO: 92, SEQ ID NO: 93, SEQ ID NO: 94, SEQ ID NO: 95, SEQ ID NO: 96 and SEQ ID NO: 97;

(o) Clone 15 of SEQ ID NO: 98, SEQ ID NO: 99, SEQ ID NO: 100, SEQ ID NO: 101, SEQ ID NO: 102 and SEQ ID NO: 103;

-continued (p) Clone 16 of SEQ ID NO: 104, SEQ ID NO: 105, SEQ ID NO: 106, SEQ ID NO: 107, SEQ ID NO: 108 and SEQ ID NO: 109; or (q) Clone 17 of SEQ ID NO: 110, SEQ ID NO: 111, SEQ ID NO: 112, SEQ ID NO: 113, SEQ ID NO: 114 and SEQ ID NO: 115;

wherein the sequences are defined according to Kabat nomenclature.

2. The antibody or antigen-binding fragment thereof according to claim 1, wherein the antibody or fragment thereof comprises an antigen-binding site comprising VH and VL domain sequences of, or a VH and VL domain sequence with at least 90, 91, 92, 93, 94, 95, 96, 97, 98 or 99% identity to, a clone selected from:

(a) Clone 1 of SEQ ID NO: 116 and SEQ ID NO: 117, respectively;

(b) Clone 2 of SEQ ID NO: 118 and SEQ ID NO: 119, respectively;

(c) Clone 3 of SEQ ID NO: 120 and SEQ ID NO: 121, respectively;

(d) Clone 4 of SEQ ID NO: 122 and SEQ ID NO: 123, respectively;

(e) Clone 5 of SEQ ID NO: 124 and SEQ ID NO: 125, respectively;

(f) Clone 6 of SEQ ID NO: 126 and SEQ ID NO: 127, respectively;

(g) Clone 7 of SEQ ID NO: 128 and SEQ ID NO: 129, respectively;

(h) Clone 8 of SEQ ID NO: 130 and SEQ ID NO: 131, respectively;

(i) Clone 9 of SEQ ID NO: 132 and SEQ ID NO: 133, respectively;

(j) Clone 10 of SEQ ID NO: 134 and SEQ ID NO: 135, respectively;

(k) Clone 11 of SEQ ID NO: 136 and SEQ ID NO: 137, respectively;

(l) Clone 12 of SEQ ID NO: 138 and SEQ ID NO: 139, respectively;

(m) Clone 13 of SEQ ID NO: 140 and SEQ ID NO: 141, respectively;

(n) Clone 14 of SEQ ID NO: 142 and SEQ ID NO: 143, respectively;

-continued

```
(o) Clone 15 of SEQ ID NO: 144 and SEQ ID NO:
145, respectively;

(p) Clone 16 of SEQ ID NO: 146 and SEQ ID NO:
147, respectively; or

(q) Clone 17 of SEQ ID NO: 148 and SEQ ID NO:
149, respectively;
```

wherein the sequences are defined according to Kabat nomenclature.

3. The antibody or antigen-binding fragment thereof according to claim 1, wherein the antibody or fragment thereof comprises VH and VL domain sequences of Clone 1 according to SEQ ID NO: 116 and SEQ ID NO: 117 or of Clone 2 according to SEQ ID NO: 118 and SEQ ID NO: 119.

4. The antibody or antigen-binding fragment thereof according to claim 1, wherein the antibody is a chimeric antibody comprising a human IgG Fc region.

5. The antibody or antigen-binding fragment thereof according to claim 1, wherein the antibody comprises an IgG Fc region with effector function or enhanced effector function.

6. The antibody or antigen-binding fragment thereof according to claim 1, wherein the antibody or antigen-binding fragment thereof is an expression product of a recombinant DNA or RNA sequence.

7. An isolated recombinant DNA or RNA sequence comprising a sequence encoding the antibody or antigen-binding fragment thereof according to claim 1.

8. An expression vector comprising the isolated recombinant DNA sequence of claim 7.

9. The expression vector of claim 8, further comprising a promoter.

10. A host cell comprising a DNA or RNA sequence according to claim 7.

11. The host cell of claim 10, comprising an expression vector comprising the recombinant DNA sequence of claim 7.

12. A method of making an isolated antibody or antigen-binding fragment thereof comprising culturing the host cell of 11 in conditions suitable for expression of the isolated antibody or antigen-binding fragment thereof, expressing the antibody or antigen-binding fragment thereof and isolating the expressed antibody or antigen-binding fragment thereof.

13. A composition comprising the antibody or antigen-binding fragment thereof according to claim 1 and a pharmaceutically acceptable diluent.

14. A method for treatment of tauopathy in a subject in need thereof, comprising administering to the subject in need thereof the composition of claim 13, wherein the tauopathy is selected from Alzheimer's disease, amyotrophic lateral sclerosis/parkinsonism-dementia complex, argyrophilic grains disease, beta-propeller protein associated neurodegeneration (BPAN), British type amyloid angiopathy, cerebral amyloid angiopathy, Creutzfeldt-Jakob disease, dementia pugilistica, diffuse neurofibrillary tangles with calcification, Down's syndrome, chronic traumatic encephalopathy (CTE), corticobasal degeneration (CBD), frontotemporal dementia (FTD), parkinsonism linked to chromosome 17 (FTDP-17), frontotemporal lobar degeneration, Gerstmann-Straussler-Scheinker disease, Hallervorden-Spatz disease, inclusion body myositis, multiple system atrophy, myotonic dystrophy, Niemann-pick disease type C, nonguamanian motor neuron disease with neurofibrillary tangles, Pick's disease, post-encephalitic parkinsonism, primary age-related tauopathy (PART), prion protein cerebral amyloid angiopathy, progressive subcortical gliosis, progressive supranuclear palsy (PSP), subacute sclerosing panencephalitis, tangle-dominant dementia, globular glial tauopathy, parkinsonism dementia complex of Guam, progressive non-fluent aphasia, multi-infarct dementia, ischemic stroke, traumatic brain injury (TBI) or stroke.

15. The method of claim 14, wherein the treatment comprises one or more of reducing uptake of extracellular monomeric or aggregated tau species by human neurons, promoting uptake of tau species by human astrocytes, preventing uptake of tau species by human astrocytes, increasing phagocytosis of tau species in human microglia, and/or preventing tau-mediated inhibition of long term potentiation in rodent models.

16. A method to identify human tau proteins comprising an epitope formed by residues 369-381 (SEQ ID NO: 1) of human 2N4R tau (SEQ ID NO: 2) comprising contacting a sample with the antibody or antigen-binding fragment thereof according to claim 1.

17. A method to identify human tau proteins comprising an epitope formed by residues 373-379 (THKLTFR, SEQ ID NO: 150) of human 2N4R (amino acids 1-441) tau (SEQ ID NO: 2) comprising contacting a sample with the antibody or antigen-binding fragment thereof according to claim 1.

18. A method for diagnosing tauopathy in a subject, comprising providing a sample from the subject and contacting the sample with the antibody or antigen-binding fragment thereof according to claim 1, wherein the tauopathy is diagnosed when the antigen-binding protein binds human tau proteins.

19. A diagnostic kit comprising the antibody or antigen-binding fragment thereof according to claim 1, and a reagent capable of detecting an immunological complex comprising the antibody or antigen-binding fragment thereof, wherein the antibody or antigen-binding fragment thereof is immobilized on a solid support.

20. The diagnostic kit according to claim 19, further comprising one or more control standards, specimen diluent and/or washing buffer.

* * * * *